(12) United States Patent
Unutmaz et al.

(10) Patent No.: US 8,992,933 B2
(45) Date of Patent: Mar. 31, 2015

(54) METHODS FOR ACTIVATING T CELLS AND MODULATING AN IMMUNE RESPONSE

(75) Inventors: Derya Unutmaz, New York, NY (US); Qi Wan, New York, NY (US); Lina Kozhaya, Brooklyn, NY (US)

(73) Assignee: New York University, New York, NY (US)

( * ) Notice: Subject to any disclaimer, the term of this patent is extended or adjusted under 35 U.S.C. 154(b) by 0 days.

(21) Appl. No.: 13/548,277

(22) Filed: Jul. 13, 2012

(65) Prior Publication Data
US 2013/0058964 A1 Mar. 7, 2013

Related U.S. Application Data

(60) Provisional application No. 61/572,339, filed on Jul. 14, 2011.

(51) Int. Cl.
*A61K 39/00* (2006.01)
*C07K 14/435* (2006.01)

(52) U.S. Cl.
CPC .................................. *A61K 39/0008* (2013.01)
USPC ........................................ 424/184.1; 530/350

(58) Field of Classification Search
None
See application file for complete search history.

(56) References Cited

PUBLICATIONS

Korn et al, Annual Review of Immunology, 2009, vol. 27, pp. 485-517.*
Akdis et al, Allergy Clinical Immunology, 2012, vol. 129, pp. 1438-1449, p. 1439.*
Gregersen et al, Nature Reviews, 2006, vol. 7, pp. 917-928.*
Wu et al, Oncogene, 2004, vol. 23, pp. 8088-8096.*
Crystal, R. Science, vol. 270, 1995, pp. 404-410.*
Rubanyi , Molecular Aspects of Medicine, (2001) , vol. 22, pp. 113-142.*
Juengst , British Medical Journal (2003) vol. 326, pp. 1410-1414.*
Acosta-Rodriguez, et al., "Surface phenotype and antigenic specificity of human interlukin 17-producing T helper memory cells" Nat Immunol (2007) 8(6):639-46.
Acosta-Rodriguez, et al., "Interleukins 1beta and 6 but not transforming growth factor-beta are essential for the differentiation of interleukin 17-producing human T helper cells" Nat Immunol (2007) 8(9):942-9.
Annunziato, et al., "Phenotypic and functional features of human TH17cells" J Exp Med (2007) 204(8):1849-61.
Annunziato, et al., "Heterogeneity of human effector CD4+ T cells" Arthritis Res Ther (2009) 11(6)257.
Attur, et al., "Interleukein-17 up-regulation of nitric oxide production in human osteoarthritis cartilage", Arthritis Rheum (1997) 40(6):1050-3.
Barata, et al., Activation of PI3K is indispensable for interleukin 7-mediated viability, proliferation, glucose use, and growth of T cell acute lymphoblastic leukemia cells J Exp Med (2004) 200(5):659-69.
Becker, et al., "Constitutive p40 promoter activation and IL-23 production in the terminal ileum mediated by dendritic cells" J Clin Invest (2003) 112(5):693-706.
Bettelli, et al., "Th17: the third member of the effector T cell trilogy", Curr Opin Immunol (2007) 19(6):652-7.
Bettelli, et al., "Reciprocal developmental pathways for the generation of pathogenic effector TH17 and regulatory T cells" Nature (2006) 441: 235-8.
Brunet, et al., "Akt promotes cell survival by phosphorylating and inhibiting a Forkhead transcription factor" Cell (1999) 96(6):857-68.
Bu, et al., "Statin-induced Kruppel-like factor 2 expression in human and mouse T cells reduces inflammatory and pathogenic responses" J Clin Invest (2010) 120(6) 1961-70.
Chabaud, et al., "Human interleukin-17:A T cell-derived proinflammatory cytokine produced by the rheumatoid synovium" Arthritis Rheum (1999) 42(5) 963-70.
Chen, et al., "Distinct regulation of interleukin-17 in human T helper lymphocytes" Arthritis Rheum (2007) 56 (9):2936-46.
Cua, et al., "Interleukin-23 rather than interleukin-12 is the critical cytokine for autoimmune inflammation of the brain" Nature (2003) 421:744-8.
De Beaucoudrey, et al., "Mutations in STAT3 and IL12RB1 impair the development of human IL-17-producing T cells" J Exp Med (2008) 205(7):1543-50.
De Rosa, et al., "11-color, 13-parameter flow cytometry: identification of human naive T cells by phenotype, function and T-cell receptor diversity" Nat Med (2001) 7(2):245-8.
Duhen, et al., "Production of interleukin 22 but not interleuking 17 by a subset of human skin-homing memory cells" Nat Immunol (2009) 10(8):857-63.
El Hed, et al., "Susceptibility of human Th17 cells to human immunodeficiency virus and their perturbation during infection" J. Infect Dis (2010) 201(6):843-54.
Evans, et al., "Optimal induction of T helper 17 cells in humans requires T cell receptor ligation in the context of Toll-like receptor-activated monocytes" Proc Natl Acad Sci USA (2007) 104(43):17034-9.
Eyerich, et al, Th22 cells represent a distinct human T cell subject involved in epidermal immunity and remodeling J Clin Invest (2009) 119(12):3573-85.
Fossiez, et al., "T cell interleukin-17 induces stromal cells to produce proinflammatory and hematopoietic cytokines" J Exp Med (1996) 183(6):2593-603.

(Continued)

*Primary Examiner* — Bridget E Bunner
*Assistant Examiner* — Fozia Hamud
(74) *Attorney, Agent, or Firm* — Klauber & Jackson LLC

(57) ABSTRACT

The present invention is directed to a method for promoting differentiation, activation and proliferation of human T helper lymphocytes such as those that express IL17 and IL22 (Th-IL17+ and Th-IL22+ T cells) and provides methods for decreasing T cell activation or T cell biological activity, inhibiting an immune response and treating autoimmune diseases by increasing the biological activity of or administering a transcription factor such as a Krüppel-like factor or a forkhead box factor, and pharmaceutical compositions effective for these methods. Also, the present invention provides methods for increasing T cell activation or T cell biological activity, stimulating an immune response and treating diseases such as cancers and infections by decreasing the biological activity of or administering an inhibitor of a transcription factor such as a Krüppel-like factor or a forkhead box factor and pharmaceutical compositions effective for these methods.

4 Claims, 20 Drawing Sheets

(56) References Cited

PUBLICATIONS

Fruman, "Phosphoinositide 3-kinase and its targets in B-cell and T-cell signaling" Curr Opin Immunol (2004) 16 (3):314-20.

Fujino, et al., "Increased expression of interleukin 17 in inflammatory bowel disease" Gut (2003) 52(1) 65-70.

Holland, et al., "STAT3 mutations in the hyper-IgE syndrome" N Engl J Med (2007) 357(16):1608-19.

Homey, et al., Up-regulation of macrophage inflammatory protein-3 alpha/CCL20 and CC chemokine receptor 6 in psoriasis J Immunol (2000) 164(12):6621-32.

Ivanov II, et al., "The orphan nuclear receptor RORgammat directs the differentiation program of proinflammatory IL-17+ T helper cells" Cell (2006) 126(6) 1121-33.

Kebir, et al., "Human TH17 lymphocytes promote blood-brain barrier disruption and central nervous system inflammation" Nat Med (2007) 13(10):1173-5.

Kerdiles, et al, "Foxo1 links homing and survival of naive T cells by regulating L-selectin, CCR7 and interleukin 7 receptor" Nat Immunol (2009) 10(2):176-84.

Korn, et al., "IL-21 initiates an alternative pathway to induce proinflammatory T(H)17 cells" Nature (2007) 448: 484-7.

Langrish, et al., "IL-23 drives a pathogenic T cell population that induces autoimmune inflammation" J Exp Med (2005) 201(2):233-40.

Laurence, et al., "T(H)-17 differentiation: of mice and men" Nat Immunol (2007) 8(9):903-5.

Lock, et al., "Gene-microarray analysis of multiple sclerosis lesions yields new targets validated in autoimmune encephalomyeliltis" Nat Med (2002) 8(5) 500-8.

Manel, et al., "The differentiation of human T(H)-17 cells requires transforming growth factor-beta and induction of the nuclear receptor RORgammat" Nat Immunol (2008) 9(6):641-9A.

Mangan, et al., "Transforming growth factor-beta induces development of the T(H)17 lineage" Nature (2006) 441:231-4.

Matusevicius, et al., "Interleukin-17 mRNA expression in blood and CSF mononuclear cells is augmented in multiple sclerosis" Mult Scler (1999) 5(2): 101-4.

McGeachy, et al., "TGF-beta and IL-6 drive the production of IL-17 and IL-10 by T cells and restrain T(H)-17 cell-mediated pathology" Nat Immunol (2007) 8(12):1390-7.

Minegishi, et al., "Dominant-negative mutations in the DNA-binding domain of STAT3 cause hyper-IgE syndrome" Nature (2007) 448:1058-62.

Nurieva, et al., "Essential autocrine regulation by IL-21 in the generation of inflammatory T cells" Nature (2007) 448:480-3.

Rochman, et al., "New insights into the regulation of T cells by gamma(c) family cytokines" Nat Rev Immunol (2009) 9(7):480-90.

Romagnani, et al., "Properties and origin of human Th17 cells" Mol Immunol (2009) 47(1):3-7.

Sinclair, et al., "Phosphatidylinositol-3-OH kinase and nutrient-sensing mTOR pathways control T lymphocyte trafficking" Nat Immunol (2008) 9(5):513-21.

Singh, et al., "Human T cells that are able to produce IL-17 express the chemokine receptor CCR6" J Immunol (2008) 180(1):214-21.

Stockinger, et al., "Differentiation and function of Th17 cells" Curr Opin Immunol (2007) 19(3):281-6.

Stockinger, et al., "Th17 cells: linking innate and adaptive immunity" Semin Immunol (2007) 19*6):353-61.

Tzartos, et al., "Interleukin-17 production in cental nervous system-infiltrating T cells and glial cells is associated with active disease in multiple sclerosis" Am J Pathol (2008) 172(1):146-55.

Van Beelen, et al., "Stimulation of the intracellular bacterial sensor NOD2 programs dendritic cells to promote interleukin-17 production in human memory T cells" Immunity (2007) 27(4):660-9.

Veldhoen, et al., "TGFbeta in the context of an inflammatory cytokine milieu supports de novo differentiation of IL-17-producing T cells" Immunity (2006) 24(2) 179-89.

Weaver, et al., "IL-17 family cytokines and the expanding diversity of effector T cell lineages" Annu Rev Immunol (2007) 25:821-52.

Weinreich, et al., "T cells expressing the transcription factor PLZF regulate the development of memory-like CD8+ T cells" Nat Immunol (2010) 11(8):709-16.

Weinreich, et al., "KLF2 transcription-factor deficiency in T cells results in unrestrained cytokine production and upregulation of bystandre chemokine receptors" Immunity (2009) 31(1):122-30.

Wilson, et al., "Development, cytokine profile and function of human interleukin 17-producing helper T cells" Nat Immunol (2007) 8(8):9507.

Wolk, et al., "Biology of interleukin-22" Semin Immunopathol (2010) 32(1):17-31.

Zheng, et al., "Interleukin-22, a T(H)17 cytokine, mediates IL-23-induced dermal inflammation and acanthosis" Nature (2007) 445:648-51.

Zhou, et al., "IL-6 programs T(H)-17 cell differentiation by promoting sequential engagement of the IL-21 and IL-23 pathways" Nat Immunol (2007) 8(9):967-74.

Zhou, et al., "Plasticity of CD4+ T cell lineage differentiation" Immunity (2009) 30(5):646-55.

\* cited by examiner

● EV   □ FOXO1

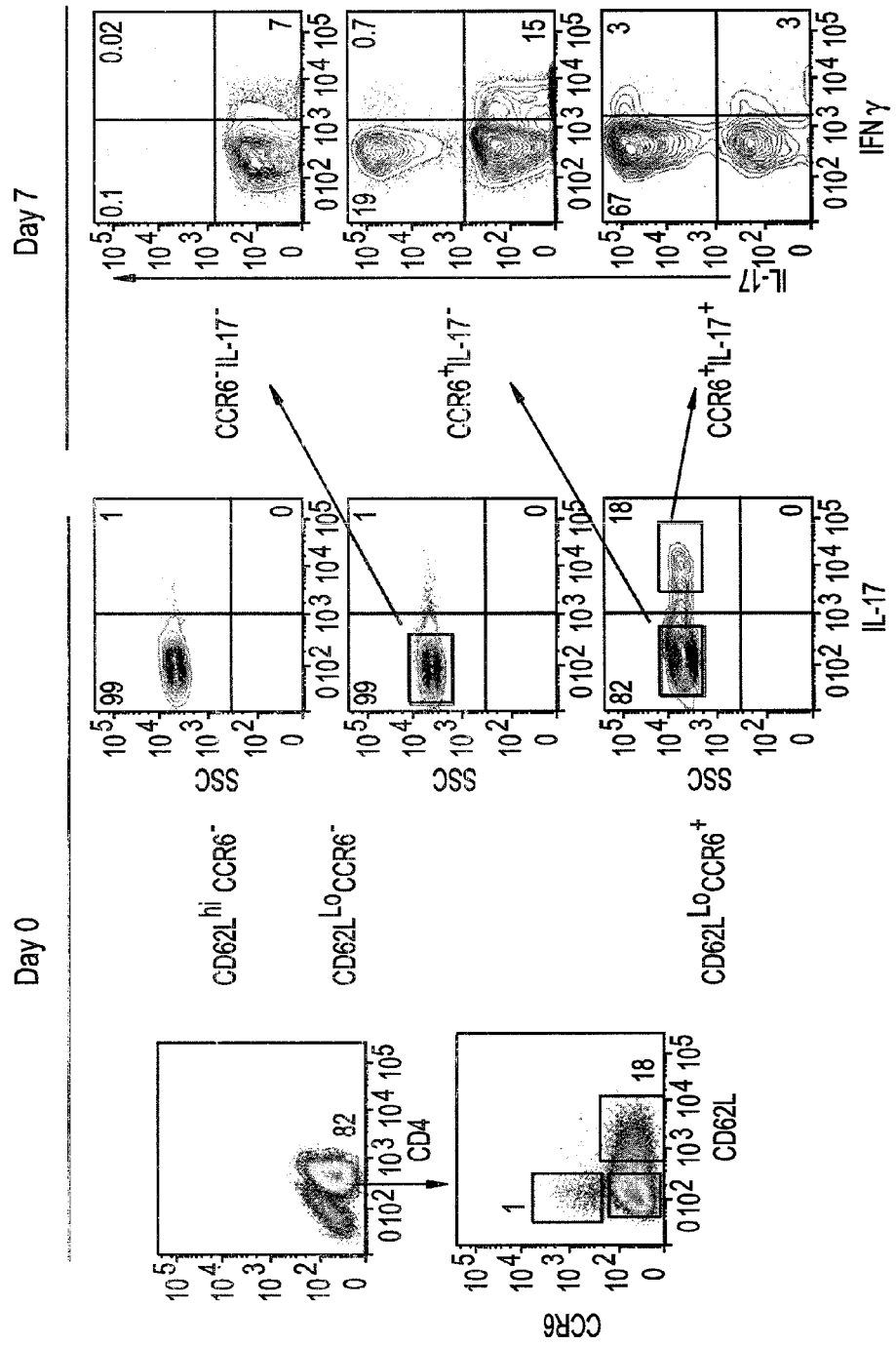

SEQUENCE LISTING

```
<160> NUMBER OF SEQ ID NOS: 5

<210> SEQ ID NO 1
<211> LENGTH: 33
<212> TYPE: DNA
<213> ORGANISM: Artificial Sequence
<220> FEATURE:
<223> OTHER INFORMATION: synthetic

<400> SEQUENCE: 1
ccggaattcg ccatggcgct gagtgaaccc atc                                33

<210> SEQ ID NO 2
<211> LENGTH: 33
<212> TYPE: DNA
<213> ORGANISM: Artificial Sequence
<220> FEATURE:
<223> OTHER INFORMATION: synthetic

<400> SEQUENCE: 2
ccggaattcc tacatgtgcc gtttcatgtg cag                                33

<210> SEQ ID NO 3
<211> LENGTH: 31
<212> TYPE: DNA
<213> ORGANISM: Artificial Sequence
<220> FEATURE:
<223> OTHER INFORMATION: synthetic

<400> SEQUENCE: 3
gctctagagc attgccatgg ccgaggcgcc t                                  31

<210> SEQ ID NO 4
<211> LENGTH: 28
<212> TYPE: DNA
<213> ORGANISM: Artificial Sequence
<220> FEATURE:
<223> OTHER INFORMATION: synthetic

<400> SEQUENCE: 4
ttctcgaggc ttacttgtac agctcgtc                                      28

<210> SEQ ID NO 5
<211> LENGTH: 21
<212> TYPE: DNA
<213> ORGANISM: Artificial Sequence
<220> FEATURE:
<223> OTHER INFORMATION: synthetic
<220> FEATURE:
<223> OTHER INFORMATION: the sequence is a combination of DNA and RNA

<400> SEQUENCE: 5
ggcaagacct acaccaagag t                                             21
```

METHODS FOR ACTIVATING T CELLS AND MODULATING AN IMMUNE RESPONSE

CROSS REFERENCE TO RELATED APPLICATIONS

This application claims the benefit of priority to U.S. Provisional Application No. 61/572,339, filed Jul. 14, 2011, the disclosure of which is herein incorporated by reference in its entirety.

FIELD OF THE INVENTION

The present invention pertains to the fields of cell culture, immunology, and T lymphocytes. More specifically, the invention relates to methods for promoting differentiation, function and activation of T cells such as human Th17+ and Th22+ cells and to methods of treating diseases by modulating function of T cells such as human Th17+ and Th22+ cells.

BACKGROUND OF THE INVENTION

T cells are a part of the adaptive immune system that scan the intracellular environment in order to target and destroy infected cells. Small peptide fragments, representing the entire cellular content, are transported to the cell surface as pMHCs, allowing T cell surface expressed antigen specific T cell receptors to scan for foreign signals. T cells interact with a large number of different cell types and recognize a diverse array of pathogens. There are distinct antigen recognition pathways which generate the appropriate T cell response. T cell activation can lead to a number of immune responses such as antibody production, activation of phagocytic cells and direct cell killing.

T helper cells (Th cells) are a subset of αβT-cells that usually express the CD4 co-receptor and have a major role in controlling and regulating the immune system by affecting other white blood cells. Th cells are vital to human immune responses because they orchestrate the immune system by controlling other T cell subsets, B cells and innate immune responses. The Th cell response is defined by two distinct pathways involving two different subtypes of Th cell, Th1 and Th2 cells. Th1 cells are largely targeted towards intravesicular pathogens such as bacteria and parasites via the activation of infected macrophages. Th2 cells largely invoke antibody production in B cells that neutralize extracellular pathogens and toxins. Th cell activation leads to the induction of a number of pathways that can result in B cell antibody production and immunoglobulin class switching, and macrophage action via both direct interaction and through the release of soluble factors.

Memory T cells are derived from normal T cells that have learned to remember the strategy used to defeat previous infections. Adaptive immunity is said to have memory because the immune system learns giving, for instance, life long immunity to infections such as mumps or chicken pox. T cells constitute a highly evolved arm of the adaptive immune system that is able to distinguish between pathogens and is capable of evolving or adapting during the lifetime of an individual such that immunity becomes better with each successive exposure to pathogen. Following infection, some of the activated T-cells become memory cells that remain in a state of readiness and have the ability to rapidly expand and fight recurrence of the same disease. That is, these cells learn from their experience of fighting a particular infection and so can use the most effective strategy to manage the same infection later.

Th17 cells, the T helper cells that produce IL-17 (also referred to as IL-17A) and other pro-inflammatory cytokines, have been shown to have key functions in a wide variety of autoimmune disease models in mice and are thought to be similarly involved in human disease (Weaver, et al., *Annual Review of Immunology* 2007; 25: 821-852; Bettelli, et al., *Current Opinion in Immunology* 2007; 19: 652-657; Stockinger, et al., *Current Opinion in Immunology* 2007; 19: 281-286). In healthy humans, IL-17-secreting cells are present in the CD45RO+CCR6+ populations of T cells from peripheral blood (Acosta-Rodriguez, et al., *Nature Immunology* 2007; 8: 639-646; Annunziato, et al., *J Exp Med* 2007; 204: 1849-1861) and gut (Annunziato, et al., *J Exp Med* 2007; 204: 1849-1861). Th17 cells or their products have been associated with the pathology of multiple inflammatory or autoimmune disorders in humans. IL-17 protein and Th17 CD4+ T cells are found in lesions from multiple sclerosis patients (Lock, et al., *Nat Med* 2002; 8, 500-508; Matusevicius, et al., *Mult Scler* 1999; 5; 101-104; Tzartos, et al., *Am J Pathol* 2008; 172: 146-155) where they are thought to contribute to the disruption of the blood-brain barrier (Kebir, et al., *Nat Med* 2007; 13: 1173-1175). IL-17 is produced by CD4+ T cells of rheumatoid synovium (Chabaud, et al., *Arthritis Rheum* 1999; 42: 963-970) and is thought to contribute to inflammation in rheumatoid arthritis (Attur, et al., *Arthritis Rheum* 1997; 40: 1050-1053; Fossiez, et al., *J Exp Med* 1996; 183: 2593-2603). In psoriasis, products associated with Th17 cells, including IL-17, IL-17F, IL-22, and CCR6 are induced (Homey, et al., *J Immunol* 2000; 164: 6621-6632; Zheng, et al., *Nature* 2007; 445: 648-651; Wilson, et al., *Nature Immunology* 2007; 8: 950-957). IL-17 is induced in the gut mucosa from Crohn's disease and ulcerative colitis patients and Th17 cells are detected (Homey, et al., *J Immunol* 2000; 164: 6621-6632; Annunziato, et al., *J Exp Med* 2007; 204: 1849-1861). IL-23, which is produced by dendritic cells in the intestine (Becker, et al., *The Journal of Clinical Investigation* 2003; 112: 693-706), contributes significantly to Th17 cell differentiation (McGeachy, et al., *Nature Immunology* 2007; 8: 1390-1397). Strikingly, polymorphisms in the IL23R gene are associated with Crohn's disease, further implicating the Th17 cell pathway in the pathogenesis of this disease (Duerr, et al., *Science* 2006; 314: 1461-1463).

The mechanisms leading to differentiation of Th17 cells have been well established in mice but they are still poorly understood in humans. In mice, differentiation of Th17 cells that secrete IL-17 and IL-17F requires the expression of the transcription factors Rorγt, an orphan nuclear hormone receptor, STAT3 and IRF4 (reviewed in Ivanov, I I, et al., *Semin Immunol* 2007). Rorγt is sufficient to direct expression of IL-17 in activated mouse T cells (Ivanov, I I, et al. *Cell* 2006; 126: 1121-1133) and is thus considered to be the effector transcription factor that establishes the Th17 differentiation lineage. Conditions that induce Th17 cell differentiation from naive murine T cells, including expression of Rorγt, have been established. Combinations of TGF-β and IL-6 (Veldhoen, et al., *Immunity* 2006; 24: 179-189; Bettelli, et al., *Nature* 2006; 441: 235-238; Mangan, et al., *Nature* 2006; 441: 231-234) or TGF-β and IL-21 (Korn, et al., *Nature* 2007; 448: 484-487; Nurieva, et al., *Nature* 2007; 448: 480-483; Zhou, et al., *Nature Immunology* 2007; 8: 967-974) are sufficient to initiate IL-17 and IL-17F expression. Expression of IL-22, considered to be another Th17 cytokine, is induced by IL-6 and inhibited by high concentrations of TGF-β (Zheng, et al., *Nature* 2007; 445: 648-651). IL-23 is required in vivo for the generation of pathogenic Th17 cells, but it is not required in vitro for the induction of IL-17, IL-17F or IL-22 (McGeachy, et al., *Nature Immunology* 2007; 8: 1390-1397).

In contrast to murine T cells, human T cells with a naive surface phenotype fail to produce IL-17 in the presence of TGF-β and IL-6 (Chen, et al., *Arthritis Rheum* 2007; 56: 2936-2946; Acosta-Rodriguez, et al., *Nature Immunology* 2007; 8: 942-949; van Beelen, et al., *Immunity* 2007; 27: 660-669; Evans, et al., *Proc Natl Acad Sci USA* 2007; 104: 17034-17039). Increased expression of IL-17 was, however, observed by some groups in response to IL-1 alone (Acosta-Rodriguez, et al., *Nature Immunology* 2007; 8: 942-949) or with IL-23 (Wilson, et al., *Nature Immunology* 2007; 8: 950-957). Others have failed to observe such a response (van Beelen, et al., *Immunity* 2007; 27: 660-669). These disparate findings reveal that the identities of the exogenous factors required to induce the differentiation of human Th17 cells remain unknown. The difference between the requirements for mouse and human Th17 cell differentiation have been ascribed to divergent differentiation processes, although it remains possible that T cells purified from adult peripheral blood on the basis of CD45RA expression alone are not equivalent to naive murine T cells (Stockinger, et al., *Semin Immunol* 2007; De Rosa, et al., *Nat Med* 2001; 7: 245-248; Laurence, et al., *Nature Immunology* 2007; 8: 903-905).

In addition to Th1 and Th2 cells, it is now accepted that naïve CD4$^+$ T cells can differentiate into Th17 or Th22 cells that secrete IL-17 or IL-22, respectively (Annunziato, et al., *Arthritis Res Ther* 2009; 11: 257; Wolk, et al., *Semin Immunopathol* 2010; 32: 17-31; Zhou, et al., *Immunity* 2009; 30: 646-655). Th17 cells mediate pro-inflammatory immune responses against some species of extracellular bacteria and most fungal pathogens (Bettelli, et al., *Nature* 2006; 441: 235-238; de Beaucoudrey, et al., *J Exp Med* 2008; 205: 1543-1550; Holland, et al. n *Engl J Med* 2007; 357: 1608-1619; Minegishi, et al., *Nature* 2007; 448: 1058-1062). Th17 cells are also broadly implicated in the pathogenesis of many common autoimmune disorders, including multiple sclerosis, rheumatoid arthritis, psoriasis, and inflammatory bowel disease (Cua, et al., *Nature* 2003; 421: 744-748; Fujino, et al., *Gut* 2003; 52: 65-70; Langrish, et al., *J Exp Med* 2005; 201: 233-240; Lock, et al., *Nature Medicine* 2002; 8: 500-508; Wilson, et al., *Nature Immunology* 2007; 8: 950-957). Th22 cells are involved in skin immunity and remodeling, but are also implicated in cutaneous inflammatory conditions such as psoriasis (Eyerich, et al., *The Journal of Clinical Investigation* 2009; 119: 3573-3585; Wolk, et al., *Semin Immunopathol* 2010; 32: 17-31). Ex vivo analyses of human peripheral blood T cells indicate that nearly all IL-17-secreting cells, and the majority of IL-22-producing T cells, express the chemokine receptor CCR6 and the transcription factor RORC (Annunziato, et al., *J Exp Med* 2007; 204: 1849-1861; Duhen, et al., *Nature Immunology* 2009; 10: 857-863; El Hed, et al., *J Infect Dis* 2010; 201: 843-854; Romagnani, et al., *Mol Immunol* 2009; 47: 3-7; Singh, et al., *J Immunol* 2008; 180: 214-221). Accordingly, ectopic expression of RORC in naïve T cells or CCR6$^-$ memory cells is sufficient to induce IL-17 secretion (Manel, et al., *Nature Immunology* 2008; 9: 641-649). Currently, all effector T cell subsets, including Th17 and Th22 cells, are defined solely based on cytokine expression following ex vivo stimulation (Duhen, et al., *Nature Immunology* 2009). However, it is not clear whether this definition accurately reflects the full repertoire of memory T cells that have the capacity to produce IL-17/IL-22 at sites of inflammation. Moreover, the cytokines and downstream signaling pathways that control IL-17/IL-22 secretion in lineage-committed memory T cells remain uncharacterized.

The IL-2 family of cytokines, which signal through multimeric receptors containing the shared common gamma chain (γc) subunit, includes IL-2, IL-4, IL-7 IL-9, IL-15, and IL-21. These cytokines, particularly IL-2, IL-7, and IL-15, play pivotal roles in promoting T cell development, homeostasis, and differentiation. In addition to activating Jak/Stat pathways, γc-signaling induces the generation of lipid second messengers through activation of PI-3K (Rochman, et al., *Nature Reviews* 2009; 9: 480-490). One of these second messengers, phosphatidylinositol-(3,4,5)-trisphosphate (PI(3,4,5)P$_3$), binds to the pleckstrin homology (PH) domain of proteins and controls the activity and function of a number of signaling molecules, including the serine/threonine protein kinase Akt (Fruman, *Current Opinion in Immunology* 2004; 16: 314-320). In turn, Akt directly phosphorylates the transcription factor Forkhead box protein O1 (FOXO1), thereby preventing its nuclear translocation and transcriptional activity (Brunet, et al., *Cell* 1999; 96: 857-868) Inhibition of FOXO1 by PI-3K has been shown to be essential for γc-cytokine signaling-mediated cell survival, proliferation and glucose utilization in leukemia cells (Barata, et al., *J Exp Med* 2004; 200: 659-669). In contrast, activation of FOXO1, by way of reduced PI-3K signaling, can lead to the expression of another transcription factor called kruppel-like factor 2 (KLF2) (Kerdiles, et al., *Nature Immunology* 2009; 10: 176-184; Sinclair, et al., *Nature Immunology* 2008; 9: 513-521), which has been implicated in the modulation of IFNγ and IL-4 production in human and mouse T cells (Bu, et al., *J Clin Invest* 2010; 120: 1961-1970; Weinreich, et al., *Nature Immunology* 2010; 11: 709-716; Weinreich, et al., *Immunity* 2009; 31: 122-130). However, whether FOXO1 or KLF2 act downstream of PI-3K to regulate effector cytokine production in human memory T cells is not yet known.

Common gamma chain utilizing cytokines, γc-cytokines, notably IL-2, IL-7 or IL-15, are sufficient to induce de novo expression of IL-17, IL-22, and other Th17-signature cytokines in CCR6$^+$, but not CCR6$^-$, T$_M$ cells. Treatment of cytokine-stimulated CCR6$^+$ T$_M$ cells with small molecule inhibitors of PI-3K or Akt repressed γc-cytokine-driven IL-17/IL-22 expression, as did ectopic expression of FOXO1 or KLF2. These findings suggest that PI-3K signaling may amplify Th17-/Th22-associated tissue inflammation by promoting pro-inflammatory cytokine expression in lineage-committed human Th17/Th22 cells. Our results also demonstrate that the frequency of human memory T cells harboring the capacity to secrete IL-17/IL-22 in vivo may be substantially higher than what is predicted based on ex vivo cytokine analysis.

Phosphatidylinositol 3-kinases (PI 3-kinases or PI-3Ks) are a family of enzymes involved in cellular functions such as cell growth, proliferation, differentiation, motility, survival and intracellular trafficking, which in turn are involved in cancer. PI-3Ks are a family of related intracellular signal transducer enzymes capable of phosphorylating the 3 position hydroxyl group of the inositol ring of phosphatidylinositol (PtdIns). The pathway, with oncogene PIK3CA and tumor suppressor PTEN (gene), is implicated in insensitivity of cancer tumors to insulin and IGF1, in calorie restriction.

PI-3Ks interact with the IRS (Insulin receptor substrate) in order to regulate glucose uptake through a series of phosphorylation events. Discrete members of PI-3K family are activated in immune system depending on the type of cell and/or receptor. (Koyasu, Nature Review, 2003; the role of PI3K in immune system). The phosphoinositol-3-kinase family is divided into three different classes: Class I, Class II, and Class III. The classifications are based on primary structure, regulation, and in vitro lipid substrate specificity.

Class I PI-3Ks are responsible for the production of Phosphatidylinositol 3-phosphate (PI(3)P), Phosphatidylinositol (3,4)-bisphosphate (PI(3,4)P$_2$), and Phosphatidylinositol (3,4,5)-trisphosphate (PI(3,4,5)P$_3$. The PI-3K is activated by G protein-coupled receptors and tyrosine kinase receptors. Class I PI-3K are heterodimeric molecules composed of a regulatory and a catalytic subunit; they are further divided between IA and IB subsets based on sequence similarity. Class IA PI-3K is composed of a heterodimer between a p110 catalytic subunit and a p85 regulatory subunit. There are five variants of the p85 regulatory subunit, designated p85α, p55α, p50α, p85β, or p55γ. There are also three variants of the p110 catalytic subunit designated p110α, β, or δ. The first three regulatory subunits are all splice variants of the same gene (Pik3r1), the other two being expressed by other genes (Pik3r2 and Pik3r3, p85β, and p55γ, respectively). The most highly expressed regulatory subunit is p85α; all three catalytic subunits are expressed by separate genes (Pik3ca, Pik3cb, and Pik3cd for p110α, p110β, and p110δ, respectively). The first two p110 isoforms (α and β) are expressed in all cells, but p110δ is expressed primarily in leukocytes, and it has been suggested that it evolved in parallel with the adaptive immune system. The regulatory p101 and catalytic p110γ subunits comprise the type IB PI-3K and are encoded by a single gene each.

The majority of the research on PI 3-kinases has focused on the Class I PI 3-kinases. Class I PI 3-kinases are composed of a catalytic subunit known as p110 and a regulatory subunit related to either p85 or p101. The p85 subunits contain SH2 and SH3 domains (Online 'Mendelian Inheritance in Man' (OMIM) 171833). The SH2 domains bind preferentially to phosphorylated tyrosine residues in the amino acid sequence context Y-X-X-M.

Class II and III PI-3K are differentiated from the Class I by their structure and function. Class II comprises three catalytic isoforms (C2α, C2β, and C2γ), but, unlike Classes I and III, no regulatory proteins. Class II catalyse the production of PI(3)P and PI(3,4)P$_2$ from PI; however, little is known about their role in immune cells. C2α and C2β are expressed through the body, however expression of C2γ is limited to hepatocytes. The distinct feature of Class II PI-3Ks is the C-terminal C2 domain. This domain lacks critical Asp residues to coordinate binding of Ca$^{2+}$, which suggests class II PI-3Ks bind lipids in a Ca$^{2+}$-independent manner.

Class III produces only PI(3)P from PI but are more similar to Class I in structure, as they exist as a heterodimers of a catalytic (Vps34) and a regulatory (Vps15/p150) subunits. Class III seems to be primarily involved in the trafficking of proteins and vesicles. There is, however, evidence to show that they are able to contribute to the effectiveness of several process important to immune cells, not least phagocytosis.

The various 3-phosphorylated phosphoinositides that are produced by PI 3-kinases (PtdIns3P, PtdIns(3,4)P2, PtdIns(3,5)P2, and PtdIns(3,4,5)P3) function in a mechanism by which an assorted group of signalling proteins, containing PX domain, pleckstrin homology domains (PH domains), FYVE domains and other phosphoinositide-binding domains, are recruited to various cellular membranes.

PI 3-kinases have been linked to an extraordinarily diverse group of cellular functions, including cell growth, proliferation, differentiation, motility, survival and intracellular trafficking Many of these functions relate to the ability of class I PI 3-kinases to activate protein kinase B (PKB, aka Akt) as in the PI-3K/AKT/mTOR pathway. The p110δ and p110γ isoforms regulate different aspects of immune responses. PI 3-kinases are also a key component of the insulin signaling pathway. Hence there is great interest in the role of PI 3-kinase signaling in Diabetes mellitus.

The pleckstrin homology domain of AKT binds directly to PtdIns(3,4,5)P3 and PtdIns(3,4)P2, which are produced by activated PI 3-kinase.ince PtdIns(3,4,5)P3 and PtdIns(3,4)P2 are restricted to the plasma membrane, this results in translocation of AKT to the plasma membrane. Likewise, the phosphoinositide-dependent protein kinase 1 (PDK1 or, rarely referred to as PDPK1) also contains a pleckstrin homology domain that binds directly to PtdIns(3,4,5)P3 and PtdIns(3,4)P2, causing it to also translocate to the plasma membrane upon activation of PI 3-kinase. The colocalization of activated PDK1 and AKT allows AKT to become phosphorylated by PDK1 on threonine 308, leading to partial activation of AKT. Full activation of AKT occurs upon phosphorylation of serine 473 by the TORC2 complex of the mTOR protein kinase. (The nomenclature can be confusing. Note that PDK1 also refers to the unrelated enzyme Pyruvate dehydrogenase kinase, isozyme 1. Similarly, TORC2 also refers to the unrelated transcription factor Transducer of Regulated CREB activity 2, which has recently been renamed CREB-regulated transcription coactivator 2 (CRTC2) to reduce the confusion). The "PI3-k/AKT" signaling pathway has been shown to be required for an extremely diverse array of cellular activities—most notably cellular proliferation and survival.

Many other proteins have been identified that are regulated by PtdIns(3,4,5)P3, including Bruton's Tyrosine Kinase (BTK), General Receptor for Phosphoinositides-1 (GRP1), and the O-linked N-acetylglucosamine (O-GlcNAc) transferase.

The class IA PI 3-kinase p110α is mutated in many cancers. Many of these mutations cause the kinase to be more active. The PtdIns(3,4,5)P$_3$ phosphatase PTEN that antagonises PI 3-kinase signaling is absent from many tumours. Hence, PI 3-kinase activity contributes significantly to cellular transformation and the development of cancer.

PI-3K has also been implicated in Long-term potentiation (LTP). Whether it is required for the expression or the induction of LTP is still debated. In mouse hippocampal CA1 neurons, PI-3K is complexed with AMPA Receptors and compartmentalized at the postsynaptic density of glutamatergic synapses. PI-3K is phosphorylated upon NMDA Receptor-dependent CaMKII activity, and it then facilitates the insertion of AMPA-R GluR1 subunits into the plasma membrane. This suggests that PI-3K is required for the expression of LTP. Furthermore, PI-3K inhibitors abolished the expression of LTP in rat hippocampal CA1, but do not affect its induction. Notably, the dependence of late-phase LTP expression on PI-3K seems to decrease over time.

However, another study found that PI-3K inhibitors suppressed the induction, but not the expression, of LTP in mouse hippocampal CA1. The PI-3K pathway also recruits many other proteins downstream, including mTOR, GSK3β, and PSD-95. The PI-3K-mTOR pathway leads to the phosphorylation of p70S6K, a kinase that facilitates translational activity further suggesting that PI-3K is required for the protein-synthesis phase of LTP induction instead.

Many of the PI 3-kinases appear to have a serine/threonine kinase activity in vitro; however, it is unclear whether this has any role in vivo.

In addition to the class I-class III PI 3-kinases there is a group of more distantly related enzymes that are sometimes referred to as class IV PI 3-kinases. The class IV PI 3-kinases family is composed of ataxia telangiectasia mutated (ATM), ataxia telangiectasia and Rad3 related (ATR), DNA-dependent protein kinase (DNA-PK) and mammalian Target Of Rapamycin (mTOR). These members of the PI 3-kinase superfamily are protein serine/threonine kinases.

All PI 3-kinases are inhibited by the drugs wortmannin and LY294002, although certain members of the class II PI 3-kinase family show decreased sensitivity. As wortmannin and LY294002 are broad inhibitors against PI 3-kinases and a number of unrelated proteins at higher concentrations they are too toxic to be used as therapeutics. A number of pharmaceutical companies have recently been working on PI 3-kinase isoform specific inhibitors including the class I PI 3-kinase, p110δ isoform specific inhibitors, IC486068 and IC87114, ICOS Corporation.

FOX (Forkhead box) proteins are a family of transcription factors that play important roles in regulating the expression of genes involved in cell growth, proliferation, differentiation, and longevity. Many FOX proteins are important to embryonic development. The defining feature of FOX proteins is the forkhead box, a sequence of 80 to 100 amino acids forming a motif that binds to DNA. This forkhead motif is also known as the winged helix due to the butterfly-like appearance of the loops in the protein structure of the domain. Forkhead genes are a subgroup of the helix-turn-helix class of proteins. Many other genes encoding FOX proteins have been identified. For example, the FOXF2 gene encodes forkhead box F2, one of many human homologues of the *Drosophila melanogaster* transcription factor forkhead. FOXF2 is expressed in lung and placenta. Some FOX genes are downstream targets of the hedgehog signaling pathway, which plays a role in the development of basal cell carcinomas. Members of the class O regulate metabolism, cellular proliferation, stress tolerance and possibly lifespan. The activity of FoxO is controlled by post-translational modifications, including phosphorylation, acetylation and ubiquitination.

The Sp/KLF family (specificity protein/Krüppel-like factor) is a family of transcription factors, including the Kruppel-like factors as well as Sp1, Sp2, Sp3, Sp4, Sp8, Sp9; and possibly Sp5 and Sp7. KLF14 is also designated Sp6. The Krüppel-like family of transcription factors (Klfs), have been extensively studied for their roles in cell proliferation, differentiation and survival, especially in the context of cancer. All KLF family members are characterized by their three Cys2 His2 zinc fingers located at the C-terminus separated by a highly conserved H/C link. DNA binding studies demonstrated that the KLFs have similar affinities for different GC-rich sites, or sites with CACCC homology, and can compete with each other for the occupation of such sites. KLFs also share a high degree of homology between the specificity protein (Sp) family of zinc-finger transcription factors and bind similar, if not the same sites, in a large number of genes. The following human genes encode Kruppel-like factors: KLF1, KLF2, KLF3, KLF4, KLF5, KLF6, KLF7, KLF8, KLF9, KLF10, KLF11, KLF12, KLF13, KLF14, KLF15, KLF16, and KLF17.

SUMMARY OF INVENTION

In a first aspect, the present invention is directed to a method for promoting activation, function or proliferation of T helper lymphocytes by:
a) isolating a population of T cells from a subject; and
b) incubating the population of T cells in a medium that contains one or more cytokine.

In some embodiments, the incubating may be performed in vitro, and it may be performed in a serum free medium. The incubating may promote activation, function or proliferation of human T cells such as Th-IL17+ or Th-IL22+ (Th17+ or Th22+) cells. Detecting an increase in expression of any cellular marker of human Th17+ or Th22+ differentiation, activation or proliferation, such as IL17, IL17F, IL23R, RORC or IL26, after incubating in human Th-IL17+ or Th-IL22+ promoting conditions may be used as a positive indicator of Th-IL17+ or Th-IL22+ cell function or activation. In some embodiments, the T helper lymphocytes may express IL17 or IL22 (T17+ or T22+ cells), and they may be human. In some embodiments, the T cells may be memory T cells ($T_M$) such as, for example, CCR6$^+$ CD45RO$^+$ memory T cells ($T_M$). Also, in some embodiments, the one or more cytokine may be, for instance, one or more of IL-2, IL-7 and IL-15. In some embodiments, the subject is a human.

In some embodiments, the T cells such as CCR6$^+$ or CD45RO+ $T_M$ cells, used in the present methods may be isolated from cord blood, buffy coats of adult humans, cell cultures comprising cells that express CD34 (CD34+ cells), or human embryonic stem cells. CD34+ cells may be isolated from fetal liver, cord blood, or mobilized adult blood and further expanded in vitro to generate cell cultures comprising CD34+ cells. In some embodiments, the concentration of one or more cytokine such as, for instance, one or more of IL-2, IL-7 or IL-15 in the serum-free culture medium is at least 0.1 ng/ml, at least 0.5 ng/ml, 1.0 ng/ml, 2.0 ng/ml, 3.0 ng/ml, 5.0 ng/ml, 10 ng/ml, 15.0 ng/ml, 20 ng/ml, 30 ng/ml, 50.0 ng/ml or more. In some embodiments, one of IL-2, IL-7 or IL-15 is present in the serum-free culture medium, in some embodiments two of IL-2, IL-7 or IL-15 are present in the serum-free culture medium, and in some embodiments three of IL-2, IL-7 or IL-15 are present in the serum-free culture medium.

In some embodiments of the methods, the incubating step is performed for at least 2 hours, 4 hours, 6 hours, 10 hours, 12 hours, one day, two days, three days, four days, five days, six days, eight days, ten days or more. The methods of the present invention may further comprise an enrichment step, whereby post-incubation cells (i.e., cells that have been incubated in accordance with the invention) are selected for expression of a cell surface marker or cell surface antigen expressed on human T cells such as Th-IL17+ or Th-IL22+ cells. For instance, the cell surface marker or cell surface antigen expressed on human Th-IL17+ or Th-IL22+ cells may be one or more of CCR6, CCR5, CXCR3 or CD161. The methods may result in activation or proliferation or increased function of T helper lymphocytes of at least about 10%, 25%, 50%, 75%, or two fold, three fold, four fold, five fold, six fold, eight fold or ten fold or more as measured by an increase in the numbers of T helper cells expressing a particular cytokine before the method is performed or in the amount of a particular cytokine expressed by a group or population of T helper cells before the method is performed.

In a second aspect, the invention is directed to a method for generating or expanding an activated population of T helper lymphocytes by
a) isolating a population of T cells from a subject; and
b) incubating the population of T cells in a medium that contains one or more cytokine.

In some embodiments, the incubating may be performed in vitro, and it may be performed in a serum free medium. The incubating may promote activation, function or proliferation of human T cells such as Th-IL17+ or Th-IL22+ (T17+ or T22+) cells. Detecting an increase in expression of any cellular marker of human Th-IL17+ or Th-IL22+ function or activation, such as IL17, IL17F, IL23R, RORC or IL26, after incubating in human Th-IL17+ or ThIL22+ promoting conditions may be used as a positive indicator of Th-IL17+ or Th-IL22+ cell activation, proliferation or function. In some embodiments, the T helper lymphocytes may express IL17 or IL22 (T17+ or T22+ cells), and they may be human. In some embodiments, the T cells may be memory T cells ($T_M$) such as, for example, CCR6$^+$ CD45RO$^+$ memory T cells ($T_M$). Also, in some embodiments, the one or more cytokine may be, for instance, one or more of IL-2, IL-7 and IL-15. In some embodiments, the subject is a human.

In some embodiments, the T cells such as CCR6+ or CD45RO+ T$_M$ cells, used in the present methods may be isolated from cord blood, buffy coats of adult humans, cell cultures comprising cells that express CD34 (CD34+ cells), or human embryonic stem cells. CD34+ cells may be isolated from fetal liver, cord blood, or mobilized adult blood and further expanded in vitro to generate cell cultures comprising CD34+ cells. In some embodiments, the concentration of one or more cytokine such as, for instance, one or more of IL-2, IL-7 or IL-15 in the serum-free culture medium is at least 0.1 ng/ml, at least 0.5 ng/ml, 1.0 ng/ml, 2.0 ng/ml, 3.0 ng/ml, 5.0 ng/ml, 10 ng/ml, 15.0 ng/ml, 20 ng/ml, 30 ng/ml, 50.0 ng/ml or more. In some embodiments, one of IL-2, IL-7 or IL-15 is present in the serum-free culture medium, in some embodiments two of IL-2, IL-7 or IL-15 are present in the serum-free culture medium, and in some embodiments three of IL-2, IL-7 or IL-15 are present in the serum-free culture medium.

In some embodiments of the methods, the incubating step is performed for at least 2 hours, 4 hours, 6 hours, 10 hours, 12 hours, one day, two days, three days, four days, five days, six days, eight days, ten days or more. The methods of the present invention may further comprise an enrichment step, whereby post-incubation cells (i.e., cells that have been incubated in accordance with the invention) are selected for expression of a cell surface marker or cell surface antigen expressed on human T cells such as Th-IL17+ or Th-IL22+ cells. For instance, the cell surface marker or cell surface antigen expressed on human Th-IL17+ or Th-IL22+ cells may be one or more of CCR6, CCR5, CXCR3 or CD161. The methods may result in activation or proliferation or increased function of T helper lymphocytes of at least about 10%, 25%, 50%, 75%, or two fold, three fold, four fold, five fold, six fold, eight fold or ten fold or more as measured by an increase in the numbers of T helper cells expressing a particular cytokine before the method is performed or in the amount of a particular cytokine expressed by a group or population of T helper cells before the method is performed.

The present invention is also based in part upon the discovery that signaling components of a phosphoinositide 3-kinase pathway, for example two transcription factors, namely KLF2 and FOXO1, are important in regulating or suppressing Th17 cell function. Therefore, compounds targeting the PI-3 kinase pathway, for example targeting these transcription factors, or modifiers of PI-3 kinase pathway may be used to treat autoimmune or inflammatory diseases.

In a third aspect, the present invention provides methods for decreasing T cell activation or T cell biological activity by decreasing the biological activity or expression of a phosphoinositide 3-kinase (PI-3K) or a biologically active fragment or analog thereof, by inhibiting or decreasing activity of a phosphoinositide 3-kinase PI-3K/Akt biological pathway or by increasing the biological activity of or administering a transcription factor, such as, for instance, a Krüppel-like factor, for example KLF2, or a forkhead box factor, for example FOXO1, or a biologically active fragment or analog thereof. In some instances, the methods may be effected by administering an agent that inhibits expression of or biological activity of a phosphoinositide 3-kinase (PI-3K), or an agent that increases expression of or biological activity of a Krüppel-like factor such as KLF2 or a forkhead box factor such as FOXO1. In some embodiments, such agents are, for instance, a small molecule, an antibody, a DNA or RNA, or a genetic construct, such as might be administered by standard gene therapy techniques. In some instances, the methods are performed by administering a KLF2 or a FOXO1 or a biologically active fragment or analog thereof. In some instances, the T cells are helper T cells, such as, for instance, Th17+ or Th22+ cells. In some instances, the activation of T cells such as Th17+ or Th22+ cells or the T cell biological activity of such T cells may be decreased by about 5%, 10%, 20%, 30%, 40%, 50%, 60%, 75%, 80%, 90%, 95% or more, or the biological activity or expression of a phosphoinositide 3-kinase (PI-3K) or the activity of a phosphoinositide 3-kinase (PI-3K)/Akt biological pathway may be decreased by about 5%, 10%, 20%, 30%, 40%, 50%, 60%, 75%, 80%, 90%, 95% or more. In other instances, the biological activity of or amount of a transcription factor, such as, for instance, KLF2 or FOXO1 may be increased by about 5%, 10%, 20%, 30%, 40%, 50%, 60%, 75%, 80%, 90%, 95% or more.

In a fourth aspect, the present invention provides methods for increasing T cell activation or T cell biological activity by increasing the biological activity or expression of a phosphoinositide 3-kinase (PI-3K) or a biologically active fragment or analog thereof, by stimulating or increasing activity of a phosphoinositide 3-kinase (PI-3K)/Akt biological pathway or by inhibiting activity of an enzyme such as a transcription factor, for instance, a Krüppel-like factor such as KLF2 or a forkhead box factor such as FOXO1, or a biologically active fragment or analog thereof. In some instances, the methods may be effected by administering an agent that increases expression of or biological activity of a phosphoinositide 3-kinase (PI-3K). In other instances, the methods may be effected by administering an agent that decreases expression of or biological activity of a Krüppel-like factor such as KLF2 or a forkhead box factor such as FOXO1, or a biologically active fragment or analog thereof. The agent may be, for instance, a small molecule, an antibody, a DNA or RNA, or a genetic construct, such as might be administered by standard gene therapy techniques. In some instances, the methods are performed by administering an inhibitor such as an antibody to a KLF2 or a FOXO1 or a biologically active fragment or analog thereof. In some instances, the T cells are helper T cells, such as, for instance, Th17+ or Th22+ cells. In some instances, the activation of T cells such as T17+ or T22+ cells or the T cell biological activity may be increased by about 5%, 10%, 20%, 30%, 40%, 50%, 60%, 75%, 80%, 90%, 95% or more. Likewise, in some instances, the biological activity or expression of a phosphoinositide 3-kinase (PI-3K), the activity of a phosphoinositide 3-kinase (PI-3K)/Akt biological pathway may be increased by about 5%, 10%, 20%, 30%, 40%, 50%, 60%, 75%, 80%, 90%, 95% or more. Similarly, in other instances, biological activity or expression of a Krüppel-like factor such as KLF2 or a forkhead box factor such as FOXO1, or a biologically active fragment or analog thereof, may be decreased by about 5%, 10%, 20%, 30%, 40%, 50%, 60%, 75%, 80%, 90%, 95% or more.

In a fifth aspect, the present invention provides methods for inhibiting an immune response. The methods for inhibiting an immune response may feature decreasing the biological activity or expression of a phosphoinositide 3-kinase (PI-3K) or a biologically active fragment or analog thereof, by inhibiting or decreasing activity of a phosphoinositide 3-kinase PI-3K/Akt biological pathway or by increasing the biological activity of or administering a transcription factor, such as, for instance, a Krüppel-like factor, for example KLF2, or a forkhead box factor, for example FOXO1, or a biologically active fragment or analog thereof. In some instances, the methods may be effected by administering an agent that inhibits expression of or biological activity of a phosphoinositide 3-kinase (PI-3K), or an agent that increases expression of or biological activity of a Krüppel-like factor such as KLF2 or a forkhead box factor such as FOXO1. In some embodiments, such agents are, for instance, a small molecule, an antibody, a DNA or RNA, or a genetic construct, such as might be administered by standard gene therapy techniques. In some instances, the methods are performed by administering a KLF2 or a FOXO1 or a biologically active fragment or analog thereof. In some instances, the T cells are helper T cells, such as, for instance, Th17+ or Th22+ cells. In some instances, the activation of T cells such as Th17+ or Th22+ cells or the T cell biological activity of such T cells may be decreased by about 5%, 10%, 20%, 30%, 40%, 50%, 60%, 75%, 80%, 90%, 95% or more, or the biological activity or expression of a phosphoinositide 3-kinase (PI-3K) or the activity of a phosphoinositide 3-kinase (PI-3K)/Akt biological pathway may be decreased by about 5%, 10%, 20%, 30%, 40%, 50%, 60%, 75%, 80%, 90%, 95% or more. In other instances, the biological activity of or amount of a transcription factor, such as, for instance, KLF2 or FOXO1 may be increased by about 5%, 10%, 20%, 30%, 40%, 50%, 60%, 75%, 80%, 90%, 95% or more.

In a sixth aspect, the present invention provides methods for stimulating an immune response. The methods for stimulating an immune response may feature increasing the biological activity or expression of a phosphoinositide 3-kinase (PI-3K) or a biologically active fragment or analog thereof, by stimulating or increasing activity of a phosphoinositide 3-kinase (PI-3K)/Akt biological pathway or by inhibiting activity of an enzyme such as a transcription factor, for instance, a Krüppel-like factor such as KLF2 or a forkhead box factor such as FOXO1, or a biologically active fragment or analog thereof. In some instances, the methods may be effected by administering an agent that increases expression of or biological activity of a phosphoinositide 3-kinase (PI-3K). In other instances, the methods may be effected by administering an agent that decreases expression of or biological activity of a Krüppel-like factor such as KLF2 or a forkhead box factor such as FOXO1, or a biologically active fragment or analog thereof. The agent may be, for instance, a small molecule, an antibody, a DNA or RNA, or a genetic construct, such as might be administered by standard gene therapy techniques. In some instances, the methods are performed by administering an inhibitor such as an antibody to a KLF2 or a FOXO1 or a biologically active fragment or analog thereof. In some instances, the T cells are helper T cells, such as, for instance, Th17+ or Th22+ cells. In some instances, the activation of T cells such as T17+ or T22+ cells or the T cell biological activity may be increased by about 5%, 10%, 20%, 30%, 40%, 50%, 60%, 75%, 80%, 90%, 95% or more. Likewise, in some instances, the biological activity or expression of a phosphoinositide 3-kinase (PI-3K), the activity of a phosphoinositide 3-kinase (PI-3K)/Akt biological pathway may be increased by about 5%, 10%, 20%, 30%, 40%, 50%, 60%, 75%, 80%, 90%, 95% or more. Similarly, in other instances, biological activity or expression of a Krüppel-like factor such as KLF2 or a forkhead box factor such as FOXO1, or a biologically active fragment or analog thereof, may be decreased by about 5%, 10%, 20%, 30%, 40%, 50%, 60%, 75%, 80%, 90%, 95% or more.

In an seventh aspect, the present invention provides methods to identify agents such as small molecules, proteins and antibodies that may inhibit an immune response or that may decrease or downregulate a T cell such as Th17+ or Th22+ cell activity or activation. The invention identifies a novel target that can be manipulated to regulate an immune response. Agents such as small molecules, proteins and antibodies that may inhibit an immune response or that may decrease or downregulate T cell such as Th17+ or Th22+ cell activity or activation, may be identified by standard assay techniques known in the art as applied to identify those agents that decrease the biological activity or expression of a phosphoinositide 3-kinase (PI-3K) or agents that increase the biological activity or expression of a Krüppel-like factor such as KLF2 or a forkhead box factor such as FOXO1 or biologically active fragment or analog thereof. Agents so identified may be useful to treat a disease characterized, all or in part, or caused, all or in part, by an immune response. The disease characterized, all or in part, or caused, all or in part, by an immune response may be, for instance, excessive inflammation, an autoimmune disease such as, for instance, inflammatory bowel disease (IBD), multiple sclerosis (MS), lupus, or psoriasis, or graft-versus-host disease such as may occur after transplantation. As such, these methods are also methods of screening for therapeutic agents effective to inhibit or downregulate an immune response and to treat a disease characterized, all or in part, or caused, all or in part, by an immune response.

In an eighth aspect, the present invention provides methods to identify agents such as small molecules, proteins and antibodies, that may stimulate an immune response or that may increase or upregulate a T cell such as Th17+ or Th22+ cell activity or activation. The invention identifies a novel target that can be manipulated to regulate an immune response. Agents such as small molecules, proteins and antibodies that may stimulate an immune response or that may increase or upregulate a T cell such as Th17+ or Th22+ cell activity or activation may be identified by standard assay techniques known in the art as applied to identify those agents that increase the biological activity or expression of a phosphoinositide 3-kinase (PI-3K) or that decrease biological activity or expression of a Krüppel-like factor such as KLF2 or a forkhead box factor such as FOXO1 or a biologically active fragment or analog thereof. Agents so identified may be useful to treat a disease that may be successfully treated, all or in part, by stimulating an immune response. The disease that may be successfully treated, all or in part, by stimulating an immune response may be, for instance, a cancer, a neoplasm, a viral infection, a bacterial infection or a fungal infection. As such, these methods are also methods of screening for therapeutic agents effective to stimulate or upregulate an immune response and to treat a disease that may be successfully treated, all or in part, by stimulating an immune response.

In a ninth aspect, the present invention provides pharmaceutical compositions that may inhibit or downregulate an immune response, that may decrease or downregulate the biological activity of or expression of a phosphoinositide 3-kinase (PI-3K) or a phosphoinositide 3-kinase (PI-3K)/Akt pathway, or that may stimulate or increase the expression or biological activity of Krüppel-like factor such as KLF2 or a forkhead box factor such as FOXO1 or a biologically active fragment or analog thereof, and that may be effective to treat a disease characterized, all or in part, or caused, all or in part, by an immune response. The disease characterized, all or in part, or caused, all or in part, by an immune response may be, for instance, excessive inflammation, an autoimmune disease such as, for instance, inflammatory bowel disease (IBD), multiple sclerosis (MS), lupus, or psoriasis, or graft-versus-host disease such as may occur after transplantation. The pharmaceutical compositions contain one or more agents effective to decrease the biological activity or expression of a phosphoinositide 3-kinase (PI-3K) or to increase the biological activity or expression of a Krüppel-like factor such as KLF2 or a forkhead box factor such as FOXO1 or a biologically active fragment or analog thereof, along with a pharmaceutically acceptable carrier. In some instances, the pharmaceutical compositions may contain an agent that downregulates or inhibits expression of or biological activity of a phosphoinositide 3-kinase (PI-3K) or that upregulates or increases expression of or biological activity of a Krüppel-like factor such as KLF2 or a forkhead box factor such as FOXO1 or a biologically active fragment or analog thereof, such as, for instance, a small molecule, an antibody, a DNA or RNA, or a genetic construct, such as for instance might be administered by standard gene therapy techniques, along with a pharmaceutically acceptable carrier.

In an tenth aspect, the present invention provides pharmaceutical compositions that may stimulate or upregulate an immune response, that may increase or upregulate expression of or biological activity of a phosphoinositide 3-kinase (PI-3K) or that may decrease or downregulate expression of or biological activity of a Krüppel-like factor such as KLF2 or a forkhead box factor such as FOXO1 or a biologically active fragment or analog thereof, and that may be effective to treat a disease that may be successfully treated, all or in part, by stimulating an immune response, such as, for instance, a cancer, a neoplasm, a viral infection, a bacterial infection or a fungal infection. The pharmaceutical compositions contain one or more agents that function to increase or upregulate the expression or biological activity of a phosphoinositide 3-kinase (PI-3K) or one or more agents that function to decrease or downregulate the expression or biological activity of a Krüppel-like factor such as KLF2 or a forkhead box factor such as FOXO1 or a biologically active fragment or analog thereof. In some embodiments, the agent that functions to upregulate or increase the expression or biological activity of a phosphoinositide 3-kinase (PI-3K) or to downregulate or decrease expression of or biological activity of a Krüppel-like factor such as KLF2 or a forkhead box factor such as FOXO1 or a biologically active fragment or analog thereof, is a small molecule, an antibody or an interfering RNA or DNA molecule. The compositions may further contain a pharmaceutically effective carrier.

In a eleventh aspect the present invention features a vaccine effective to modulate an immune response that may contain a Krüppel-like factor such as KLF2 or a forkhead box factor such as FOXO1 or a biologically active fragment or analog thereof.

In a twelfth aspect, the present invention provides methods for treating a disease characterized, all or in part, or caused, all or in part, by an immune response. The disease characterized, all or in part, or caused, all or in part, by an immune response may be, for instance, excessive inflammation, an autoimmune disease such as, for instance, inflammatory bowel disease (IBD), multiple sclerosis (MS), lupus, or psoriasis, or graft-versus-host disease such as may occur after transplantation. The methods feature decreasing T cell activation or T cell biological activity by decreasing the biological activity or expression of a phosphoinositide 3-kinase (PI-3K) or a biologically active fragment or analog thereof, by inhibiting or decreasing activity of a phosphoinositide 3-kinase PI-3K/Akt biological pathway or by increasing the biological activity of or administering a transcription factor, such as, for instance, a Krüppel-like factor, for example KLF2, or a forkhead box factor, for example FOXO1, or a biologically active fragment or analog thereof. In some instances, the methods may be effected by administering an agent that inhibits expression of or biological activity of a phosphoinositide 3-kinase (PI-3K), or an agent that increases expression of or biological activity of a Krüppel-like factor such as KLF2 or a forkhead box factor such as FOXO1. In some embodiments, such agents are, for instance, a small molecule, an antibody, a DNA or RNA, or a genetic construct, such as might be administered by standard gene therapy techniques. In some instances, the methods are performed by administering a KLF2 or a FOXO1 or a biologically active fragment or analog thereof. In some instances, the T cells are helper T cells, such as, for instance, Th17+ or Th22+ cells. In some instances, the activation of T cells such as Th17+ or Th22+ cells or the T cell biological activity of such T cells may be decreased by about 5%, 10%, 20%, 30%, 40%, 50%, 60%, 75%, 80%, 90%, 95% or more, or the biological activity or expression of a phosphoinositide 3-kinase (PI-3K) or the activity of a phosphoinositide 3-kinase (PI-3K)/Akt biological pathway may be decreased by about 5%, 10%, 20%, 30%, 40%, 50%, 60%, 75%, 80%, 90%, 95% or more. In other instances, the biological activity of or amount of a transcription factor, such as, for instance, KLF2 or FOXO1 may be increased by about 5%, 10%, 20%, 30%, 40%, 50%, 60%, 75%, 80%, 90%, 95% or more.

In an thirteenth aspect, the present invention provides methods for treating a disease that may be successfully treated, all or in part, by stimulating an immune response, such as, for instance, a cancer, a neoplasm, a viral infection, a bacterial infection or a fungal infection. The methods feature increasing T cell activation or T cell biological activity by increasing the biological activity or expression of a phosphoinositide 3-kinase (PI-3K) or a biologically active fragment or analog thereof, by stimulating or increasing activity of a phosphoinositide 3-kinase (PI-3K)/Akt biological pathway or by inhibiting activity of an enzyme such as a transcription factor, for instance, a Krüppel-like factor such as KLF2 or a forkhead box factor such as FOXO1, or a biologically active fragment or analog thereof. In some instances, the methods may be effected by administering an agent that increases expression of or biological activity of a phosphoinositide 3-kinase (PI-3K). In other instances, the methods may be performed by administering an agent that decreases expression of or biological activity of a Krüppel-like factor such as KLF2 or a forkhead box factor such as FOXO1, or a biologically active fragment or analog thereof. The agent may be, for instance, a small molecule, an antibody, a DNA or RNA, or a genetic construct, such as might be administered by standard gene therapy techniques. In some instances, the methods are performed by administering an inhibitor such as an antibody to a KLF2 or a FOXO1 or a biologically active fragment or analog thereof. In some instances, the T cells are helper T cells, such as, for instance, Th17+ or Th22+ cells. In some instances, the activation of T cells such as T17+ or T22+ cells or the T cell biological activity may be increased by about 5%, 10%, 20%, 30%, 40%, 50%, 60%, 75%, 80%, 90%, 95% or more. Likewise, in some instances, the biological activity or expression of a phosphoinositide 3-kinase (PI-3K), the activity of a phosphoinositide 3-kinase (PI-3K)/Akt biological pathway may be increased by about 5%, 10%, 20%, 30%, 40%, 50%, 60%, 75%, 80%, 90%, 95% or more. Similarly, in other instances, biological activity or expression of a Krüppel-like factor such as KLF2 or a forkhead box factor such as FOXO1, or a biologically active fragment or analog thereof, may be decreased by about 5%, 10%, 20%, 30%, 40%, 50%, 60%, 75%, 80%, 90%, 95% or more.

Figures 1A, 1B:
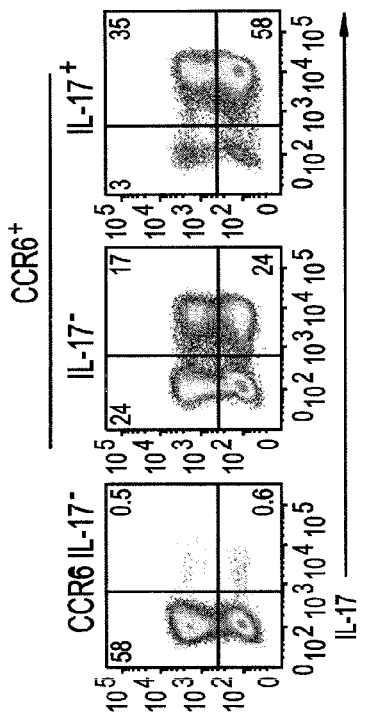
FIG. 1 shows that de novo expression of IL-17 in $CCR6^+$ $IL-17^-$ human memory T cells is induced by γc-cytokines. (a) Total $CD4^+$ $T_M$ cells ($CD45RO^+$ $CD25^-$) were stimulated for 18-24 hours with aCD3/aCD28 beads and then were FACS-sorted into $CCR6^-$ $IL17^-$, $CCR6^+$ $IL-17^-$, or $CCR6^+$ $IL-17^+$ populations by cytokine capture assay. (b) Cells sorted as in (a) following aCD3/aCD28 stimulation were analyzed by qPCR for expression of Il-17a and Rorc gene expression. (c) Live $CCR6^-IL-17^-$, $CCR6^+IL-17^-$, or $CCR6^+IL-17^+$ T cells were maintained in IL-2-containing medium for 6-7 days and were restimulated with PMA and ionomycin. Cytokine production was determined by intracellular staining (d) Cytokine gene expression was determined using quantitative nuclease protection assay (qNPA; see materials and methods) in CCR6$^-$IL17$^-$, CCR6$^+$IL-17$^-$, or CCR6$^+$IL-17$^+$ populations expanded for 7 days in IL-2-supplemented medium and restimulated with PMA and ionomycin. Cytokine mRNA expression was normalized to a housekeeper gene (Rpl19) and normalized values are presented as a fold-change on a scatter plot (where x axis=CCR6$^+$IL-17$^-$/CCR6$^-$IL-17$^-$, and y axis=CCR6$^+$IL-17$^+$/CCR6$^-$IL-17$^-$). Data from (a-d) is representative of three independent donors. (e) FACS sorted CCR6$^-$IL-17$^-$ cells (white bars), or CCR6$^+$IL-17$^-$ cells (black bars) sorted as in (a) were cultured in different cytokine conditions as indicated for 6 days. IL-17 expression was determined by FACS analysis following restimulation with PMA and ionomycin. Data are presented as the mean percentage of cells±SD from three different donors. (f) CCR6$^+$ IL-17$^-$ T$_M$ cells are specifically poised to express IL-17 in human rheumatoid arthritis patients. Total CD4$^+$ memory T cells isolated from the peripheral blood of rheumatoid arthritis patients were either stimulated directly ex vivo (day 0) with PMA and ionomycin, or were stimulated and FACS sorted as in (a) into CCR6$^-$IL-17$^-$ or CCR6$^+$IL-17$^-$ cells. These cells were cultured in IL-2-supplemented medium for 7 days prior to restimulation with PMA and Ionomycin (day 7). The frequencies of IL-17-producing cells were determined via intracellular staining and FACS analysis. Data shown are from 4 individual RA patients.

(c) CCR6⁻IL-17⁻, CCR6⁺IL-17⁻, or CCR6⁺IL-17⁺ T cells were maintained in IL-2-containing medium for 6-7 days and restimulated with PMA and ionomycin. Cytokine production was determined by intracellular staining (d) Schematic diagram depicting how FACS sorted aCD3/aCD28 activated CCR6⁺IL-17A⁺, or CCR6⁺IL-17A⁻ cells were labeled with CFSE or eFluor 670, respectively, plated in mixed cultures and stimulated with IL-2 to monitor proliferation. (e) Overlayed scatter plots showing dye dilution in CFSE-labeled (CCR6⁺IL-17⁺) or eFluor 670-labelled (CCR6⁺IL-17⁻) cells as analyzed on day 0 (directly post-labeling), day 2 and day 4 by FACS analysis. (f) Fold expansion was calculated by normalizing the MFI's at day 2 or 4 to day 0. (g) Co-cultures were stimulated with PMA and ionomycin on day 6. CCR6 IL-17⁺, or CCR6⁺IL-17⁻ cells were gated based on CFSE or eFluor 670 fluorescence and IL-17 expression was determined by intracellular staining Data shown are from one representative donor out of three donors.

FIG. 8 depicts that CCR6⁺ IL-17⁻ $T_M$ cells are specifically poised to express IL-17 in mice. (Left) Cells from the spleen and peripheral lymph nodes of wild-type C57B/6 mice were pooled and enriched for CD4⁺ T cells via magnetic cell separation on day 0. These cells were stimulated with aCD3/aCD28 for 18-24 hours and were FACS-sorted into CD4⁺ CD62L$^{lo}$CCR6⁻ IL-17⁻, CD4⁺CD62L$^{lo}$CCR6⁺IL-17⁻, or CD4⁺CD62L$^{lo}$CCR6⁺IL-17⁺ subsets following cytokine capture and staining (Right) Sorted cells were cultured for 7 days in the presence of IL-2 and then restimulated with PMA and ionomycin to determine production of IL-17 and IFNγ. Mouse data are representative of two independent experiments.

FIG. 9 demonstrates that PI-3K/Akt inhibitors repress IL-17 and IL-22 expression in TCR-activated CCR6⁺ human memory T cells cultured in IL-2. (a) Inhibition of Akt phosphorylation by inhibitors of PI-3K/Akt pathway in Jurkat cells. Jurkat T cells were untreated (red) or treated with different PI-3K signaling pathway inhibitors (blue), LY294002 and AKTi-1/2 at indicated concentration for 30 minutes. The cells were then stained intracellularly with either isotype control (Rabbit IgG-Alexa-488) (filled gray) or Phospho-Akt (Ser473) (pAkt)-Alexa 488. Data represents one staining from three independent experiments. (b) CCR6⁺/⁻ $T_M$ cells were cultured in the medium supplemented either with IL-4 (20 ng/ml) or IL-7 (20 ng/ml)+IL-23 (20 ng/ml) for 10 days. Frequency of IL-17⁺, IL-22⁺ and IFNγ⁺ cells were determined at day 0 (d0) or day 10 (d10) post culture in both CCR6⁺ and CCR6⁻ cells. Data represent the mean percentage of cells±SD from three different donors. (c) Resting CD4⁺ CD45RO⁺CD25⁻CCR6⁺ T cells were activated with aCD3/aCD28 beads for 2 weeks and treated with PI-3K/Akt inhibitors for an additional 2 days. Cells were then stimulated with PMA and ionomycin and subjected to intracellular staining and FACS analysis. Data are presented as mean frequency of cytokine producing cells±SD from three independent individuals. (d,e) PI-3K and Akt inhibitors inhibit IL-17, IL-22 and IL-4 induction from CCR6⁺ $T_M$ cells. Cells treated with inhibitors (μg/ml) as mentioned in (c) were further stimulated with PMA and ionomycin following intracellular cytokine staining and FACS analysis. Cytokine percentage of control was then calculated as before. Data are presented as the mean percentage of cells±SD from three different donors. (f) Rorc and Foxp3 are not affected by PI-3K/Akt inhibitors in CCR6⁺/⁻ cells. CCR6⁺/⁻ cells were cultured in IL-7 containing medium for 7 days followed by culturing in the absence or presence of PI-3K/Akt inhibitors, LY (LY294002) or AKT (AKTi-1/2), for an additional 2 days and mRNA was extracted to perform RT-qPCR. Fold change of transcripts normalized to cells without treatment is shown.

FIG. 10 shows additional cytokine profiles in γc-cytokine-cultured memory T cells. (a, b) IL-21 and IL-10 production from IL-7 cultured CCR6⁺/CCR6⁻ $T_M$ cells. Cells isolated and cultured in IL-7-containing medium, as described in materials and methods, were activated ex vivo (Day 0, or d0) or at Day 10 (d10) post culture in IL-7 medium with or without 2 days treatment with PI-3K/Akt inhibitors (5 μg/ml). The frequency of IL-21- and IL-10-producing cells from both CCR6⁺ and CCR6⁻ cells is shown as FACS plots (a) and analyzed in multiple donors (b). Data are presented as mean percent cytokine-producing cells±SD from different conditions compared to d10 IL7-cultured cells without inhibitors (filled/empty blue rectangle) from three different donors. (c) Cytokine gene expression quantified by qNPA in CCR6⁺ $T_M$ cells treated with LY294002 or AKTi-1/2 for 2 days relative to CCR6⁺ $T_M$ cells cultured in similar conditions without any PI-3K/Akt inhibitors. Solid orange ellipse denotes cytokines that are not affected by inhibitors of PI-3K (LY294002, 5 μg/ml, Y-axis) or Akt (AKTi-1/2, 5 μg/ml, X-axis) whereas dashed orange ellipse indicates cytokines that are downregulated compared to control treatment. Data are presented as mean mRNA fold change from three different donors. * $p<0.05$. NS: no significance.

FIG. 11 demonstrates validation of FOXO1 and KLF2 expression. (a) T cells transduced with EV-GFP or FOXO1-GFP were stained intracellularly with a specific, monoclonal, anti-FOXO1 antibody at day 4 post-transduction. (b) Klf2 transcripts expression in CCR6⁺ $T_M$ cells after treatment with PI-3 kinase inhibitors Inhibition of PI-3K/Akt signals upregulates Klf2 message expression. CCR6⁺ $T_M$ were activated by aCD3/aCD28 beads and expanded in IL-2 medium for 2 weeks. Cells were then treated with the PI-3K inhibitor, LY294002, or the AKT inhibitor, AKTi-1/2, at indicated concentrations for 2 days and total RNA from cell pellets was collected and subjected to RT-qPCR to detect Klf2 levels. Data shown are mean fold change of Klf2 mRNA±SD from one representative of three different donors. (c) Validation of KLF2 overexpression in Jurkat cells. Cell pellets collected from Jurkat cells transduced with a lentivirus encoding the Klf2 gene or a control were probed by western blot. (d) Validation of KLF2 knockdown. mRNA were collected from Jurkat cells transduced with shRNA against KLF2 and RT-qPCR was performed to quantify Klf2 mRNA. Data are presented as mean percentage of Klf2 transcripts±SD from three independent donors.

Figure 12:
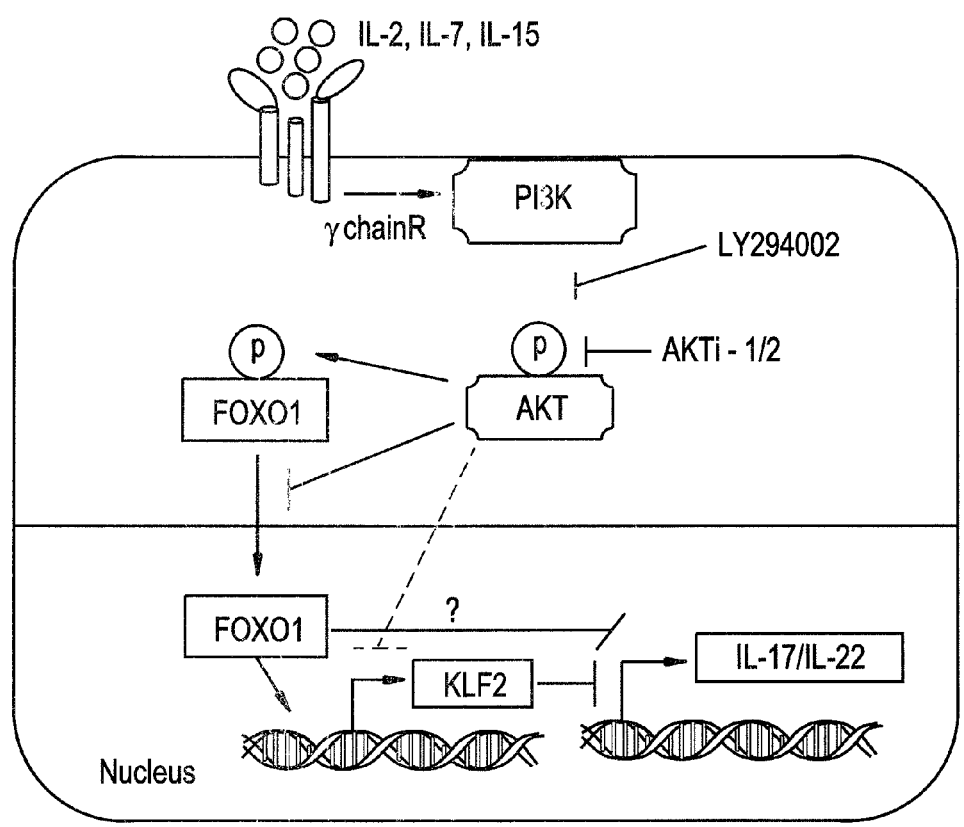

FIG. 12 demonstrates a model for potential mechanism for γc-cytokine-signals in regulating IL-17 and IL-22 production from CCR6⁺ memory T cells. γc-cytokines, such as IL-2, IL-7 and IL-15 signal through their receptors and activate PI-3K signaling pathway. Phosphorylation of Akt induced by PI-3K activation inactivates FOXO1 or other unidentified factors to maintain T cell homeostasis and survival by inducing different cytokines, for example IL-17 and IL-22. Once the γc-dependant PI-3K signaling pathway is either blocked by PI-3K and Akt specific inhibitors, or bypassed by overexpression of transcription factors, such as FOXO1 and KLF2, production of IL-17 and IL-22 is suppressed. The mechanism of this suppression could either be a direct transcriptional repression of Il-17 or Il-22 gene expression by KLF2 or FOXO1 or indirectly through the induction of KLF2 by FOXO1 and other yet-to-be-determined factors.

DETAILED DESCRIPTION OF THE INVENTION

Various terms are used in the specification, which are defined as follows:

As used herein a "small organic molecule" or "small molecule" is an organic compound (or organic compound complexed with an inorganic compound (e.g., metal)) that has a molecular weight of less than 3 kilodaltons, and preferably less than 1.5 kilodaltons. An "agent" of the present invention is preferably a small organic molecule.

The phrase "pharmaceutically acceptable" refers to molecular entities and compositions that are physiologically tolerable and do not typically produce an allergic or similar untoward reaction, such as gastric upset, dizziness and the like, when administered to a human. Preferably, as used herein, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant, excipient, or vehicle with which the compound is administered. Such pharmaceutical carriers can be sterile liquids, such as water and oils, including those of petroleum, animal, vegetable or synthetic origin, such as peanut oil, soybean oil, mineral oil, sesame oil and the like. Water or aqueous solution saline solutions and aqueous dextrose and glycerol solutions are preferably employed as carriers, particularly for injectable solutions. Suitable pharmaceutical carriers are described in "Remington's Pharmaceutical Sciences" by E. W. Martin.

The phrase "therapeutically effective amount" is used herein to mean an amount sufficient to reduce by at least about 15 percent, preferably by at least 50 percent, more preferably by at least 90 percent, and most preferably prevent, a clinically significant deficit in the activity, function and response of the host. Alternatively, a therapeutically effective amount is sufficient to cause an improvement in a clinically significant condition in the host.

In a specific embodiment, the term "about" means within 20%, preferably within 10%, and more preferably within 5%.

In accordance with the present invention there may be employed conventional molecular biology, microbiology, and recombinant DNA techniques within the skill of those in the art. Such techniques are explained fully in the literature. See, e.g., Sambrook, Fritsch & Maniatis, Molecular Cloning: A Laboratory Manual, Second Edition (1989) Cold Spring Harbor Laboratory Press, Cold Spring Harbor, N.Y. (herein "Sambrook et al., 1989"); DNA Cloning: A Practical Approach, Volumes I and II (D. N. Glover ed. 1985); Oligonucleotide Synthesis (M. J. Gait ed. 1984); Nucleic Acid Hybridization (B. D. Hames & S. J. Higgins eds. (1985)); Transcription And Translation (B. D. Hames & S. J. Higgins, eds. (1984)); Animal Cell Culture (R. I. Freshney, ed. (1986)); Immobilized Cells And Enzymes (IRL Press, (1986)); B. Perbal, A Practical Guide To Molecular Cloning (1984); F. M. Ausubel et al. (eds.), Current Protocols in Molecular Biology, John Wiley & Sons, Inc. (1994).

The term "disease characterized, all or in part, or caused, all or in part, by an immune response" includes, for example, the following diseases: all autoimmune diseases (e.g. Rheumatoid arthritis, Psoriasis, Multiple sclerosis, ulcerative colitis, Crohn's disease, type I juvenile diabetes, SLE), allergic diseases (e.g. asthma, atopic dermatitis, allergic rhinitis, food allergies), transplantation rejection and graft-versus-host-disease after solid organ or bone marrow transplantation respectively, various cancers where TGFβ signaling is involved in promoting tumors such as breast and lung cancer, chronic diseases that are caused or promoted by inflammation (e.g. atherosclerosis, congestive heart failure, type II diabetes, chronic obstructive pulmonary disease (COPD), Alzheimer's disease, fibrosis, stroke, pancreatitis), and during chronic infections that cause excessive immune activation such as HIV infection, severe forms of influenza, tuberculosis, shingles, CMV infections, bacterial infections that can cause septic shock.

The singular forms "a", "an", and "the" include plural references unless the context clearly dictates otherwise. Thus for example, reference to "the method" includes one or more methods, and/or steps of the type described herein and/or which will become apparent to those persons skilled in the art upon reading this disclosure.

The term "administering" as used herein in usually intended to mean providing a therapeutically effective amount.

The term "activating" or "activation" when used to describe or in reference to T cells generally refers to the change in morphology and behavior of a mature or immature T cell resulting from exposure to a mitogen, cytokine, chemokine, cellular ligand, or an antigen for which it is specific. The terms generally refer to an increased activity or increased ability to perform intended function. Such "activation" may be evidenced, for example, by increased cytokine expression, e.g. IL17 or IL22 expression. Such increased expression may be 5%, 10%, 25%, 50%, or 2×, 3×, 4×, or more normal cytokine expression as observed when the T cells are in a relatively non-activated state or less activated state.

The term "differentiation" when used to describe or in reference to T cells generally refers to the process in which a precursor cell type acquires characteristics of a more mature T-cell, for example the expression of a T cell receptor complex or expression of particular cytokines such as, for example, interleukins like IL17 or IL22.

The term "proliferation" when used to describe or in reference to T cells generally refers to the expansion of a T cell population by cell division. Proliferation generally follows T cell activation.

The term "complementary" refers to two DNA strands that exhibit substantial normal base pairing characteristics. Complementary DNA may, however, contain one or more mismatches.

The term "hybridization" refers to the hydrogen bonding that occurs between two complementary DNA strands.

"Nucleic acid" or a "nucleic acid molecule" as used herein refers to any DNA or RNA molecule, either single or double stranded and, if single stranded, the molecule of its complementary sequence in either linear or circular form. In discussing nucleic acid molecules, a sequence or structure of a particular nucleic acid molecule may be described herein according to the normal convention of providing the sequence in the 5' to 3' direction. With reference to nucleic acids of the invention, the term "isolated nucleic acid" is sometimes used. This term, when applied to DNA, refers to a DNA molecule that is separated from sequences with which it is immediately contiguous in the naturally occurring genome of the organism in which it originated. For example, an "isolated nucleic acid" may comprise a DNA molecule inserted into a vector, such as a plasmid or virus vector, or integrated into the genomic DNA of a prokaryotic or eukaryotic cell or host organism.

When applied to RNA, the term "isolated nucleic acid" refers primarily to an RNA molecule encoded by an isolated DNA molecule as defined above. Alternatively, the term may refer to an RNA molecule that has been sufficiently separated from other nucleic acids with which it is generally associated in its natural state (i.e., in cells or tissues). An isolated nucleic acid (either DNA or RNA) may further represent a molecule produced directly by biological or synthetic means and separated from other components present during its production.

The term "functional" as used herein implies that the nucleic or amino acid sequence is functional for the recited assay or purpose.

The phrase "consisting essentially of" when referring to a particular nucleotide or amino acid means a sequence having the properties of a given SEQ ID No:. For example, when used in reference to an amino acid sequence, the phrase includes the sequence per se and molecular modifications that would not affect the basic and novel characteristics of the sequence.

A "replicon" is any genetic element, for example, a plasmid, cosmid, bacmid, phage or virus, that is capable of replication largely under its own control. A replicon may be either RNA or DNA and may be single or double stranded.

A "vector" is a replicon, such as a plasmid, cosmid, bacmid, phage or virus, to which another genetic sequence or element (either DNA or RNA) may be attached so as to bring about the replication of the attached sequence or element.

An "expression vector" or "expression operon" refers to a nucleic acid segment that may possess transcriptional and translational control sequences, such as promoters, enhancers, translational start signals (e.g., ATG or AUG codons), polyadenylation signals, terminators, and the like, and which facilitate the expression of a polypeptide coding sequence in a host cell or organism.

As used herein, the term "operably linked" refers to a regulatory sequence capable of mediating the expression of a coding sequence and which is placed in a DNA molecule (e.g., an expression vector) in an appropriate position relative to the coding sequence so as to effect expression of the coding sequence. This same definition is sometimes applied to the arrangement of coding sequences and transcription control elements (e.g. promoters, enhancers, and termination elements) in an expression vector. This definition is also sometimes applied to the arrangement of nucleic acid sequences of a first and a second nucleic acid molecule wherein a hybrid nucleic acid molecule is generated.

The term "oligonucleotide," as used herein refers to primers and probes of the present invention, and is defined as a nucleic acid molecule comprised of two or more ribo- or deoxyribonucleotides, preferably more than three. The exact size of the oligonucleotide will depend on various factors and on the particular application and use of the oligonucleotide.

The term "probe" as used herein refers to an oligonucleotide, polynucleotide or nucleic acid, either RNA or DNA, whether occurring naturally as in a purified restriction enzyme digest or produced synthetically, which is capable of annealing with or specifically hybridizing to a nucleic acid with sequences complementary to the probe. A probe may be either single-stranded or double-stranded. The exact length of the probe will depend upon many factors, including temperature, source of probe and use of the method. For example, for diagnostic applications, depending on the complexity of the target sequence, the oligonucleotide probe typically contains 15-25 or more nucleotides, although it may contain fewer nucleotides. The probes herein are selected to be "substantially" complementary to different strands of a particular target nucleic acid sequence. This means that the probes must be sufficiently complementary so as to be able to "specifically hybridize" or anneal with their respective target strands under a set of pre-determined conditions. Therefore, the probe sequence need not reflect the exact complementary sequence of the target. For example, a non-complementary nucleotide fragment may be attached to the 5' or 3' end of the probe, with the remainder of the probe sequence being complementary to the target strand. Alternatively, non-complementary bases or longer sequences can be interspersed into the probe, provided that the probe sequence has sufficient complementarity with the sequence of the target nucleic acid to anneal therewith specifically.

The term "specifically hybridize" refers to the association between two single-stranded nucleic acid molecules of sufficiently complementary sequence to permit such hybridization under pre-determined conditions generally used in the art (sometimes termed "substantially complementary"). In particular, the term refers to hybridization of an oligonucleotide with a substantially complementary sequence contained within a single-stranded DNA or RNA molecule of the invention, to the substantial exclusion of hybridization of the oligonucleotide with single-stranded nucleic acids of non-complementary sequence.

The term "primer" as used herein refers to an oligonucleotide, either RNA or DNA, either single-stranded or double-stranded, either derived from a biological system, generated by restriction enzyme digestion, or produced synthetically which, when placed in the proper environment, is able to functionally act as an initiator of template-dependent nucleic acid synthesis. When presented with an appropriate nucleic acid template, suitable nucleoside triphosphate precursors of nucleic acids, a polymerase enzyme, suitable cofactors and conditions such as a suitable temperature and pH, the primer may be extended at its 3' terminus by the addition of nucleotides by the action of a polymerase or similar activity to yield a primer extension product. The primer may vary in length depending on the particular conditions and requirement of the application. For example, in diagnostic applications, the oligonucleotide primer is typically 15-25 or more nucleotides in length. The primer must be of sufficient complementarity to the desired template to prime the synthesis of the desired extension product, that is, to be able anneal with the desired template strand in a manner sufficient to provide the 3' hydroxyl moiety of the primer in appropriate juxtaposition for use in the initiation of synthesis by a polymerase or similar enzyme. It is not required that the primer sequence represent an exact complement of the desired template. For example, a non-complementary nucleotide sequence may be attached to the 5' end of an otherwise complementary primer. Alternatively, non-complementary bases may be interspersed within the oligonucleotide primer sequence, provided that the primer sequence has sufficient complementarity with the sequence of the desired template strand to functionally provide a template-primer complex for the synthesis of the extension product.

Primers may be labeled fluorescently with 6-carboxyfluorescein (6-FAM). Alternatively primers may be labeled with 4,7,2',7'-Tetrachloro-6-carboxyfluorescein (TET). Other alternative DNA labeling methods are known in the art and are contemplated to be within the scope of the invention.

The term "isolated protein" or "isolated and purified protein" is sometimes used herein. This term refers primarily to a protein produced by expression of an isolated nucleic acid molecule of the invention. Alternatively, this term may refer to a protein that has been sufficiently separated from other proteins with which it would naturally be associated, so as to exist in "substantially pure" form. "Isolated" is not meant to exclude artificial or synthetic mixtures with other compounds or materials, or the presence of impurities that do not interfere with the fundamental activity, and that may be present, for example, due to incomplete purification, addition of stabilizers, or compounding into, for example, immunogenic preparations or pharmaceutically acceptable preparations.

The term "substantially pure" refers to a preparation comprising at least 50-60% by weight of a given material (e.g., nucleic acid, oligonucleotide, protein, etc.). More particularly, the preparation comprises at least 75% by weight, and most particularly 90-95% by weight of the given compound. Purity is measured by methods appropriate for the given compound (e.g. chromatographic methods, agarose or polyacrylamide gel electrophoresis, HPLC analysis, and the like). "Mature protein" or "mature polypeptide" shall mean a polypeptide possessing the sequence of the polypeptide after any processing events that normally occur to the polypeptide during the course of its genesis, such as proteolytic processing from a polypeptide precursor. In designating the sequence or boundaries of a mature protein, the first amino acid of the mature protein sequence is designated as amino acid residue 1.

The term "tag", "tag sequence" or "protein tag" refers to a chemical moiety, either a nucleotide, oligonucleotide, polynucleotide or an amino acid, peptide or protein or other chemical, that when added to another sequence, provides additional utility or confers useful properties to the sequence, particularly with regard to methods relating to the detection or isolation of the sequence. Thus, for example, a homopolymer nucleic acid sequence or a nucleic acid sequence complementary to a capture oligonucleotide may be added to a primer or probe sequence to facilitate the subsequent isolation of an extension product or hybridized product. In the case of protein tags, histidine residues (e.g., 4 to 8 consecutive histidine residues) may be added to either the amino- or carboxy-terminus of a protein to facilitate protein isolation by chelating metal chromatography. Alternatively, amino acid sequences, peptides, proteins or fusion partners representing epitopes or binding determinants reactive with specific antibody molecules or other molecules (e.g., flag epitope, c-myc epitope, transmembrane epitope of the influenza A virus hemaglutinin protein, protein A, cellulose binding domain, calmodulin binding protein, maltose binding protein, chitin binding domain, glutathione S-transferase, and the like) may be added to proteins to facilitate protein isolation by procedures such as affinity or immunoaffinity chromatography. Chemical tag moieties include such molecules as biotin, which may be added to either nucleic acids or proteins and facilitates isolation or detection by interaction with avidin reagents, and the like. Numerous other tag moieties are known to, and can be envisioned by, the trained artisan, and are contemplated to be within the scope of this definition.

The terms "transform", "transfect", "transduce", shall refer to any method or means by which a nucleic acid is introduced into a cell or host organism and may be used interchangeably to convey the same meaning Such methods include, but are not limited to, viral transduction, transfection, electroporation, microinjection, PEG-fusion and the like.

The introduced nucleic acid may or may not be integrated (covalently linked) into nucleic acid of the recipient cell or organism. In bacterial, yeast, plant and mammalian cells, for example, the introduced nucleic acid may be maintained as an episomal element or independent replicon such as a plasmid. Alternatively, the introduced nucleic acid may become integrated into the nucleic acid of the recipient cell or organism and be stably maintained in that cell or organism and further passed on or inherited to progeny cells or organisms of the recipient cell or organism. In other applications, the introduced nucleic acid may exist in the recipient cell or host organism only transiently.

A "clone" or "clonal cell population" is a population of cells derived from a single cell or common ancestor by mitosis.

A "cell line" is a clone of a primary cell or cell population that is capable of stable growth in vitro for many generations.

An "immune response" signifies any reaction produced by an antigen, such as a protein antigen, in a host having a functioning immune system. Immune responses may be either humoral, involving production of immunoglobulins or antibodies, or cellular, involving various types of B and T lymphocytes, dendritic cells, macrophages, antigen presenting cells and the like, or both. Immune responses may also involve the production or elaboration of various effector molecules such as cytokines, lymphokines and the like. Immune responses may be measured both in in vitro and in various cellular or animal systems.

An "antibody" or "antibody molecule" is any immunoglobulin, including antibodies and fragments thereof, that binds to a specific antigen. The term includes polyclonal, monoclonal, chimeric, and bispecific antibodies. As used herein, antibody or antibody molecule contemplates both an intact immunoglobulin molecule and an immunologically active portion of an immunoglobulin molecule such as those portions known in the art as Fab, Fab', F(ab')2 and F(v).

The term "about" as used herein refers to a variation in a stated value or indicated amount of up to 20%, 15%, 10%, 9%, 8%, 7%, 6%, 5%, 4%, 3%, 2%, 1%, 0.75%, 0.5%, 0.25% or 0.1%, wherein the variation can be either an increase or a decrease in the stated value or indicated amount. Use of the term may, therefore, be used to establish a range of values or amounts.

As used herein, the term "serum-free culture medium" is defined as serum-free cell culture medium that has a defined chemical composition and supports proliferation of human lymphocytes. A list of serum-free culture medium useful in the present invention would include, without limitation, LONZA XVIVO-5, XVIVO-10, XVIVO-20, Sigma StemLine I, StemLine II, Yssel's media and AimV media.

Exemplary serum-free medium is described in the Example section presented herein. An exemplary serum-free medium is serum-free XVIVO-20 (Lonza), which may optionally be supplemented with penicillin-streptomycin.

MEM and RPMI are protein-free basal media that do not contain growth factors required for lymphocytes. A skilled practitioner would appreciate that a protein-free basal media can, however, be converted to serum-free media capable of supporting lymphocyte proliferation following addition of required growth factors. Such serum-free media contain specific and defined growth factors (e.g., insulin) that are required for lymphocyte proliferation.

In Vitro Methods

As described herein, the present invention is directed to a method for promoting differentiation, activation and proliferation of human T helper lymphocytes such as those that express IL17 or IL22 (Th-IL17+ or Th-IL22+ cells) in vitro. As also described herein, the invention is directed to a method for generating a population of human T helper lymphocytes such as those that express IL17 or IL22 (Th-IL17+ or Th-IL22+ cells) in vitro. The in vitro methods of the invention are based on the novel and surprising discoveries that promote human IL17 or IL22 (Th-IL17+ or Th-IL22+ cells) cell differentiation, activation and proliferation, which also provides a method for generating in vitro a population of human T cells such as IL17 or IL22 (Th-IL17+ or Th-IL22+ cells) cells. The method calls for incubation of T cells such as CD45RO+ or CCR6+ T memory cells in a serum-free media supplemented with one or more of IL-2, IL-7 or IL-15. Conditions wherein T cells are incubated in serum-free media may also be referred to herein as human T cell or Th-IL17+ or Th-IL22+ cell promoting conditions. A negative control for human Th-IL 17+ or Th-IL22+ cell promoting conditions is a matched serum-free media without cytokine supplementation. An exemplary negative control for human Th-IL17+ or Th-IL22+ cell promoting conditions is a matched serum-free media alone. It is to be understood that supplementation with standard media additives for prevention of bacterial or fungal infection (such as, e.g., penicillin-streptomycin) is not precluded from the method of the present invention. Indeed, in a particular embodiment of the present invention, the media with or without serum may include any one of the following cytokine supplementation IL-2, IL-15 or IL-7, in addition to antibiotics.

In vitro differentiation and activation of human T cells such as Th-IL17+ or Th-IL22+ cells may be evaluated or measured by detecting an increase in the expression of a human Th-IL17+ cell marker, such as IL17, IL17F, IL23R, or RORC, or Th-22 marker IL22 in a population of T cells incubated in accordance with the present method. Each of these cellular molecules (IL17, IL17F, IL23R, RORC or IL22) serves as a positive marker indicative of human Th-IL17+ or Th-22 cell differentiation and activation. Indeed, expression of IL17, IL17F, IL23R, RORC or IL22 may be induced by 5- to about 100-fold in cells incubated in human Th-IL17+ or Th-IL22+ cell promoting conditions relative to those treated under negative control conditions. Accordingly, a change in the expression of at least one of these markers reflects a differential in human Th-IL 17+ or Th-IL22+ cell differentiation and activation. A change in expression of any of these markers may be determined using a variety of experimental protocols, including, but not limited to, real-time PCR using appropriate primers. Experimental protocols that can be used to determine expression of such markers and relative expression levels are described in detail herein and are understood in the art.

Agents

As used herein, an "agent", "candidate compound", or "test compound" may be used to refer to, for example, nucleic acids (e.g., DNA and RNA), carbohydrates, lipids, proteins, peptides, peptidomimetics, small molecules and other drugs. More particularly an agent may refer to azole-containing compounds, cholesterol derivative compounds, retinoid derivative compounds, short hairpin RNA (shRNA), small interfering RNA (siRNA), neutralizing and/or blocking antibodies, tryptophan derivative compounds, Vitamin D derivatives, or molecules known to inhibit fever, inflammation, or regulatory T (Treg) cell differentiation and activation.

A short hairpin RNA (shRNA) is a sequence of RNA that makes a tight hairpin turn that can be used to silence gene expression via RNA interference. shRNA is generally expressed using a vector introduced into cells, wherein the vector utilizes the U6 promoter to ensure that the shRNA is always expressed. This vector is usually passed on to daughter cells, allowing the gene silencing to be inherited. The shRNA hairpin structure is cleaved by the cellular machinery into siRNA, which is then bound to the RNA-induced silencing complex (RISC). This complex binds to and cleaves mRNAs that match the siRNA to which it is bound.

Small interfering RNA (siRNA), sometimes known as short interfering RNA or silencing RNA, are a class of 20-25 nucleotide-long double-stranded RNA molecules that play a variety of roles in biology. Most notably, siRNA is involved in the RNA interference (RNAi) pathway whereby the siRNA interferes with the expression of a specific gene.

As described herein, an agent identified using the method of the present invention that is a "modulator of human Th-IL17+ or Th-IL22+ cell differentiation and activation" is defined as an agent that is capable of modulating (e.g., increasing or decreasing) in vitro the level of Th-IL-17 or Th-22 specific genes in memory T cells upon their activation. Such an agent may be identified by its ability to effect a change in the expression of a human T cell such as a human Th-IL17+ or Th-IL22+ cell marker, such as IL17, IL17F, IL23R, RORC or IL22, in a population of CD4+T cells incubated in human Th-IL17+ or Th-IL22+ cell promoting conditions. As described herein, each of these cellular molecules (IL17, IL17F, IL23R, RORC or IL22) serves as a positive marker indicative of human Th-IL17+ or Th-IL22+ cell differentiation and activation. Expression of IL17, IL17F, IL23R, RORC or IL22 can be induced by 5- to 100-fold in T cells treated to promote Th-IL17+ or Th-IL22+ cell differentiation and activation relative to those treated under negative control conditions in accordance with the method of the present invention. In contrast, memory T cells that are CCR6 negative do not induce IL17, IL17F, IL23R, RORC or IL22 under same culture conditions, demonstrating specificity of the culture conditions to modulate proteins associated with CCR6+ memory cells for Th-IL17+ or Th-IL22+ cells. Accordingly, a change in the expression of at least one of these markers (positive or negative) responsive to the presence of an agent reflects a differential in human Th-IL 17+ or Th-IL22+ cell differentiation and activation. More particularly, a change in the expression of at least one of these markers reflects a differential in human Th-IL17+ or Th-IL22+ cell differentiation and activation in a population of cells incubated in human Th-IL17+ or Th-IL22+ cell promoting conditions, wherein the change is dependent on incubation in the presence of a particular agent. As detailed below, experimental protocols of utility in determining expression of such markers and relative expression levels are described in detail herein and are understood in the art. Such experimental protocols, include, but are not limited to, real-time PCR using appropriate primers.

In accordance with the present invention, the method described herein may be used to achieve an increase in the number of human Th-IL17+ or Th-IL22+ cells in a cell population incubated in human Th-IL17+ or Th-IL22+ cell promoting conditions, as described herein. An increase in the number of human Th-IL17+ or Th-IL22+ cells in such a cell population may be expressed as the percent (%) of human Th-IL17+ or Th-IL22+ cells present in such a cell population relative to the total number of cells. In accordance with the present invention, the method described herein may achieve 1% to 15% human Th-IL17+ or Th-IL22+ cells in a cell population. It will be appreciated, however, that the present method may be used to achieve a higher relative percent human Th-IL17+ or Th-IL22+ cells in a cell population. Accordingly, the present invention is not in any way limited to achieving 1% to 15% human Th-IL17+ or Th-IL22+ cells in a treated cell population.

In light of the above, it will be appreciated that an agent identified using the method of the present invention that is a "modulator of human Th-IL17+ or Th-IL22+ cell function upon activation" may be identified by its ability to effect a change in the percent of human Th17+ or Th-IL22+ cells in a population of T cells incubated in human Th-IL17+ or Th-IL22+ cell promoting conditions. As taught herein, a change in the percent of human Th17+ or Th-IL22+ cells in a population of T cells incubated in the presence of an agent is determined relative to the percent of human Th-IL17+ or Th-IL22+ cells in a population of CD4+T cells incubated in the absence of the agent or in the presence of a control agent (negative control condition).

The term "control substance", "control agent", or "control compound" as used herein refers a molecule that is inert or has no activity relating to an ability to modulate a biological activity. With respect to the present invention, such control substances are inert with respect to an ability to modulate human Th-IL17+ or Th-IL22+ cell differentiation and activation in vitro. Exemplary controls include, but are not limited to, solutions comprising physiological salt concentrations.

In accordance with the present invention, incubation in the presence of an agent that results in a decrease in expression of a human Th-IL17+ cell marker, such as IL17, IL17F, IL23R, RORC or IL22, indicates that the agent is an inhibitor of human Th-IL17+ or Th-IL22+ cell differentiation and activation in vitro. An agent that results in a decrease in expression of a human Th-IL17+ or Th-IL22+ cell marker, such as IL17, IL17F, IL23R, RORC or IL22, is referred to herein as an inhibitor of human Th-IL17+ or Th-IL22+ cell function upon activation. An inhibitor of human Th-IL17+ or Th-IL22+ cell function is an agent that effects at least a 2-fold decrease in the expression of a human Th-IL17+ or Th-IL22+ cell marker, such as IL17, IL17F, IL23R, RORC or IL22. More particularly, an inhibitor of human Th-IL17+ or Th-IL22+ cell function upon activation is an agent that effects at least a 3-fold decrease in the expression of a human Th-IL17+ or Th-IL22+ cell marker, such as IL17, IL17F, IL23R, RORC or IL22. The above fold decreases may be determined relative to human Th-IL17+ or Th-IL22+ cell marker expression levels induced by incubation in human Th-IL17+ or Th-IL22+ cell promoting conditions in the absence of the agent.

In accordance with the present invention, incubation in the presence of an agent that results in an increase in expression of a human Th-IL17+ or Th-IL22+ cell marker, such as IL17, IL17F, IL23R, RORC or IL22, indicates that the agent is a promoter of human Th-IL17+ or Th-IL22+ cell function upon activation in vitro. An agent that results in an increase in expression of a human Th-IL17+ or Th-IL22+ cell marker, such as IL17, IL17F, IL23R, RORC or IL22, is referred to herein as a promoter of human Th-IL17+ or Th-IL22+ cell differentiation and activation. A promoter of human Th-IL17+ cell differentiation and activation may be an agent that effects at least a 2-fold increase in the expression of a human Th-IL 17+ or Th-IL22+ cell marker, such as IL17, IL17F, IL23R, RORC or IL22. More particularly, a promoter of human Th-IL17+ or Th-IL22+ cell differentiation and activation may be an agent that effects at least a 3-fold increase in the expression of a human Th-IL17+ cell marker, such as IL17, IL17F, IL23R, RORC or IL22. The above fold increases may be determined relative to human Th-IL17+ or Th-IL22+ cell marker expression levels induced by incubation in human Th-IL17+ cell promoting conditions in the absence of the agent.

Also in accordance with the present invention, incubation in the presence of an agent with CCR6 negative memory T cells does not result in a expression of IL17, IL17F, IL23R, RORC or IL22 indicates that the agent is a promoter or inducer of human Th-IL17+ or Th-IL22+ cell function and activation in vitro. Furthermore, in the presence of an agent expression of other cytokines such as IFNg, IL-2 or TNF are not affected in either CCR6+ or CCR6– memory T cells.

Also in accordance with the present invention, incubation in the presence of an agent that results in a decrease in expression of either of IL17, IL17F, or IL22 indicates that the agent is an inhibitor of human Th-IL17+ or Th-IL22+ cell differentiation and activation in vitro. An agent that results in a decrease in expression of either of IL 17, IL17F, or IL22, therefore, referred to herein as an inhibitor of human Th-IL17+ or Th-IL22+ cell differentiation and activation. An inhibitor of human Th-IL 17+ cell differentiation and activation is an agent that effects at least a 2-fold decrease in expression of IL17, IL17F, or IL22. More particularly, an inhibitor of human Th-IL17+ or Th-IL22+ cell differentiation and activation is an agent that effects at least a 3-fold decrease in expression of IL17, IL17F, or IL22. The above fold decreases are determined relative to IL17, IL17F, or IL22 expression levels observed under matched control conditions, but in the absence of the agent.

In accordance with the present invention, incubation in the presence of an agent that results in a decrease in the percent of human Th-IL17+ or Th-IL22+ cells generated indicates that the agent inhibits human Th-IL17+ or Th-IL22+ cell differentiation and activation in vitro. Such an agent is referred to herein as an inhibitor of secretion of proteins specific from human Th-IL17+ or Th-IL22+ upon their activation. An inhibitor of human Th-IL17+ or Th-IL22+ cell function is an agent that effects at least a 2-fold decrease in the percent of human Th17+ or Th-IL22+ cells generated. More particularly, an inhibitor of human Th-IL17+ or Th-IL22+ cell function is an agent that effects at least a 3-fold decrease in the percent of human Th17+ or Th-IL22+ cells that produce IL-17, IL-17F or IL-22. The above fold decreases may be determined relative to the percent of human Th17+ or Th-IL22+ cells generated by incubation in human Th-IL17+ or Th-IL22+ cell promoting conditions in the absence of the agent.

In accordance with the present invention, incubation in the presence of an agent that results in an increase in the percent of human Th-IL17+ or Th-IL22+ cells producing IL-17, IL-F or IL-22 indicates that the agent promotes human Th-IL17+ or Th-IL22+ cell function upon activation in vitro. Such an agent is referred to herein as a promoter/inducer of human Th-IL17+ or Th-IL22+ cell function. A promoter or inducer of human Th-IL17+ or Th-IL22+ cell differentiation and activation is an agent that effects at least a 2-fold increase in the percent of human Th17+ or Th-IL22+ cells producing IL-17, IL-F or IL-22. More particularly, a promoter/inducer of human Th-IL17+ or Th-IL22+ cell function is an agent that effects at least a 3-fold increase in the percent of human Th17+ or Th-IL22+ cells producing IL-17, IL-F or IL-22. The above fold increases may be determined relative to the percent of human Th17+ or Th-IL22+ cells producing IL-17, IL-F or IL-22 by incubation in human Th-IL17+ or Th-IL22+ cell promoting conditions in the absence of the agent.

It is to be understood that agents capable of modulating human Th-IL17+ or Th-IL22+ cell function, as determined using the in vitro method described herein, are likely to exhibit similar modulatory capacity in applications in vivo.

Modulatory agents identified using the screening methods of the present invention and compositions thereof can thus be administered for therapeutic treatments. In therapeutic applications, modulatory agents that inhibit Th-IL17+ or Th-IL22+ T cell function (i.e., inhibitors of Th-IL17+ or Th-IL22+ T cell differentiation and activation) and compositions thereof are administered to a patient suffering from an inflammatory or autoimmune disorder in an amount sufficient to at least partially arrest a symptom or symptoms of the disease and its complications. An amount adequate to accomplish this is defined as a "therapeutically effective amount or dose." Amounts effective for this use will depend on the severity of the disease and the weight and general state of the patient.

Examples of inflammatory or autoimmune disorders that may be treated using inhibitors of Th-IL17+ T cell differentiation and activation include, without limitation, multiple sclerosis, rheumatoid arthritis, Crohn's disease, and ulcerative colitis.

Methods for Determining Expression Levels of Human Th-IL17+ or Th-IL22+ Cell Markers Based on the guidance presented herein and knowledge in the relevant scientific fields, the expression level of a cellular marker of human Th-IL17+ or Th-IL22+ cells can be determined using a variety of techniques. Exemplary markers of human Th-IL17+ or Th-IL22+ cell differentiation and activation include, but are not limited to, IL17, IL17F, IL23R, RORC and IL26. Expression of FOXP3, on the other hand, is negatively correlated with human Th-IL17+ or Th-IL22+ cell differentiation and activation. FOXP3 is, therefore, a negative marker of human Th-IL 17+ or Th-IL22+ cell differentiation and activation. Expression levels of such markers (either a positive or a negative marker) may be assessed with respect to expressed nucleic acid corresponding to a cell marker (e.g., mRNA, total RNA) or with respect to polypeptides encoded by same. A variety of standard protocols may be used to determine, for example, RNA level, including, but not limited to: polymerase chain amplification and detection of amplified products therefrom, ribonuclease protection (RNase protection) assay, and Northern blot analysis or the protein levels by immunohistochemistry, western blot, ELISA or FACS analysis. The principles and general procedures of each of these methods are described in, for example, Dvorak et al. (Biomed Papers 147:131, 2003), which is incorporated herein in its entirety. The principles and general procedures of each of these methods are, moreover, known in the art. In a particular embodiment of the invention, real-time PCR is used to detect gene expression of human Th-IL17+ cell markers.

Real-Time PCR

As taught herein, detection of IL-17, IL17F, IL23R, RORC or IL22 gene expression may be used as a means to assess human Th-IL17+ or Th-IL22+ function and activation. Detection of these markers of human Th-IL17+ or Th-IL22+ function upon activation, therefore, provides positive indicators or readouts for the present method for promoting induction of effector functions and molecules expressed in Th-IL17+ or Th-IL22+ cells. The induction of these genes in Th17 or Th22 promoting conditions is at least 3-fold, and can achieve about 100-fold relative to the levels of these genes in non-promoting conditions. Particulars relating to real-time PCR analysis are presented in the Examples, as are primers for amplification of the above-indicated Th-IL17 or Th-IL22+ markers.

In CCR6− cells that are non-Th17 or non-Th22. there are no detectable Th-IL17 or Th-IL22 marker genes at the level of RNA or protein. The absence of detectable protein in CCR6- memory T cells (as opposed to CCR6+), therefore, presents a relevant baseline against which to compare Th-IL17 or Th-IL22 marker protein levels.

A variety of protocols are available for measuring and/or detecting expression levels of polypeptides. Protocols for detecting polypeptide expression, such as, for example, immunohistochemistry and immunoblotting, are known in the art. These protocols are generally applicable to detecting IL17, IL17F, IL23R, RORC, or IL22, polypeptides. Particular methods for detecting IL17, IL17F, IL23R, RORC, or IL22, polypeptides are described in the Examples presented herein, as are reagents for performing such methods.

In general, immunoassays for polypeptides typically comprise contacting a sample, such as a population of cells (e.g., incubated in Th17 or Th22 promoting conditions or lysates thereof) in the presence of an antibody that specifically or selectively binds to a polypeptide in question, e.g., a detectably labeled antibody capable of identifying, the particular polypeptide (e.g., IL-17 or IL-22), and detecting the bound antibody by any of a number of techniques well-known in the art (e.g., Western blot, ELISA, FACS).

The biological sample may be brought in contact with and immobilized onto a solid phase support or carrier such as nitrocellulose, or other solid support that is capable of immobilizing cells, cell particles or soluble proteins. The support may then be washed with suitable buffers followed by treatment with the detectably labeled antibody that selectively or specifically binds to the particular polypeptide (e.g., a Th17 or Th22 cell marker). The solid phase support may then be washed with the buffer a second time to remove unbound antibody. The amount of bound label on a solid support may then be detected by conventional means.

More particularly, Th-IL17 or Th-IL22 marker protein levels can be assessed by cell surface staining for CCR6 and IL23R; ELISA for IL-17, IL-17F, and IL-22; intracellular staining for IL17, IL17F, IL22, or RORC; and Western Blot for IL-17, IL-17F, IL23R, RORC, IL22.

By "solid phase support or carrier" is intended any support capable of binding an antigen or an antibody. Well-known supports or carriers include glass, polystyrene, polypropylene, polyethylene, dextran, nylon, amylases, natural and modified celluloses, polyacrylamides, gabbros, and magnetite. The nature of the carrier can be either soluble to some extent or insoluble for the purposes of the present invention. The support material may have virtually any possible structural configuration so long as the coupled molecule is capable of binding to an antigen or antibody. Thus, the support configuration may be spherical, as in a bead, or cylindrical, as in the inside surface of a test tube, or the external surface of a rod. Alternatively, the surface may be flat such as a sheet, test strip, etc. Particular supports include polystyrene beads. Those skilled in the art will know many other suitable carriers for binding antibody or antigen, or will be able to ascertain the same by use of routine experimentation.

An antibody can be detectably labeled by linking same to an enzyme and using the labeled antibody in an enzyme immunoassay (EIA) (Voller, *Diagnostic Horizons* 1978; 2:1, Microbiological Associates Quarterly Publication, Walkersville, Md.); Voller, et al., *J. Clin. Pathol.* 1978; 31: 507-520; Butler, Meth. Enzymol. 1981; 73:482; Maggio, (ed.), 1980, Enzyme Immunoassay, CRC Press, Boca Raton, Fla.; Ishikawa, E. et al., (eds.), 1981, Enzyme Immunoassay, Kgaku Shoin, Tokyo). The enzyme that is bound to the antibody reacts with an appropriate substrate, particularly a chromogenic substrate, in such a manner as to produce a chemical moiety detectable, for example, by spectrophotometric, fluorimetric or by visual means. Enzymes which can be used to detectably label the antibody include, but are not limited to, malate dehydrogenase, staphylococcal nuclease, delta-5-steroid isomerase, yeast alcohol dehydrogenase, alpha-glycerophosphate, dehydrogenase, triose phosphate isomerase, horseradish peroxidase, alkaline phosphatase, asparaginase, glucose oxidase, beta-galactosidase, ribonuclease, urease, catalase, glucose-6-phosphate dehydrogenase, glucoamylase and acetylcholinesterase. The detection can be accomplished by colorimetric methods that employ a chromogenic substrate for the enzyme. Detection may also be accomplished by visual comparison of the extent of enzymatic reaction of a substrate in comparison with similarly prepared standards.

Detection may also be accomplished using any of a variety of other immunoassays. For example, by radioactively labeling the antibodies or antibody fragments, it is possible to detect a polypeptide through the use of a radioimmunoassay (RIA). The radioactive isotope can be detected by such means as the use of a gamma counter or a scintillation counter or by autoradiography.

An antibody may also be labeled with a fluorescent compound. When the fluorescently labeled antibody is exposed to light of the proper wavelength, its presence can be detected due to fluorescence emission. Among the most commonly used fluorescent labeling compounds are fluorescein isothiocyanate, rhodamine, phycoerythrin, phycocyanin, allophycocyanin, o-phthaldehyde and fluorescamine.

An antibody can also be detectably labeled using fluorescence emitting metals such as $^{152}$Eu, or others of the lanthanide series. These metals can be attached to the antibody using such metal chelating groups as diethylenetriaminepentacetic acid (DTPA) or ethylene diaminetetraacetic acid (EDTA).

An antibody can also be detectably labeled by coupling it to a chemiluminescent compound. The presence of the chemiluminescent-tagged antibody is determined by detecting the presence of luminescence that arises during the course of a chemical reaction. Examples of particularly useful chemiluminescent labeling compounds are luminol, isoluminol, theromatic acridinium ester, imidazole, acridinium salt and oxalate ester.

Likewise, a bioluminescent compound may be used to label an antibody. Bioluminescence is a type of chemiluminescence found in biological systems in which a catalytic protein increases the efficiency of the chemiluminescent reaction. The presence of a bioluminescent protein is determined by detecting the presence of luminescence. Important bioluminescent compounds for purposes of labeling are luciferin, luciferase and aequorin.

The basic molecular biology techniques used to practice the methods of the invention are well known in the art, and are described for example in Sambrook et al., 1989, *Molecular Cloning: A Laboratory Manual*, Cold Spring Harbor Laboratory, New York; Ausubel et al., 1988, *Current Protocols in Molecular Biology*, John Wiley & Sons, New York; and Ausubel et al., 2002, *Short Protocols in Molecular Biology*, John Wiley & Sons, New York).

Agents Identified by the Screening Methods of the Invention

The invention provides methods for identifying agents (e.g., candidate compounds or test compounds) that modulate (inhibit or promote) human Th-IL17+ or Th-IL22+ function upon activation. Agents that are capable of inhibiting human Th-IL17+ or Th-IL22+ function upon activation, as identified by the screening method of the invention, are useful as candidate anti-inflammatory or anti-autoimmune disorder therapeutics.

A list of inflammatory or anti-autoimmune disorders that may be treated using an agent identified using a method of the invention includes, without limitation: arthritis, diabetes, multiple sclerosis, uveitis, rheumatoid arthritis, psoriasis, osteoporosis, asthma, bronchitis, allergic rhinitis, chronic obstructive pulmonary disease, atherosclerosis, *H. pylori* infections and ulcers resulting from such infection, graft versus host disease following bone marrow transplantation, and inflammatory bowel diseases. Inflammatory bowel diseases treatable using agents identified by the present methods include Crohn's disease, ulcerative colitis, sprue and food allergies. An inflammatory disease or condition may involve any organ or tissue in which the presence of Th17 or Th22 cells has been demonstrated and/or implicated in disease etiology. Other diseases known to produce immunopathological damage in the host, which may benefit from treatment with an agent identified using a method of the invention, may be selected from the group consisting of Hepatitis C virus, Influenza, SARS, and respiratory syncytial virus. The involvement of $T_H17$ or Th22 related genes autotoxin and maspin also suggests that prostate and breast cancers may be treated using an agent identified using a method of the invention. Evidence that the balance of Th17 or Th22 and Treg cells is specifically altered in human immunodeficiency virus (HIV) infections also suggests that immunodeficiencies and HIV infection may be treated using an agent identified using a method of the invention.

Examples of agents, candidate compounds or test compounds include, but are not limited to, nucleic acids (e.g., DNA and RNA), carbohydrates, lipids, proteins, peptides, peptidomimetics, small molecules and other drugs. Agents can be obtained using any of the numerous approaches in combinatorial library methods known in the art, including: biological libraries; spatially addressable parallel solid phase or solution phase libraries; synthetic library methods requiring deconvolution; the "one-bead one-compound" library method; and synthetic library methods using affinity chromatography selection. The biological library approach is limited to peptide libraries, while the other four approaches are applicable to peptide, non-peptide oligomer or small molecule libraries of compounds (Lam, *Anticancer Drug Des.* 1997; 12:145; U.S. Pat. No. 5,738,996; and U.S. Pat. No. 5,807,683, each of which is incorporated herein in its entirety by reference).

Examples of methods for the synthesis of molecular libraries can be found in the art, for example in: DeWitt, et al., *Proc. Natl. Acad. Sci. USA* 1993; 90:6909; Erb, et al., *Proc. Natl. Acad. Sci. USA* 1994; 91:11422; Zuckermann, et al., *J. Med. Chem.* 1994; 37:2678; Cho, et al., *Science* 1993; 261:1303; Carrell, et al., *Angew. Chem. Int. Ed. Engl.* 1994; 33:2059; Carell, et al., *Angew. Chem. Int. Ed. Engl.* 1994; 33:2061; and Gallop, et al., *J. Med. Chem.* 1994; 37:1233, each of which is incorporated herein in its entirety by reference.

Libraries of compounds may be presented, e.g., presented in solution (e.g., Houghten, *Bio/Techniques* 1992; 13:412-421), or on beads (Lam, *Nature* 1991; 354:82-84), chips (Fodor, *Nature* 1993; 364:555-556), bacteria (U.S. Pat. No. 5,223,409), spores (U.S. Pat. Nos. 5,571,698; 5,403,484; and 5,223,409), plasmids (Cull, et al., *Proc. Natl. Acad. Sci. USA* 1992; 89:1865-1869) or phage (Scott, et al., *Science* 1990; 249:386-390; Devlin, *Science* 1990; 249:404-406; Cwirla, et al., *Proc. Natl. Acad. Sci. USA* 1990; 87:6378-6382; and Felici, *J. Mol. Biol.* 1991; 222:301-310), each of which is incorporated herein in its entirety by reference.

Therapeutic Uses of Agents Identified

The invention provides for treatment of inflammatory and/or autoimmune disorders by administration of a therapeutic agent identified using the above-described methods. Such agents include, but are not limited to proteins, peptides, protein or peptide derivatives or analogs, antibodies, nucleic acids, and small molecules.

The invention provides methods for treating patients afflicted with an inflammatory and/or autoimmune disorder comprising administering to a subject an effective amount of a compound identified by the method of the invention. In a particular aspect, the compound is substantially purified (e.g., substantially free from substances that limit its effect or produce undesired side-effects). The subject is particularly an animal, including but not limited to animals such as cows, pigs, horses, chickens, cats, dogs, etc., and is more particularly a mammal, and most particularly a human. In a specific embodiment, a non-human mammal is the subject.

Formulations and methods of administration that can be employed when the compound comprises a nucleic acid are described above; additional appropriate formulations and routes of administration are described below.

Various delivery systems are known and can be used to administer a compound of the invention, e.g., encapsulation in liposomes, microparticles, microcapsules, recombinant cells capable of expressing the compound, receptor-mediated endocytosis (see, e.g., Wu, et al., *J. Biol. Chem.* 1987; 262:

4429-4432), and construction of a nucleic acid as part of a retroviral or other vector. Methods of introduction can be enteral or parenteral and include but are not limited to intradermal, intramuscular, intraperitoneal, intravenous, subcutaneous, intranasal, epidural, and oral routes. The compounds may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local. In addition, it may be desirable to introduce the pharmaceutical compositions of the invention into the central nervous system by any suitable route, including intraventricular and intrathecal injection; intraventricular injection may be facilitated by an intraventricular catheter, for example, attached to a reservoir, such as an Ommaya reservoir. Pulmonary administration can also be employed, e.g., by use of an inhaler or nebulizer, and formulation with an aerosolizing agent.

In a specific embodiment, it may be desirable to administer the pharmaceutical compositions of the invention locally, e.g., by local infusion during surgery, topical application, e.g., by injection, by means of a catheter, or by means of an implant, said implant being of a porous, non-porous, or gelatinous material, including membranes, such as sialastic membranes, or fibers.

In another embodiment, the compound can be delivered in a vesicle, in particular a liposome (see Langer, *Science* 1990; 249:1527-1533; Treat et al., in *Liposomes in the Therapy of Infectious Disease and Cancer*, Lopez-Berestein and Fidler (eds.), Liss, New York, pp. 353-365 (1989); Lopez-Berestein, ibid., pp. 317-327; see generally ibid.)

In yet another embodiment, the compound can be delivered in a controlled release system. In one embodiment, a pump may be used (see Langer, supra; Sefton *CRC Crit. Ref Biomed. Eng.* 1987; 14:201; Buchwald, et al., *Surgery* 1980; 88:507; Saudek, et al., *N. Engl. J. Med.* 1989; 321:574). In another embodiment, polymeric materials can be used (see Medical Applications of Controlled Release, Langer and Wise (eds.), CRC Pres., Boca Raton, Fla. (1974); Controlled Drug Bioavailability, Drug Product Design and Performance, Smolen and Ball (eds.), Wiley, New York (1984); Ranger, et al., *Macromol. Sci. Rev. Macromol. Chem.* 1983; 23:61; see also Levy, et al., *Science* 1985; 228:190; During, et al., *Ann. Neurol.* 1989; 25:351; Howard, et al., *J. Neurosurg.* 1989; 71:105). In yet another embodiment, a controlled release system can be placed in proximity of the therapeutic target, e.g., an inflammatory site, thus requiring only a fraction of the systemic dose (see, e.g., Goodson, in Medical Applications of Controlled Release, supra, 1984; 2:115-138). Other controlled release systems are discussed in the review by Langer, *Science* 1990; 249:1527-1533).

Pharmaceutical Compositions

The present invention also provides pharmaceutical compositions. Such compositions comprise a therapeutically effective amount of an agent and a pharmaceutically acceptable carrier. In a particular embodiment, the term "pharmaceutically acceptable" means approved by a regulatory agency of the federal or a state government or listed in the U.S. Pharmacopeia or other generally recognized pharmacopeia for use in animals, and more particularly in humans. The term "carrier" refers to a diluent, adjuvant, excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions.

Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents. These compositions can take the form of solutions, suspensions, emulsion, tablets, pills, capsules, powders, sustained-release formulations and the like. The composition can be formulated as a suppository, with traditional binders and carriers such as triglycerides. Oral formulation can include standard carriers such as pharmaceutical grades of mannitol, lactose, starch, magnesium stearate, sodium saccharine, cellulose, magnesium carbonate, etc. Examples of suitable pharmaceutical carriers are described in "Remington's Pharmaceutical Sciences" by E. W. Martin, incorporated in its entirety by reference herein. Such compositions will contain a therapeutically effective amount of the compound, preferably in purified form, together with a suitable amount of carrier so as to provide the form for proper administration to the subject. The formulation should suit the mode of administration.

In a particular embodiment, the composition is formulated in accordance with routine procedures as a pharmaceutical composition adapted for intravenous administration to human beings. Typically, compositions for intravenous administration are solutions in sterile isotonic aqueous buffer. Where necessary, the composition may also include a solubilizing agent and a local anesthetic such as lidocaine to ease pain at the site of the injection. Generally, the ingredients are supplied either separately or mixed together in unit dosage form, for example, as a dry lyophilized powder or water free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

The compounds of the invention can be formulated as neutral or salt forms. Pharmaceutically acceptable salts include those formed with free amino groups such as those derived from hydrochloric, phosphoric, acetic, oxalic, tartaric acids, etc., and those formed with free carboxyl groups such as those derived from sodium, potassium, ammonium, calcium, ferric hydroxides, isopropylamine, triethylamine, 2-ethylamino ethanol, histidine, procaine, etc.

The amount of the compound of the invention which will be effective in the treatment of an inflammatory or autoimmune disorder (e.g., Crohn's disease) can be determined by standard clinical techniques based on the present description. In addition, in vitro assays may optionally be employed to help identify optimal dosage ranges. The precise dose to be employed in the formulation will also depend on the route of administration, and the seriousness of the disease or disorder, and should be decided according to the judgment of the practitioner and each subject's circumstances. However, suitable dosage ranges for intravenous administration are generally about 20-500 micrograms of active compound per kilogram body weight. Suitable dosage ranges for intranasal administration are generally about 0.01 pg/kg body weight to 1 mg/kg body weight. Suppositories generally contain active ingredient in the range of 0.5% to 10% by weight; oral formulations preferably contain 10% to 95% active ingredient. Effective doses may be extrapolated from dose-response curves derived from in vitro or animal model test systems.

Nucleic Acids

The invention provides methods of identifying agents capable of modulating human Th-IL17+ or Th-IL22+ cell function and activation. Accordingly, the invention encompasses administration of a nucleic acid encoding a peptide or protein capable of modulating human Th-IL17+ or Th-IL22+ cell function and activation, as well as antisense sequences or catalytic RNAs capable of interfering with human Th-IL17+ or Th-IL22+ cell function.

Any suitable methods for administering a nucleic acid sequence available in the art can be used according to the present invention.

Methods for administering and expressing a nucleic acid sequence are generally known in the area of gene therapy. For general reviews of the methods of gene therapy, see Goldspiel, et al., *Clinical Pharmacy* 1993; 12:488-505; Wu, et al. *Biotherapy* 1991; 3:87-95; Tolstoshev, *Ann. Rev. Pharmacol. Toxicol.* 1993; 32:573-596; Mulligan, *Science* 1993; 260: 926-932; and Morgan, et al., *Ann. Rev. Biochem.* 1993; 62:191-217; May, *TIBTECH* 1993; 11(5): 155-215. Methods commonly known in the art of recombinant DNA technology which can be used in the present invention are described in Ausubel et al. (eds.), 1993, Current Protocols in Molecular Biology, John Wiley & Sons, NY; and Kriegler (1990) Gene Transfer and Expression, A Laboratory Manual, Stockton Press, NY.

In a particular aspect, the compound comprises a nucleic acid encoding a peptide or protein capable of modulating human Th-IL17+ or Th-IL22+ cell function and activation, such nucleic acid being part of an expression vector that expresses the peptide or protein in a suitable host. In particular, such a nucleic acid has a promoter operably linked to the coding region, said promoter being inducible or constitutive (and, optionally, tissue-specific). In another particular embodiment, a nucleic acid molecule is used in which the coding sequences and any other desired sequences are flanked by regions that promote homologous recombination at a desired site in the genome, thus providing for intrachromosomal expression of the nucleic acid (Koller, et al., *Proc. Natl. Acad. Sci. USA* 1989; 86:8932-8935; Zijlstra, et al., *Nature* 1989; 342:435-438).

Delivery of the nucleic acid into a subject may be direct, in which case the subject is directly exposed to the nucleic acid or nucleic acid-carrying vector; this approach is known as in vivo gene therapy. Alternatively, delivery of the nucleic acid into the subject may be indirect, in which case cells are first transformed with the nucleic acid in vitro and then transplanted into the subject, known as "ex vivo gene therapy".

In another embodiment, the nucleic acid is directly administered in vivo, where it is expressed to produce the encoded product. This can be accomplished by any of numerous methods known in the art, e.g., by constructing it as part of an appropriate nucleic acid expression vector and administering it so that it becomes intracellular, e.g., by infection using a defective or attenuated retroviral or other viral vector (see U.S. Pat. No. 4,980,286); by direct injection of naked DNA; by use of microparticle bombardment (e.g., a gene gun; Biolistic, Dupont); by coating with lipids, cell-surface receptors or transfecting agents; by encapsulation in liposomes, microparticles or microcapsules; by administering it in linkage to a peptide which is known to enter the nucleus; or by administering it in linkage to a ligand subject to receptor-mediated endocytosis (see, e.g., Wu, et al., *J. Biol. Chem.* 1987; 262:4429-4432), which can be used to target cell types specifically expressing the receptors.

In another embodiment, a nucleic acid-ligand complex can be formed in which the ligand comprises a fusogenic viral peptide to disrupt endosomes, allowing the nucleic acid to avoid lysosomal degradation. In yet another embodiment, the nucleic acid can be targeted in vivo for cell specific uptake and expression, by targeting a specific receptor (see, e.g., PCT Publications WO 92/06180 dated Apr. 16, 1992 (Wu et al.); WO 92/22635 dated Dec. 23, 1992 (Wilson et al.); WO92/20316 dated Nov. 26, 1992 (Findeis et al.); WO93/14188 dated Jul. 22, 1993 (Clarke et al.), WO 93/20221 dated Oct. 14, 1993 (Young)). Alternatively, the nucleic acid can be introduced intracellularly and incorporated within host cell DNA for expression, by homologous recombination (Koller, et al., *Proc. Natl. Acad. Sci. USA* 1989; 86:8932-8935; Zijlstra, et al., *Nature* 1989; 342:435-438).

In a further embodiment, a retroviral vector can be used (see Miller, et al., *Meth. Enzymol.* 1993; 217:581-599). These retroviral vectors have been modified to delete retroviral sequences that are not necessary for packaging of the viral genome and integration into host cell DNA. The nucleic acid encoding a desired polypeptide to be used in gene therapy is cloned into the vector, which facilitates delivery of the gene into a subject. More detail about retroviral vectors can be found in Boesen, et al., *Biotherapy* 1994; 6:291-302, which describes the use of a retroviral vector to deliver the mdr1 gene to hematopoietic stem cells in order to make the stem cells more resistant to chemotherapy. Other references illustrating the use of retroviral vectors in gene therapy are: Clowes, et al., *J. Clin. Invest.* 1994; 93:644-651; Kiem, et al., *Blood* 1994; 83:1467-1473; Salmons, et al., *Human Gene Therapy* 1993; 4:129-141; and Grossman, et al., *Curr. Opin. in Genetics and Devel.* 1993; 3:110-114.

Adenoviruses may also be used effectively in gene therapy. Adenoviruses are especially attractive vehicles for delivering genes to respiratory epithelia. Adenoviruses naturally infect respiratory epithelia where they cause a mild disease. Other targets for adenovirus-based delivery systems are liver, the central nervous system, endothelial cells, and muscle. Adenoviruses have the advantage of being capable of infecting non-dividing cells. Kozarsky, et al., *Current Opinion in Genetics and Development* 1993; 3:499-503 present a review of adenovirus-based gene therapy. Bout, et al., *Human Gene Therapy* 1994; 5:3-10 demonstrated the use of adenovirus vectors to transfer genes to the respiratory epithelia of rhesus monkeys. Other instances of the use of adenoviruses in gene therapy can be found in Rosenfeld. et al., *Science* 1991; 252:431-434; Rosenfeld, et al., *Cell* 1992; 68:143-155; Mastrangeli, et al., *J. Clin. Invest.* 1993; 91:225-234; PCT Publication WO94/12649; and Wang, et al., *Gene Therapy* 1995; 2:775-783. Adeno-associated virus (AAV) has also been proposed for use in gene therapy (Walsh, et al., *Proc. Soc. Exp. Biol. Med.* 1993; 204:289-300; U.S. Pat. No. 5,436,146).

Another suitable approach to gene therapy involves transferring a gene to cells in tissue culture by such methods as electroporation, lipofection, calcium phosphate mediated transfection, or viral infection. Usually, the method of transfer includes the transfer of a selectable marker to the cells. The cells are then placed under selection to isolate those cells that have taken up and are expressing the transferred gene. Those cells are then delivered to a subject.

In this embodiment, the nucleic acid is introduced into a cell prior to administration in vivo of the resulting recombinant cell. Such introduction can be carried out by any method known in the art, including but not limited to transfection, electroporation, microinjection, infection with a viral or bacteriophage vector containing the nucleic acid sequences, cell fusion, chromosome-mediated gene transfer, microcell-mediated gene transfer, spheroplast fusion, etc. Numerous techniques are known in the art for the introduction of foreign genes into cells (see, e.g., Loeffler, et al., *Meth. Enzymol.* 1993; 217:599-618; Cohen, et al., *Meth. Enzymol.* 1993; 217: 618-644; Cline, *Pharmac. Ther.* 1985; 29:69-92) and may be used in accordance with the present invention, provided that the necessary developmental and physiological functions of the recipient cells are not disrupted. The technique should provide for the stable transfer of the nucleic acid to the cell, so that the nucleic acid is expressible by the cell and preferably heritable and expressible by its cell progeny.

The resulting recombinant cells can be delivered to a subject by various methods known in the art. In a particular embodiment, epithelial cells are injected, e.g., subcutaneously. In another embodiment, recombinant skin cells may be applied as a skin graft onto the subject; recombinant blood cells (e.g., hematopoietic stem or progenitor cells) are preferably administered intravenously. The amount of cells envisioned for use depends on the desired effect, the condition of the subject, etc., and can be determined by one skilled in the art.

Cells into which a nucleic acid can be introduced for purposes of gene therapy encompass any desired, available cell type, and include but are not limited to neuronal cells, glial cells (e.g., oligodendrocytes or astrocytes), epithelial cells, endothelial cells, keratinocytes, fibroblasts, muscle cells, hepatocytes; blood cells such as T lymphocytes, B lymphocytes, monocytes, macrophages, neutrophils, eosinophils, megakaryocytes, granulocytes; various stem or progenitor cells, in particular hematopoietic stem or progenitor cells, e.g., as obtained from bone marrow, umbilical cord blood, peripheral blood or fetal liver. In a particular embodiment, the cell used for gene therapy is autologous to the subject that is treated.

In another embodiment, the nucleic acid to be introduced for purposes of gene therapy may comprise an inducible promoter operably linked to the coding region, such that expression of the nucleic acid is controllable by adjusting the concentration of an appropriate inducer of transcription.

Direct injection of a DNA coding for a peptide or protein capable of modulating human Th-IL17+ or Th-IL22+ cell function and activation may also be performed according to, for example, the techniques described in U.S. Pat. No. 5,589, 466. These techniques involve the injection of "naked DNA", i.e., isolated DNA molecules in the absence of liposomes, cells, or any other material besides a suitable carrier. The injection of DNA encoding a protein and operably linked to a suitable promoter results in the production of the protein in cells near the site of injection.

Unless defined otherwise, all technical and scientific terms used herein have the same meaning as commonly understood by one of ordinary skill in the art to which this invention belongs.

It is to be understood that this invention is not limited to particular assay methods, or test agents and experimental conditions described, as such methods and agents may vary. It is also to be understood that the terminology used herein is for the purpose of describing particular embodiments only, and is not intended to be limiting, since the scope of the present invention will be limited only the appended claims.

Discussion

Th17-signature cytokines, particularly IL-17 and IL-22, are dynamically regulated within human $CCR6^+$ memory T cells by γc-cytokine signals. IL-17 and IL-22 expression by $CCR6^+$ $T_M$ cells is controlled by PI-3K/Akt-dependent signaling that involves the repression of both FOXO1 and KLF2. CCR6 expression on non-regulatory (i.e. $CD25^-$) memory T cells broadly defines lineage-committed Th17 cells; phenotypically diverse sub-populations of $CCR6^+$ (e.g., $CD161^{+/-}$, $CXCR3^{+/-}$) $T_M$ cells all share a capacity to express Th17 cytokines in response to γc-cytokine stimulation, irrespective of whether or not they express IL-17 ex vivo. Importantly, the specific conversion of ex vivo-isolated $CCR6^+IL-17^-$, but not $CCR6^- IL-17^-$ memory T cells is conserved in mice (FIG. 8). Taken together, these results indicate that IL-17 and IL-22 production by $CCR6^+$ $T_M$ cells may be influenced in a bystander fashion by γc-cytokines present at sites of inflammation or infection.

Figure 1C:
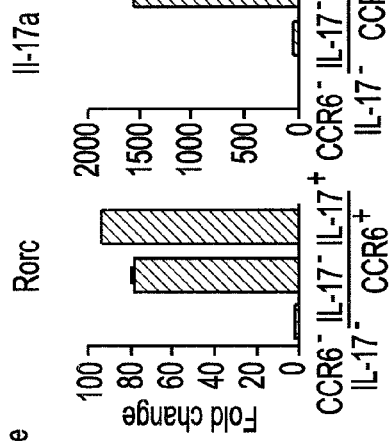
Figure 1D:
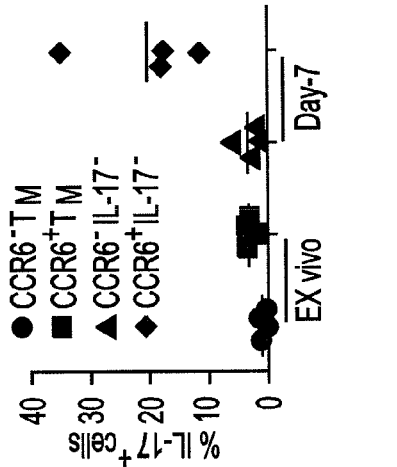
Figure 1E:
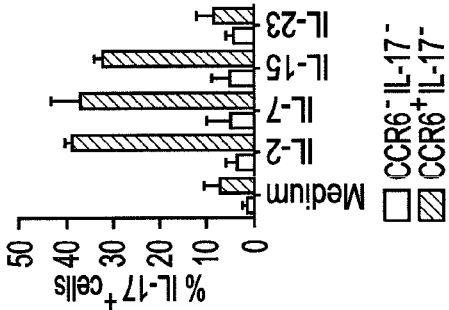
Figure 1F:
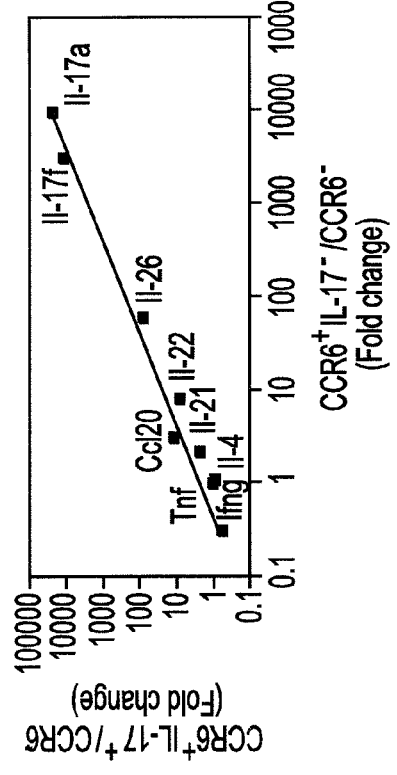
Figure 2A:
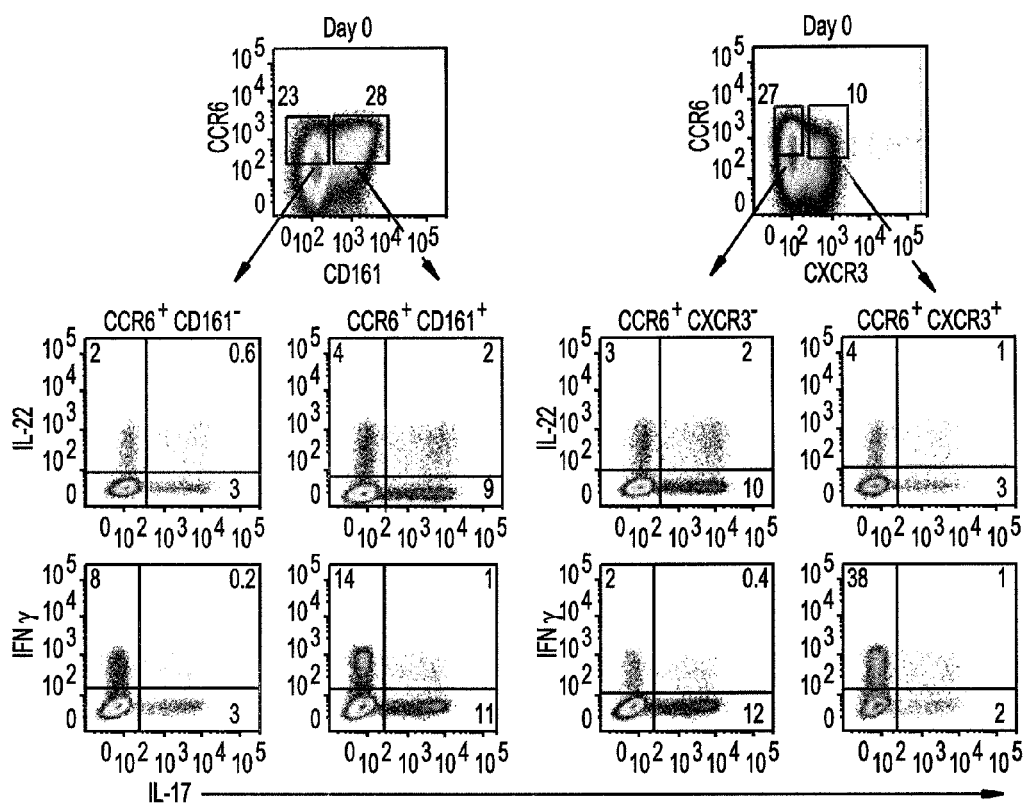
FIG. 2 demonstrates IL-17 induction in response to γc-cytokine stimulation is a conserved feature shared by heterogeneous CCR6$^+$ T$_M$ cell subsets. (a) Ex vivo (day 0) isolated CD4$^+$ T$_M$ cells were co-stained with CCR6, CD161, and CXCR3. The frequency of CCR6$^+$ cells positive or negative for either CD161 (left), or CXCR3 (right) are shown. Ex vivo cytokine production was determined following PMA and ionomycin stimulation within each gated CCR6$^+$ T$_M$ cell subset as indicated. FACS plots show the intracellular expression of IL-17, IL-22, and IFNγ. (b) FACS sorted CCR6$^-$IL-17$^-$, CCR6$^+$CD161$^{+/-}$IL-17$^-$ (left) or CCR6$^+$CXCR3$^{+/-}$ IL-17$^-$ (right) cells were cultured in IL-2-supplemented medium for 7 days and restimulated with PMA and ionomycin. Cytokine production was determined by intracellular staining for IL-17, IL-22, and IFNγ. Each set of data is representative of three donors.
Figure 2B:
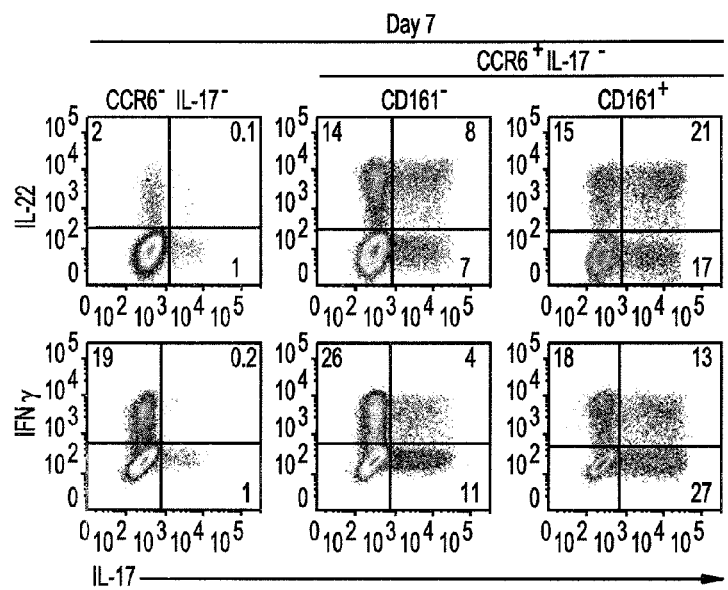
Figure 2C:
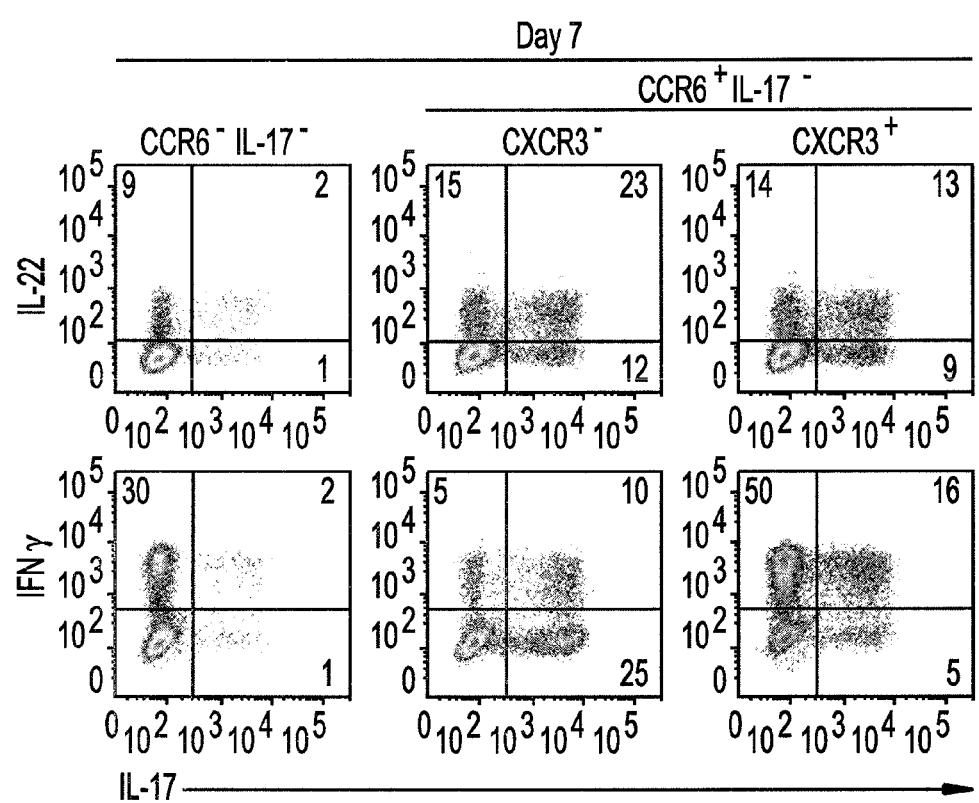

These results also indicate that current methods of calculating Th17 cell frequencies based solely on ex vivo IL-17 production may not represent the true size or inflammatory potential of the human Th17 memory cell compartment. This becomes particularly important for how Th17 cells are evaluated and quantified in clinical disease settings. Indeed, a substantial portion of $CCR6^+$, but not $CCR6^-$, $IL-17^-$ $T_M$ cells isolated ex vivo from the peripheral blood of rheumatoid arthritis (RA) patients convert into IL-17-producers upon culture with γc-cytokines (FIG. 1f).

Figure 9A:
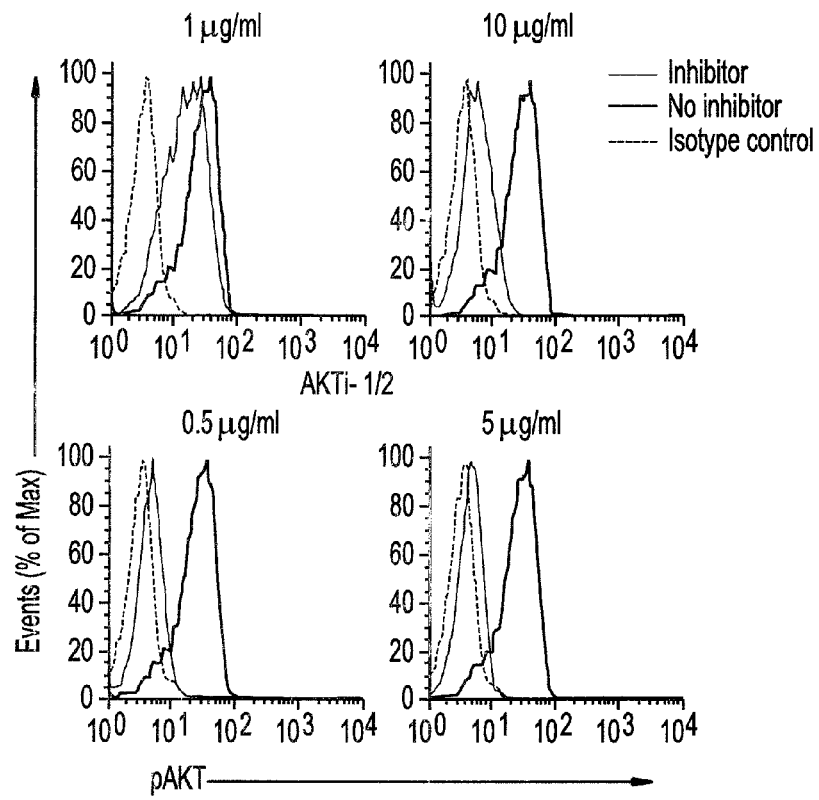
Figure 9B:
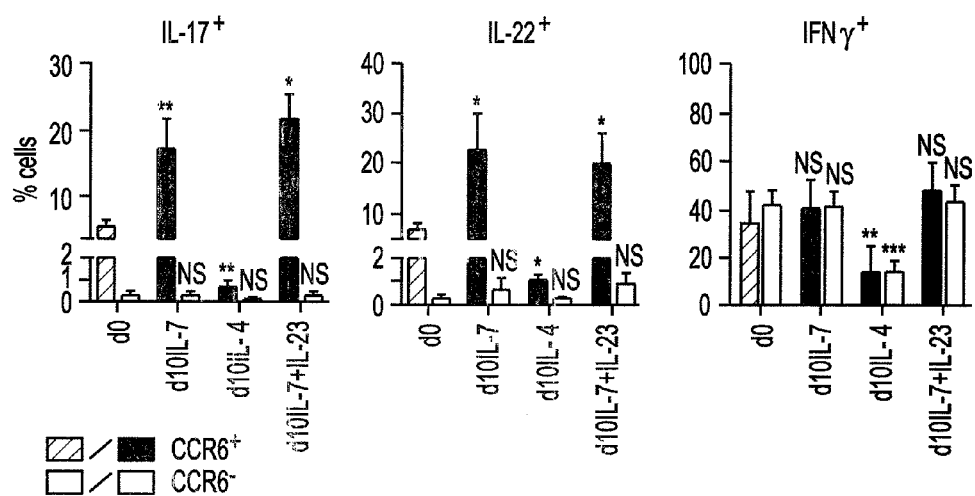
Figure 9C:
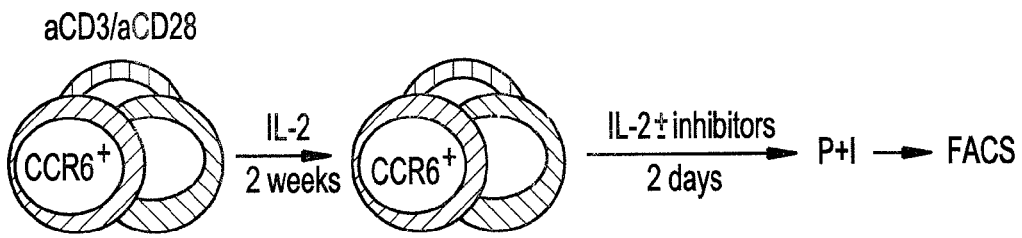
Figure 9D:
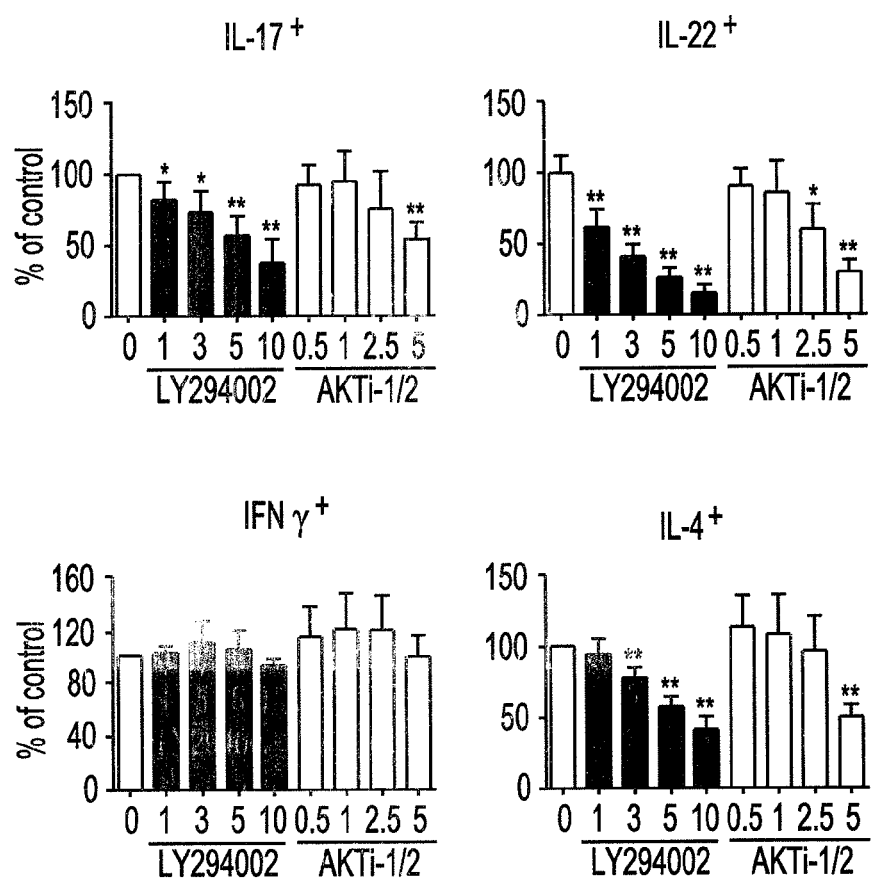
Figure 9E:
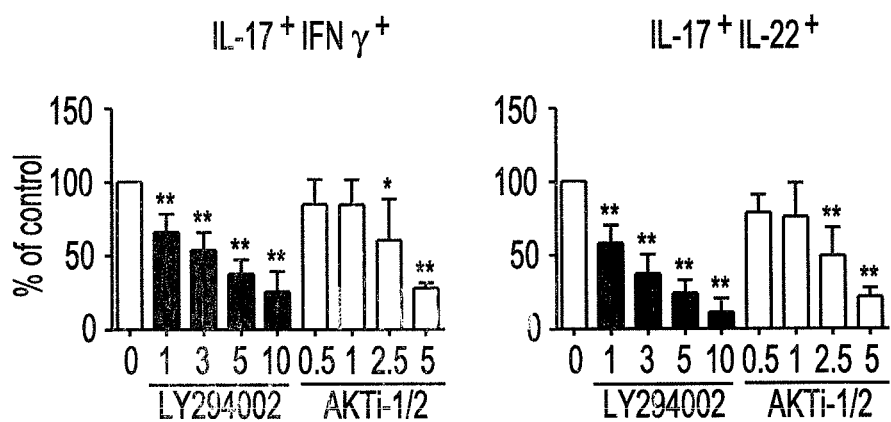
Figure 9F:
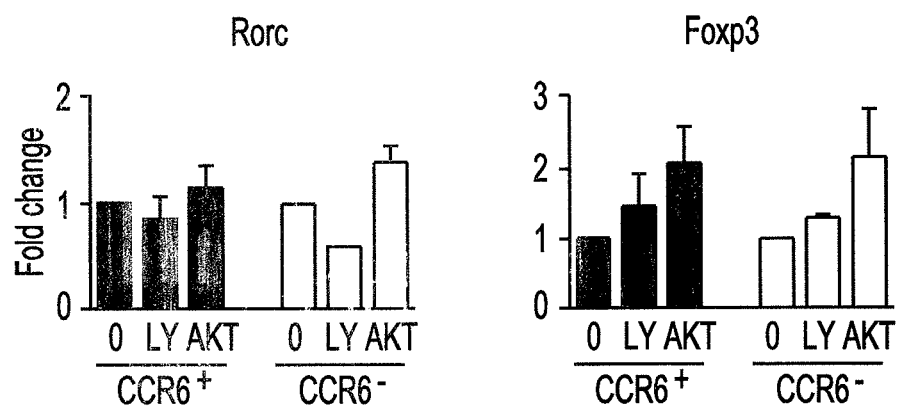

The ability of $CCR6^+$ $T_M$ cells to express IL-17 may be due to the fact that, in contrast to $CCR6^-$ $T_M$ cells, $CCR6^+$ cells express high levels of RORC ex vivo, independent of IL-17. This is indeed likely given that ectopic expression of RORC can induce IL-17 expression in $CCR6^-$ $T_M$ cells (FIG. 6) (Manel, et al., *Nature Immunology* 2008; 9: 641-649). These findings further indicate that RORC is necessary, but not sufficient, for IL-17 production by human memory T cells. RORC synergizes with γc-mediated PI-3K and Akt signaling to trans-activate IL-17 expression. Two additional results support a model in which γc-cytokine signaling acts together with RORC to control IL-17 production per se, as opposed to regulating Th17 lineage commitment. First, neither IL-7 stimulation, nor treatment with PI-3K or Akt inhibitors, nor overexpression of FOXO1 or KLF2 affected RORC mRNA expression levels (FIG. 9f, and unpublished data). Second, inhibition of IL-17 and IL-22 expression by treatment with LY294002 was completely reversible (unpublished data).

IL-23 is another cytokine thought to be important for the stability and pro-inflammatory functions of Th17 cells, particularly in the mouse (Zheng, et al., *Nature* 2007; 445: 648-651; Zhou, et al., *Nature Immunology* 2007; 8: 967-974). However, IL-23 is not able to compensate for γc cytokines in the induction of IL-17/IL-22 expression from $CCR6^+$ human $T_M$ cells, even though these cells expressed Il23R mRNA (unpublished data). Conceivably, IL-23 could enhance IL-17-secreting cells but this effect may be attributed to preferential expansion of $CCR6^+IL-23R^+$ $T_M$ cells that are more likely to express IL-17 upon TCR triggering. A more dominant role of IL-23 in driving IL-17-associated pathology is through its reported effects on IL-17 expression within TCRγ/δ lymphocytes, or other innate immune cells (Moens, et al., *Journal of Leukocyte Biology* 2011).

PI-3K is activated in T cells in response to TCR engagement or γc-cytokine stimulation (Rochman, et al., *Nature Reviews* 2009; 9: 480-490; Smith-Garvin, et al., *Annual review of Immunology* 2009; 27: 591-619), which in-turn results in the phosphorylation and activation of Akt (Coffer, et al., *Biochem J* 1998; 335 (Pt 1): 1-13). On one hand, PI-3K/Akt signaling positively regulates cell metabolism through activation of mTORC1 (Gibbons, et al., *Semin Oncol* 2009; 3: S3-S17). On the other hand, activated Akt also inhibits the transcriptional activity or expression of FOXO1 or KLF2, respectively (Fabre, et al., *J Immunology* 2008; 181: 2980-

2989; Sinclair, et al., *Nature Immunology* 2008; 9: 513-521). Induction of IL-17 and IL-22 expression by γc-cytokines was reversed by short-term (48 hour) treatment with PI-3K or Akt inhibitors. Furthermore, overexpression of either FOXO1 or KLF2 recapitulated the effects of the PI-3K or Akt inhibitors on IL-17 and IL-22 induction. Conversely, shRNA-mediated silencing of endogenous KLF2 enhanced IL-17 and IL-22 expression by $CCR6^+$ $T_M$ or RORC-expressing $CCR6^-$ $T_M$ cells. We therefore conclude that γc-dependent activation of PI-3K and Akt drives expression of IL-17 and IL-22, preferentially through a pathway that involves FOXO1 and KLF2 downmodulation (FIG. 12) (Barata, et al., *J Exp Med* 2004; 200: 659-669; Brunet, et al., *Cell* 1999; 96: 857-868; Fabre, et al., *J Immunology* 2008; 181: 2980-2989; Fabre, et al., *Journal of Immunology* 2005; 174: 4161-4171; Sinclair, et al., *Nature Immunology* 2008; 9: 513-521). However, as rapamycin treatment (Kopf, et al., *International Immunopharmacology* 2007; 7: 1819-1824), and mTOR-deficiency (Delgoffe, et al., *Immunity* 2009; 30: 832-844; Delgoffe, et al., *Nature Immunology* 2011; 12: 295-303) have been reported to negatively regulate Th17 differentiation and activation in naïve mouse T cells, it will be of interest to determine whether mTOR signaling also controls Th17-signature cytokine production in human $CCR6^+$ $T_M$ cells.

The mechanism by which FOXO1 and KLF2 negatively regulate IL-17 and IL-22 expression in human $T_M$ cells is uncertain. Both FOXO1 and KLF2 may function non-redundantly as transcriptional repressors of IL-17 and IL-22 (FIG. 12). However, FOXO1 may regulate IL-17/IL-22 expression indirectly by inducing KLF2 expression. Indeed, previous studies have shown that genetic ablation of Foxo1 leads to downregulation of Klf2 expression (Fabre, et al., *J Immunology* 2008; 181: 2980-2989; Kerdiles, et al., *Nature Immunology* 2009; 10: 176-184; Sinclair, et al., *Nature Immunology* 2008; 9: 513-521). In line with these reports, lentiviral overexpression of FOXO1 in human $T_M$ cells led to increased Klf2 expression (unpublished data).

The negative regulation of IL-17 and IL-22 expression represents a novel function of KLF2. Kruppel-like factors (KLFs) are a large family of zinc-finger transcription factors (Kaczynski, et al., *Genome Biol* 2003; 4: 206; van Vliet, et al., *Genomics* 2006; 87: 474-482); they play important roles in cell cellular differentiation and activation and homeostasis (Atkins, et al., *Circulation Research* 2007; 100: 1686-1695; Jiang, et al. *Nature Cell Biology* 2008; 10: 353-360; Kuo, et al., *Science* (New York, N.Y.) 1997b; 277: 1986-1990; Wani, et al., *The Journal of Biological Chemistry* 1999; 274: 21180-21185; Yamada, et al., *Nature Immunology* 2009; 10: 618-626; Yusuf, et al., *International Immunology* 2008; 20: 671-681). KLF2 specifically has been reported to maintain naïve T cell quiescence and survival in the mouse (Anderson, et al., *Mol Cell Biol* 1995; 15: 5957-5965; Buckley, et al., *Nature Immunology* 2001; 2: 698-704; Di Santo *Nature Immunology* 2001; 2: 667-668; Jiang, et al. *Nature Cell Biology* 2008; 10: 353-360; Kuo, et al., *Annual Review of Immunology* 1999; 17: 149-187; Kuo, et al., *Genes Dev* 1997a; 11: 2996-3006; Kuo, et al., *Science* (New York, N.Y.) 1997b; 277: 1986-1990; Wani, et al., *Transgenic Res* 1998; 7: 229-238; Wani, et al., *The Journal of Biological Chemistry* 1999; 274: 21180-21185; Yamada, et al., *Nature Immunology* 2009; 10: 618-626). It also regulates T cell emigration from the thymus (Carlson, et al., *Nature* 2006; 442: 299-302; Sebzda, et al., *Nature Immunology* 2008; 9: 292-300) through regulation of Sphingosine-1 phosphate-1 receptor (S1P1), CD62L, and the chemokine receptor CCR7 (Carlson, et al., *Nature* 2006; 442: 299-302; Sebzda, et al., *Nature Immunology* 2008; 9: 292-300); Weinreich, et al., *Immunity* 2009; 31: 122-130). T cells from Klf2-deficient mice display enhanced production of IL-4 (Weinreich, et al., *Nature Immunology* 2010; 11: 709-716; Weinreich, et al., *Immunity* 2009; 31: 122-130). In support of these findings, slightly elevated IL-4 production from $CCR6^+$ $T_M$ cells was observed following shRNA-mediated KLF2 silencing. Moreover, statins (HMG-CoA reductase inhibitors), which are clinically used to treat atherosclerosis, have also been shown to induce KLF2 expression (Parmar, et al., *The Journal of Biological Chemistry* 2005; 280: 26714-26719). More recently, statins have been found to be broadly anti-inflammatory and capable of repressing IL-17 secretion (Zhang, et al., *J Immunol* 2008; 180: 6988-6996).

These data indicate that human $CCR6^+$ $T_M$ cells represent a broad, pro-inflammatory, effector lineage that express IL-17 and IL-22 in a dynamic manner relying on synergy between γc-cytokine signaling and RORC. Local immune responses and subsequent accumulation of γc-cytokines may thus contribute to Th17/Th22-driven inflammation, which may be sensitive to PI-3K- or Akt-targeted therapies. Moreover, these data demonstrate that ex vivo analyses of IL-17 and IL-22 secretion may vastly underestimate the true frequency and pro-inflammatory potential of Th17/Th22 cells in vivo. These results shed new light of the regulation of pro-inflammatory cytokine production by human memory T cells, and also call for a broader phenotypic definition of Th17/Th22 subsets within both healthy human donors and autoimmune patient populations.

Example 1

Materials and Methods

Human T Cell Purification and Activation

Peripheral Blood Mononuclear Cells (PBMCs) from healthy individuals (New York Blood Center, New York, N.Y.) were prepared using Ficoll-paque plus (GE Amersham, Uppsala, Sweden). Whole blood samples from rheumatoid arthritis patients were purchased from Bioreclamation (New York, N.Y.) and were processed similar to healthy donor blood. All healthy donor and patient samples were consented prior to purchase, were none-identifiable and approved by institutional human subjects board. $CD4^+$ T cells were isolated using Dynal CD4 Positive Isolation Kit (Invitrogen, Carlsbad, Calif.) directly from purified PBMCs and were >99% pure. $CD4^+$ T cells were sorted by FACS ARIA cell sorter (BD, San Jose, Calif.) into $CD45RO^+$ $CD25^-$ memory T ($T_M$) cells. $T_M$ cells were activated either by anti-CD3 and anti-CD28 (aCD3/aCD28) coated beads (1:4 beads:cells ratio) for 18-24 hours, or by Phorbol 12-myristate 13-acetate (PMA) and ionomycin for 4 hours and further FACS sorted based on CCR6 and IL-17 expression into $CCR6^-$ $IL-17^-$, $CCR6^+IL-17^+$, or $CCR6^+IL-17^-$ subsets (as determined by secretion assay labeling, see below). Sorted cells (>99% pure) were cultured in serum-free Xvivo-15 medium (Lonza, Wakersville, Md.) at 37° C. and 5% $CO_2$ for 6-7 days prior to restimulation with PMA and ionomycin (see below). Culture conditions included: 10 U/mL recombinant human IL-2, (BD Biosciences, San Jose, Calif.), 20 ng/mL IL-7, 20 ng/mL IL-15, or 20 ng/mL IL-23 (all from R&D Systems, Minneapolis, Minn.). To determine the fold expansion, $CCR6^+IL-17^+$ or $CCR6^-$ $IL-17^-$ subsets were labeled with CFSE (Molecular Probes, Eugene, Oreg.) or eFluor 670 (eBioscience, San Diego, Calif.), respectively, as previously described (Oswald-Richter, et al., *PLoS Biol* 2004; 2: E198). Alternatively, $CCR6^+$ or $CCR6^-$ $T_M$ cells directly sorted from $CD4^+$ T cells were either maintained in IL-7 or activated with aCD3/aCD28 coated beads and cultured in IL-2 containing RPMI 1640 medium with 10% fetal calf serum (FCS) (Oswald-Richter, et al., *PLoS Pathogens* 2007; 3: e58). In the experiments using PI-3K signaling inhibitors, cells were treated with PI-3K specific inhibitor, LY294002 (EMD, Gibbstown, N.J.), or Akt specific inhibitor, AKTi-1/2 (EMD), for 2 days before PMA and Ionomycin restimulation.

Mouse T Cell Isolation and Culture

Wild-type C57B6/J mice were purchased from Jackson Laboratories (Bar Harbor, Me.) and all mice were used in accordance with a protocol approved by the animal care and use committee of Sirtris pharmaceuticals. Single cell suspensions were prepared from spleens and peripheral lymph nodes following red blood cell lysis (Sigma-Aldrich, USA). CD4+ T cells were enriched by magnetic cell sorting using the mouse CD4+ T cell isolation kit II (Miltenyi Biotec, Auburn, Calif.) in accordance with manufacturers instructions, and these cells were stimulated for 18-24 hours using plate-bound anti-CD3 (eBioscience) and anti-CD28 (BD Biosciences) antibodies as previously described (Sundrud, et al., *Science* (New York, N.Y.) 2009 324: 1334-1338). Activated T cells were then stained for cell surface receptors and subjected to mouse IL-17 capture assay for FACS sorting into CD62L$^{lo}$CCR6$^-$IL-17$^-$, CD62L$^{lo}$CCR6$^+$IL-17$^-$, or CD62L$^{lo}$CCR6$^+$IL-17$^+$ subsets (see below). Sorted mouse T cell populations were cultured in DMEM medium (Mediatech, Inc., USA) containing 10% FCS (Invitrogen). To expand sorted T cell populations, 10 U/mL recombinant human IL-2 (BD Biosciences) and mouse CD3/CD28 T cell expander beads (1:2 beads:cells ratio) (Invitrogen) were added and cells were cultured for 6 days prior to restimulation.

IL-17 Secretion Assay

Manufacturer's protocols (Miltenyi Biotec) for labeling human and mouse IL-17 secreting cells were followed. Briefly, activated T-cells were washed in cold buffer (PBS+ 0.5% BSA+2 mM EDTA) and labeled with IL-17 catch reagent for 5 minutes on ice. Pre-warmed medium was then added and the cells were incubated at 37° C. on a shaker for 45 minutes. For human IL-17 capture experiments, cells were washed once more with cold buffer and PE-conjugated IL-17 detection antibodies were added and incubated on ice for 10 minutes. For mouse IL-17 capture experiments, all steps were identical, except that the IL-17 detection antibody used was biotinylated, and a secondary staining step using APC-conjugated streptavidin was used. Cells were then washed and stained with additional cell surface antibodies at room temperature for 20 minutes. These cells were then washed once more with cold buffer, resuspended in serum-free RPMI 1640 medium, filtered and FACS sorted. Antibodies used for human IL-17 secretion sorts were: CCR6-PercpCy5.5 (CloneTG7/CCR6, Biolegend, San Diego, Calif.), CD25-Alexa 700 (Clone BC96, Biolegend). Antibodies for mouse IL-17 secretion sorts were: CD4-Pacific Orange (Invitrogen), CD62L-Pacific Blue (eBioscience), CCR6-PE (Biolegend), IL-17A-biotin (Miltenyi Biotec), and streptavidin-APC (eBioscience).

Plasmids and Gene Cloning

Full-length human KLF2 cDNA (NM_016270) (pCMV6-XL4-KLF2) was purchased from Origene (Rockville, Md.) and cloned into a lentiviral vector at EcoRI sites. This vector consists of Human immunodeficiency virus-Derived Vector (HDV), an internal ribosome entry site (IRES) and a gene for RFP. The primers for KLF2 amplification were:

```
                                         (SEQ ID NO: 1)
5'F: CCGGAATTCGCCATGGCGCTGAGTGAACCCATC, (SEQ ID NO: 2)
3'R: CCGGAATTCCTACATGTGCCGTTTCATGTGCAG.
```

Wild type FOXO1 (FOXO1-GFP) was a gift from Dr. Terry G Unterman (University of Illinois, Chicago). FOXO1-GFP fusion protein was engineered into HDV in frame with XbaI and XhoI sites. The primers for FOXO1 amplification were:

```
                                         (SEQ ID NO: 3)
5'F: GCTCTAGAGCATTGCCATGGCCGAGGCGCCT, (SEQ ID NO: 4)
3'R: TT CTCGA G GC TTA CTT GTA CAG CTC GTC.
```

The lentivirus encoding RORC gene: RORC-IRES-HSA was a gift from Dr. Dan Littman (New York University School Of Medicine, Skirball Center, N.Y.). Short hairpin RNA against KLF2 (shKLF2) (Invitrogen) was engineered into a lentiviral vector as previously described (Antons, et al., *J Immunol* 2008; 180: 764-773) targeting position 922 in the cDNA: GGCAAGACCTACACCAAGAGT (SEQ ID NO:5).

Lentiviruses Production and Transductions

The lentiviruses pseudotyped with VSV-G envelope were generated as previously described (Unutmaz, et al., *J Exp Med* 1999; 189: 1735-1746). All lentiviruses expressed green fluorescent protein (GFP), red fluorescent protein (RFP) or heat stable antigen (HSA) as the marker in place of the nef gene, as previously described (Oswald-Richter, et al., *PLoS Pathogens* 2007; 3: e58; Oswald-Richter, et al., *PLoS Biol* 2004; 2: E198; Unutmaz, et al., *J Exp Med* 1999; 189: 1735-1746). Viral titers were measured as described (Oswald-Richter, et al., *PLoS Pathogens* 2007; 3: e58; Unutmaz, et al., *J Exp Med* 1999; 189: 1735-1746) and ranged from 1-30×10$^6$ IFU/ml. Activated T$_M$ cells were transduced with different genes, such as FOXO1, KLF2 and RORC, or KLF2 shRNA and maintained in IL-2 containing 10% FCS RPMI 1640 medium for 14 days before reactivation with PMA and Ionomycin.

Staining and FACS Analysis

Cells were stained as previously described (Oswald-Richter, et al., *PLoS Pathogens* 2007; 3: e58). For intracellular staining, T cell cultures were stimulated for 5 hours at 37° C. with PMA and Ionomycin and Golgistop (BD Biosciences). Stimulated cells were washed with PBS and stained with Fixable Viability Dye eFluor450 (eBioscience) to gate on live cells. Cells were then fixed and permeabilized by commercially available Foxp3 intracellular staining kit (eBioscience) or cytofix/cytoperm kit (BD Biosciences) as per manufacturer's protocol. Antibodies used for surface and intracellular staining included: CD45RO-FITC; CD25-PE; IFN-γ-FITC (clone 4S. B3), PE Cy7 or A700; IL-4-APC or PE; IL-17A (IL-17)-Pacific Blue (Clone BL168), FITC or Percp Cy5.5; IL-10-APC (Biolegend); IL-22-PE (R&D) or APC (eBioscience); IL-21-PE (clone 22URT1, eBioscience); FOXO1 rabbit monoclonal antibody; phospho-AKT (Ser473)-Alexa Fluor 488; Rabbit IgG isotype control-Alexa Fluor 488 (Cell Signaling, Danvers, Mass.); and CCR6-biotin (BD Biosciences). Secondary antibodies used were: Streptavidin-APC or PercpCy5.5 (BD Biosciences), Goat anti mouse-APC (BD Biosciences), anti rabbit-Alexa 647 (Molecular Probes). All data were acquired on LSRII instrument (BD Biosciences) using FACSDiva software. Data analyses were done using Flowjo software (Treestar Inc, Ashland, Oreg.). For phospho-Akt staining, Jurkat cells were fixed with BD Cytofix buffer (BD Biosciences) pre-warmed to 37° C. for 10 minutes. After spinning down, the cells were permeablilzed with ice-cold BD Phosflow Perm buffer III (BD Biosciences) on ice for 30 minutes and were stained with phospho-antibody.

RNA Isolation and Quantitative PCR

Purified T cells ($1\times10^5$) were snap frozen in liquid nitrogen for total RNA isolation. Total RNA was isolated using RNeasy isolation kit (Qiagen, Valencia, Calif.) according to the manufacturer's protocol. The extracted RNA was then reverse transcribed into cDNA and quantified using Taqman Cell to CT kit (Applied Biosystems, Carlsbad, Calif.). Taqman primers and probe sets were purchased from Applied Biosystems: Human KLF2 (Hs00360439_g1), RORC (Hs01076120_g1), Il-17a (Hs00174383_m1), b-Actin (Hs03023880_g1), Foxp3 (Hs00203958_m1). Data was acquired and analyzed on ABI 7500 sequence detection system. Quantitative real-time PCR data was analyzed by normalizing Ct values of genes of interest to the Ct values of the housekeeping gene b-Actin.

Western Blot Analysis

KLF2 transient transfected HEK293T cells were lysed in RIPA buffer (Sigma) and mixed with 2× Laemmli sample loading buffer (BioRad), boiled, and separated on 10.0% polyacrylamide gels containing SDS (Pierce, Rockford, Ill.). Following electrophoresis, proteins were transferred to a PVDF membrane by electroblotting and incubated for 1 hour at room temperature in blocking buffer (5% nonfat dry milk in PBS). The blocked blot was exposed to the primary antibody rabbit anti-KLF2 (Invitrogen) 1:500 or anti-tubulin (Sigma-Aldrich) in blocking buffer with constant mixing. After extensive washing, bound antibodies were detected by chemiluminescence using horseradish peroxidase-conjugated species-specific secondary antibodies as described by the manufacturer (GE Healthcare).

Statistical Analysis

Data were analyzed using Graphpad prism software (Graphpad Inc., La Jolla, Calif.) using student's t-test for statistical analysis. $p<0.05$ is considered significant.

Online Supplemental Material.

FIG. 7 shows the induction of IL-17 from CCR6$^+$IL-17$^-$ memory T cells stimulated with PMA/Ionomycin. FIG. 8 demonstrates that murine CCR6$^+$IL-17$^-$ $T_M$ cells cultured ex vivo with γc-cytokines are able to express IL-17, similar to human CCR6$^+$IL-17$^-$ $T_M$ cells described in FIG. 1. FIG. 9 demonstrates that CCR6$^+$ $T_M$ cells activated through TCR and cultured in IL-2, express reduced level of IL-17 and IL-22 upon blockage of PI-3K/Akt signals. FIG. 10 presents more cytokine profiles upon PI-3K/Akt inhibitors treatment. FIG. 11 confirms the overexpression and the knockdown of FOXO1 and KLF2. FIG. 12 proposes a potential model how γc-cytokine-signals modulate IL-17 and IL-22 production from CCR6$^+$ $T_M$ cells.

Results.

Figure 7A:
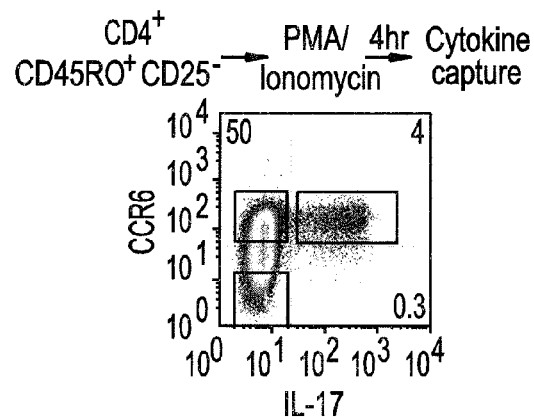
FIG. 7 shows that IL-17 is induced from CCR6$^+$IL-17$^-$ subsets by γc-cytokine ex vivo, while both CCR6$^+$IL-17$^+$ and CCR6$^+$IL-17$^-$ T cells proliferate similarly in response to IL-2 stimulation. (a) Total CD4$^+$ T$_M$ cells (CD45RO$^+$ CD25$^-$) were stimulated for 4 h with PMA and ionomycin and sorted into CCR6$^-$IL17$^-$, CCR6$^+$IL-17$^-$, or CCR6$^+$IL-17$^+$ populations using cytokine capture. (b) Il-17a and Rorc gene expression was analyzed via Taqman qPCR in cells as sorted in (a).
Figure 7B:
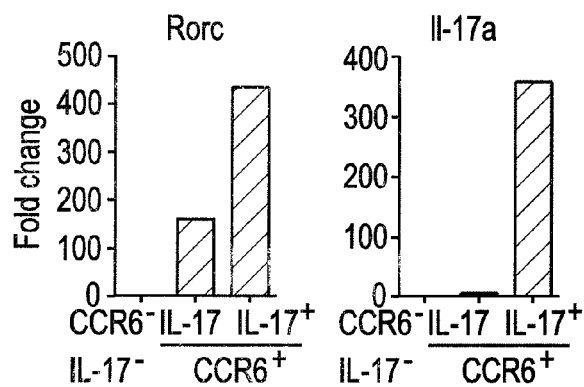
Figure 7C:
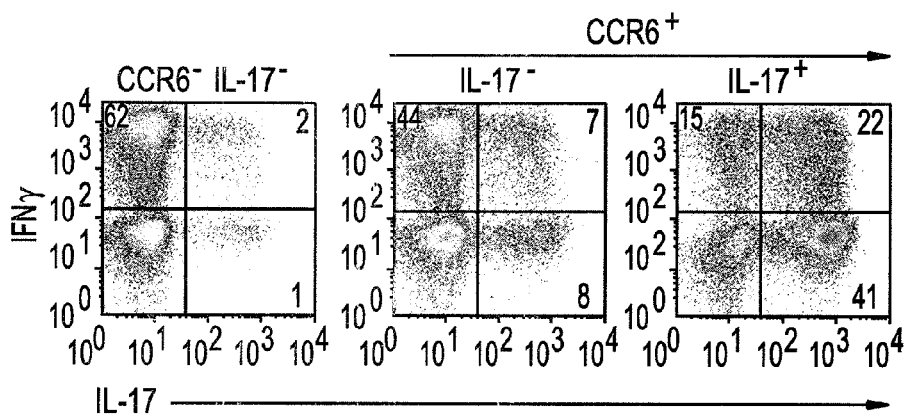
Figure 7D:
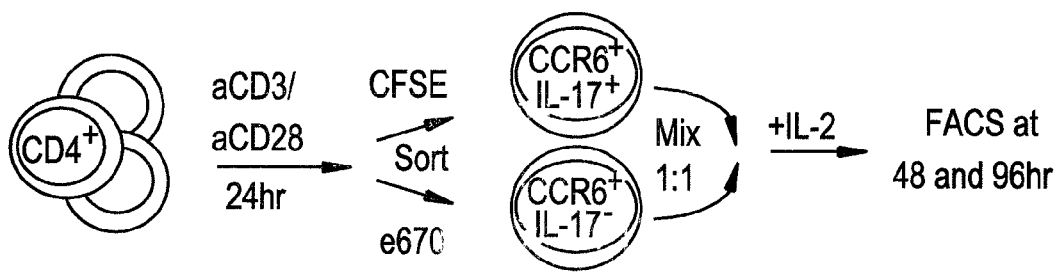
Figure 7E:
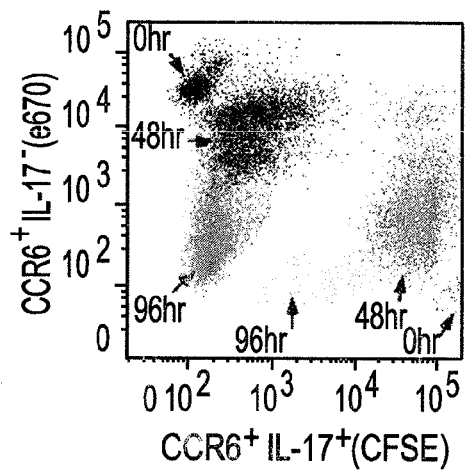
Figure 7F:
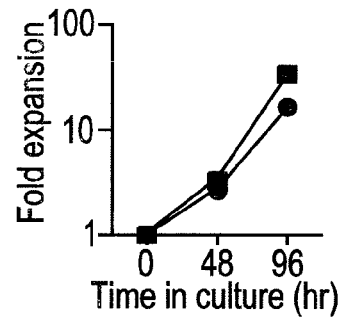
Figure 7G:
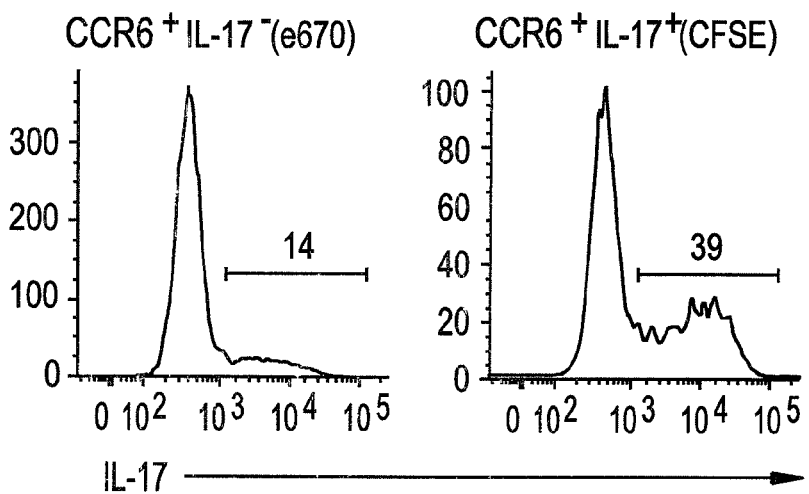

De Novo Induction of IL-17 in CCR6$^+$ IL-17$^-$ T Cells is Driven by γc-Cytokines Nearly all T cells defined as Th17, by virtue of IL-17 expression, also express CCR6, though only a fraction of CCR6$^+$ T cells (~5-10%) actively express IL-17 upon ex vivo stimulation. Given that both CCR6 and IL-17 are upregulated by ectopic expression of RORC in human T cells (Manel, et al., *Nature Immunology* 2008; 9: 641-649) and that CCR6 is a direct target gene of the key Th17 transcription factor Stat3 (Durant, et al., *Immunity* 2010; 32: 605-615), expression of this chemokine receptor may broadly define human T cells that have the capacity to express IL-17, even if they lack IL-17 expression ex vivo. Primary human CD4$^+$ CD45RO$^+$ CD25$^-$ $T_M$ cells stimulated either with beads conjugated to anti-CD3 and anti-CD28 (aCD3/aCD28) antibodies or with PMA and ionomycin into CCR6$^-$IL-17$^-$, CCR6 IL-17$^+$ or CCR6 IL-17$^-$ subsets using a cytokine capture assay (FIG. 1a, 7a) were FACS sorted. Analyses of gene expression directly post-sorting confirmed that Il-17a transcript levels were substantially higher in CCR6$^+$IL-17$^+$ cells compared with either CCR6$^-$ or CCR6 IL-17$^-$ cells, irrespective of the activating stimuli (i.e., aCD3/aCD28 or PMA and ionomycin). However, both CCR6$^+$ T cell subsets displayed elevated RORC expression levels that ranged between 80- to 400-fold higher than those observed in CCR6$^-$ $T_M$ cells (FIG. 1b, 7b) (Singh, et al., *J Immunol* 2008; 180: 214-221). Given that RORC was highly expressed in CCR6$^+$ $T_M$ cells independent of ex vivo IL-17 production, these T cell subsets were cultured in IL-2-supplemented medium for 6 days to ask whether CCR6$^+$ IL-17$^-$ cells could upregulate IL-17 expression. As expected, a large majority of cells initially sorted as CCR6$^+$IL-17$^+$ maintained high-level IL-17 expression upon restimulation, whereas CCR6$^-$IL-17$^-$ cells remained largely IL-17 negative (FIG. 1c, 7c). Remarkably, 20-40% of the CCR6$^+$ cells initially sorted as IL-17$^-$ expressed IL-17 after culture with IL-2 (FIG. 1c, 7c).

Given that IL-2 is the prototype of the IL-2 family of cytokines, all of which signal through cytokine receptors comprised in part by the γc subunit, whether other γc-cytokines could also induce de novo IL-17 production by CCR6$^+$ IL-17$^-$ $T_M$ cells was investigated. Both IL-7 and IL-15 induced similar levels of IL-17 expression in CCR6$^+$ IL-17$^-$ T cells, whereas IL-23, which is known to enhance Th17 cell differentiation (Ivanov, et al., *Semin Immunol* 2007; 19: 409-417), did not influence IL-17 expression in the absence of IL-2 (FIG. 1e). In contrast, and as observed for IL-2, neither IL-7 nor IL-15 induced IL-17 expression in CCR6$^-$ $T_M$ cells. In addition, CCR6$^+$, but not CCR6$^-$, IL-17$^-$ memory T cells isolated from peripheral lymphoid organs of wild-type C57B/6 mice were capable of producing IL-17 after 6 days in culture with IL-2 (FIG. 8).

These findings indicate that ex vivo analyses of IL-17 expression underestimate the frequency of memory T cells that can express IL-17 in inflammatory settings. Because a number of studies have investigated changes in Th17 frequencies within autoimmune patient cohorts, whether CCR6$^+$ IL-17$^-$ $T_M$ cells isolated from the peripheral blood of patients with rheumatoid arthritis (RA) could be similarly induced to express IL-17 by IL-2 stimulation was investigated. Indeed, CCR6$^+$, but not CCR6$^-$, IL-17$^-$ memory T cells from RA patients upregulated IL-17 after culture with IL-2 to similar levels observed in healthy adult donors (FIG. 10. Collectively, these data demonstrate that CCR6$^+$ memory T cells are uniquely poised to express IL-17 in response to IL-2 stimulation irrespective of their IL-17 phenotype ex vivo. These results also indicate that this inflammatory feature of CCR6$^+$ $T_M$ cells is conserved between humans and mice.

Figure 3A:
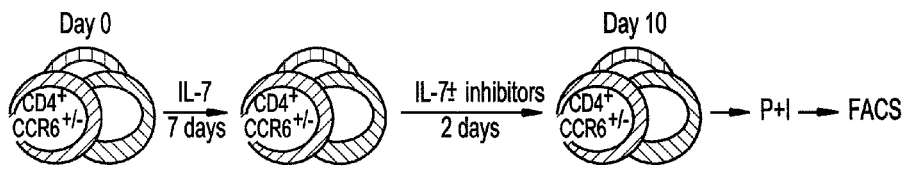
FIG. 3 shows that PI-3K/Akt inhibitors suppress IL-17 and IL-22 production from IL-7-stimulated CCR6$^+$ memory T cells. (a) Resting CD4$^+$CD45RO$^+$ CD25$^-$CCR6$^{+/-}$ T cells were cultured in IL-7-containing medium for 7 days followed by culture with or without PI-3K signaling inhibitors for an extra 2 days. Cells were then stimulated with PMA and ionomycin and subjected to intracellular staining and FACS analysis as described in methods. (b) Blockade of PI-3K signaling suppresses IL-17 and IL-22 production induced by IL-7 from CCR6$^+$ T$_M$ cells. Intracellular cytokine staining was performed on CCR6$^+$ and CCR6$^-$ T$_M$ cells ex vivo (Day 0) and following different culturing conditions (Day 10) as described in (a). CCR6$^{+/-}$ T$_M$ cells were cultured with IL-7 alone or plus LY294002 (5 μg/ml) or AKTi-1/2 (5 μg/ml). (c) Frequency of IL-17-producing T cells is increased by γc-cytokine stimulation across different donors. CCR6$^+$ T$_M$ cells isolated from 7 healthy donors (D) were stimulated either ex vivo or at day 10 post culture with IL-7. (d, e) PI-3K and Akt inhibitors inhibit IL-17, IL-22 and IL-4 expression in IL-7-activated CCR6$^+$ T$_M$ cells in a dose-dependent manner. Cells cultured in IL-7 with or without LY294002 or AKTi-1/2 at different concentrations (μg/ml) were collected and analyzed. The frequency of single (d) or double (e) cytokine-producing cells without inhibitors treatment (control, 0) was normalized to 100%. Cytokine percentage (%) of control was calculated accordingly. Data are presented as the mean percentage cytokine±SD from at least three different donors. The statistical analyses, either ex vivo, or at day 10 with PI-3K inhibitor treatments, are relative to day 10 IL-7 only (filled blue rectangle). Data from CCR6$^-$ is representative out of three donors. * p<0.05,  p<0.005. * p<0.001. NS: no significance.
Figure 3B:
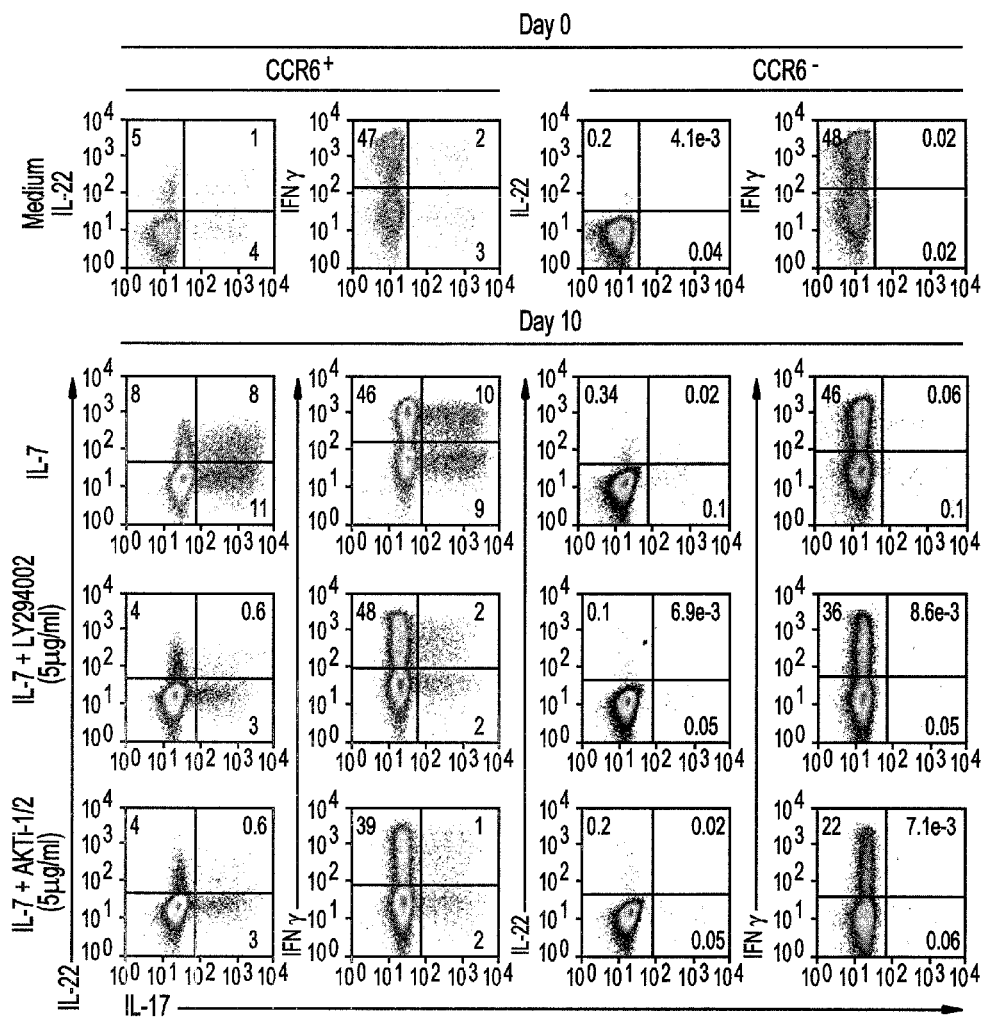
Figure 3C:
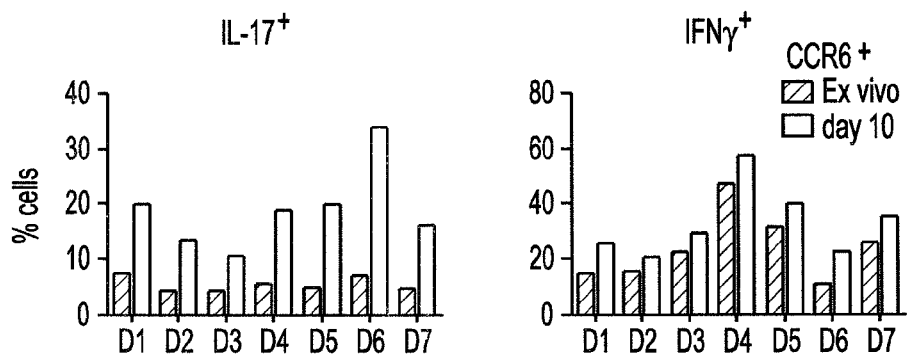

PI-3K/Akt Signaling Mediates Th17 Cytokine Induction by γc-Cytokines

γc-cytokines such as IL-7 can promote T cell survival in the absence of TCR signaling, and do so without inducing significant cell division (Unutmaz, et al., *J Exp Med* 1999; 189: 1735-1746; Unutmaz, et al., *J Exp Med* 1994; 180: 1159-1164). Given that IL-7 and IL-15 could substitute for IL-2 in inducing Th17 cytokine expression in TCR-activated CCR6$^+$ $T_M$ cells, whether γc-cytokine signaling was sufficient to promote IL-17/IL-22 expression in resting human CCR6$^+$ $T_M$ cells not stimulated through the TCR was investigated (FIG. 3a). Indeed, stimulation of resting CCR6$^+$CD45RO$^+$CD25$^-$ $T_M$ cells with IL-7 for 10 days consistently enhanced the expression of both IL-17 and IL-22 more than 3-fold compared to the same cells isolated ex vivo (day 0) (FIG. 3b, 3c). Importantly, IL-7-mediated induction of IL-17 and IL-22 expression was restricted to CCR6$^+$ cells, as CCR6$^-$ T$_M$ cells stimulated with IL-7 failed to express IL-17 or IL-22 (FIG. 3b). Moreover, culture of resting CCR6$^+$ or CCR6$^-$ T$_M$ cells with IL-7 had almost no impact on IFNγ production (FIG. 3b, 3c). Stimulation of resting CCR6$^+$ T$_M$ cells with IL-15 led to similar increases in IL-17/IL-22 expression (unpublished data), whereas another γc-cytokine, IL-4, did not promote Th17 cytokine production in resting CCR6$^+$ T$_M$ cells or confer T$_M$ cell survival (FIG. 9b, unpublished data). Interestingly, IL-23 did not significantly synergize with IL-7 to further induce IL-17 or IL-22 expression (FIG. 9b).

Human CCR6$^+$ T cells can express IL-17 alone, or in combination with other pro-inflammatory cytokines such as IL-22 or IFNγ. Cells co-expressing IFNγ and IL-17 have been shown to share functional characteristics with those expressing IL-17 alone (Boniface, et al., *J Immunol* 2010; 185: 679-687), whereas the function of IL-17$^+$IL-22$^+$ cells is unclear. IL-7 stimulation had even more profound effects on the proportion of cells that co-expressed either IL-22 or IFNγ with IL-17; these double cytokine-producing cells increased more than 5-fold in response to IL-7 signaling (FIG. 3b). Together, these results demonstrate that γc-cytokines, particularly IL-2, IL-7 and IL-15 potently enhance IL-17/IL-22 secretion by CCR6$^+$ T$_M$ cell subsets.

Figure 3D:
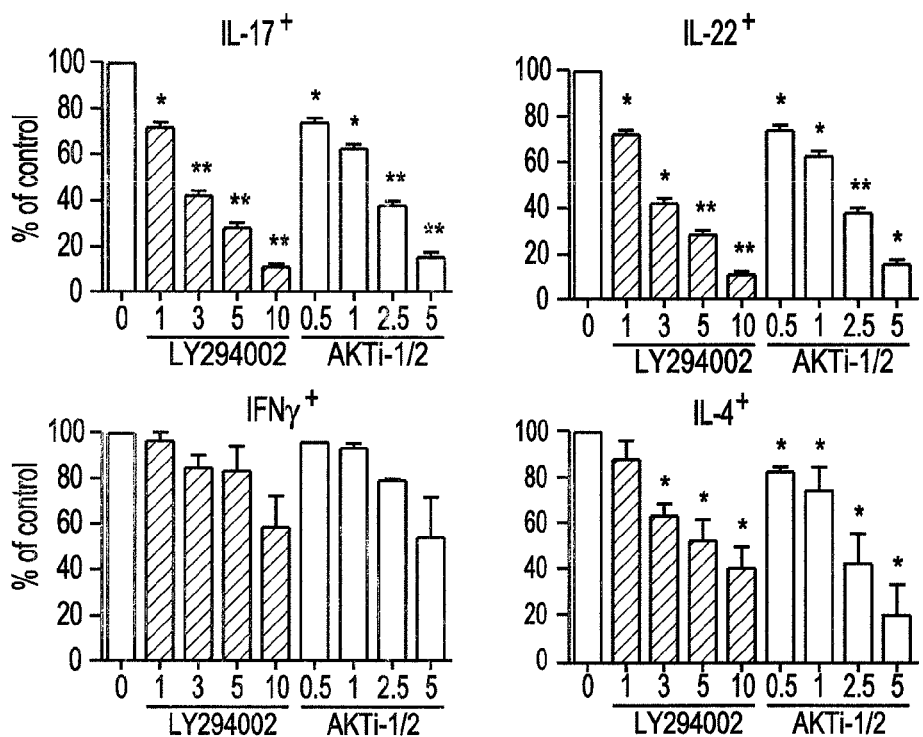
Figure 3E:
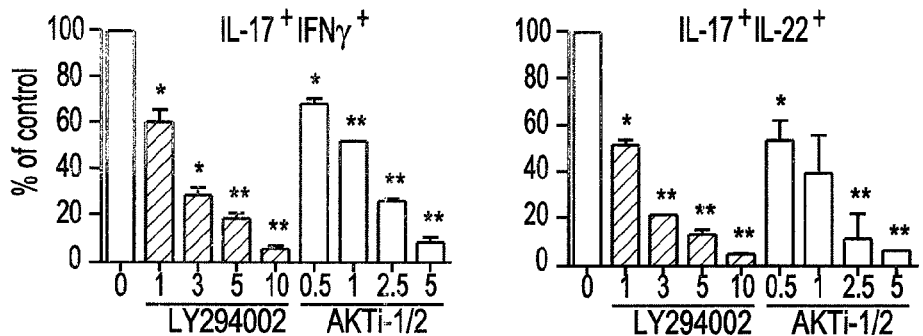

Signaling through γC-containing cytokine receptors regulates T cell survival and homeostasis through activation of the PI-3K/Akt pathway (Rochman, et al., *Nature Reviews* 2009; 9: 480-490). In order to determine if this pathway also controls expression of IL-17 and IL-22, we treated CCR6$^+$ T$_M$ cells that had been cultured for one week in IL-7 with or without the PI-3K inhibitor LY294002 or the Akt inhibitor AKTi-1/2 for additional 48 hours (FIG. 3a). Treatment of T$_M$ cells with 1-10 µg/mL of either inhibitor downregulated cytokine-dependent phosphorylation of Akt without adversely affecting cell viability (FIG. 9a). Control- or compound-treated T cells were then restimulated to analyze their impact on cytokine production. Treatment with either LY294002 or AKTi-1/2 repressed γc-mediated IL-17/IL-22 induction in a dose-dependent manner, whereas expression of IL-4 or IFNγ was either less reduced or not affected, respectively (FIG. 3d, 3e). Inhibitory effects of the PI-3K and Akt inhibitors were even more profound when considering the proportion of T cells co-expressing IL-22 or IFNγ together with IL-17 (FIG. 3e). Furthermore, treatment with PI-3K or Akt inhibitors also repressed IL-17 and IL-22 expression in TCR-activated CCR6$^+$ T$_M$ cells cultured in IL-2 (FIG. 9c-9e). These effects were reversible since IL-17/IL-22 levels were restored upon removal of PI-3K or Akt inhibitors from culture medium (unpublished data). Moreover, IL-17/IL-22 repression by PI-3K or Akt inhibition was not associated with changes in Rorc or Foxp3 expression levels (FIG. 9f).

Figure 3F:
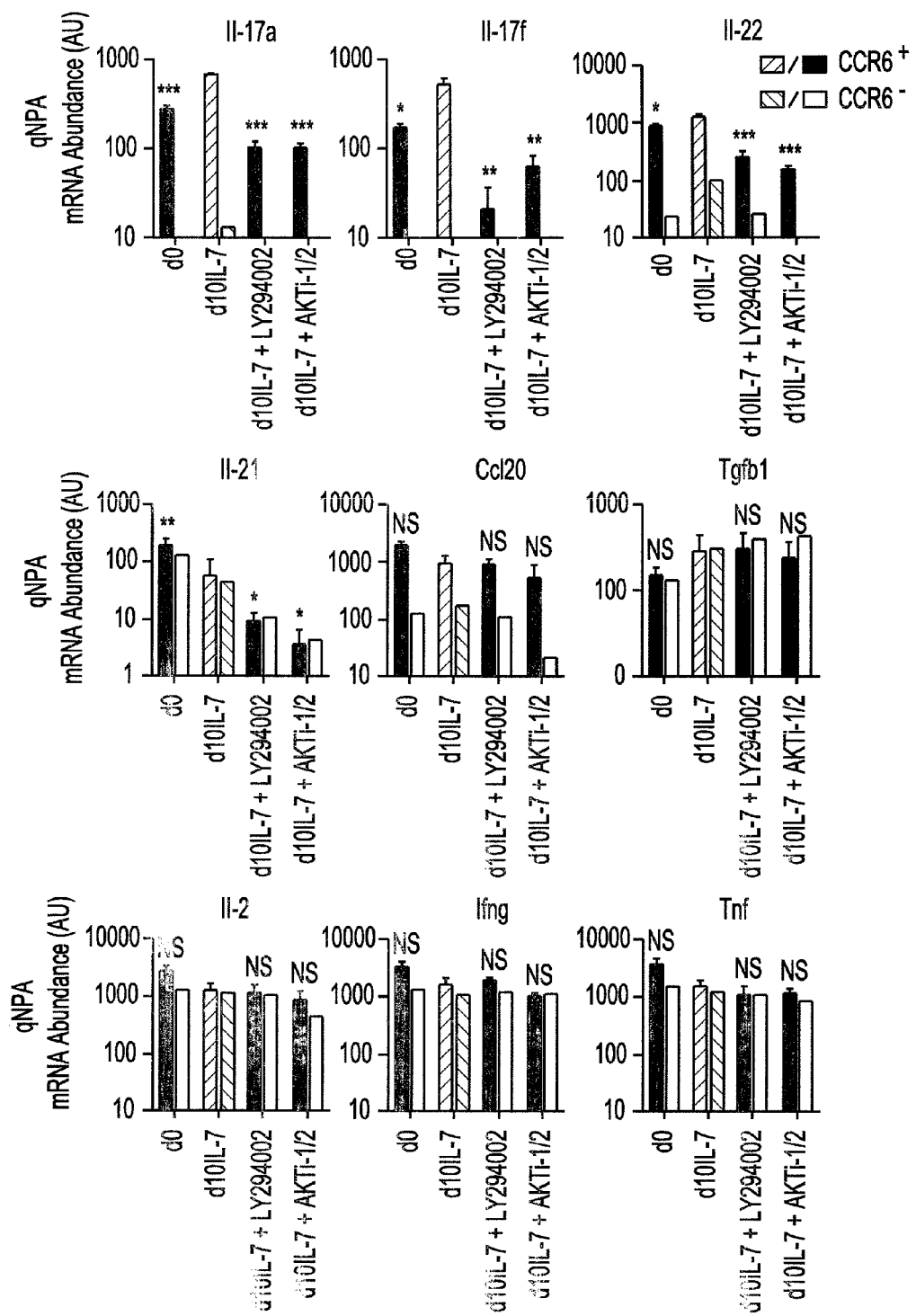
Figure 10A:
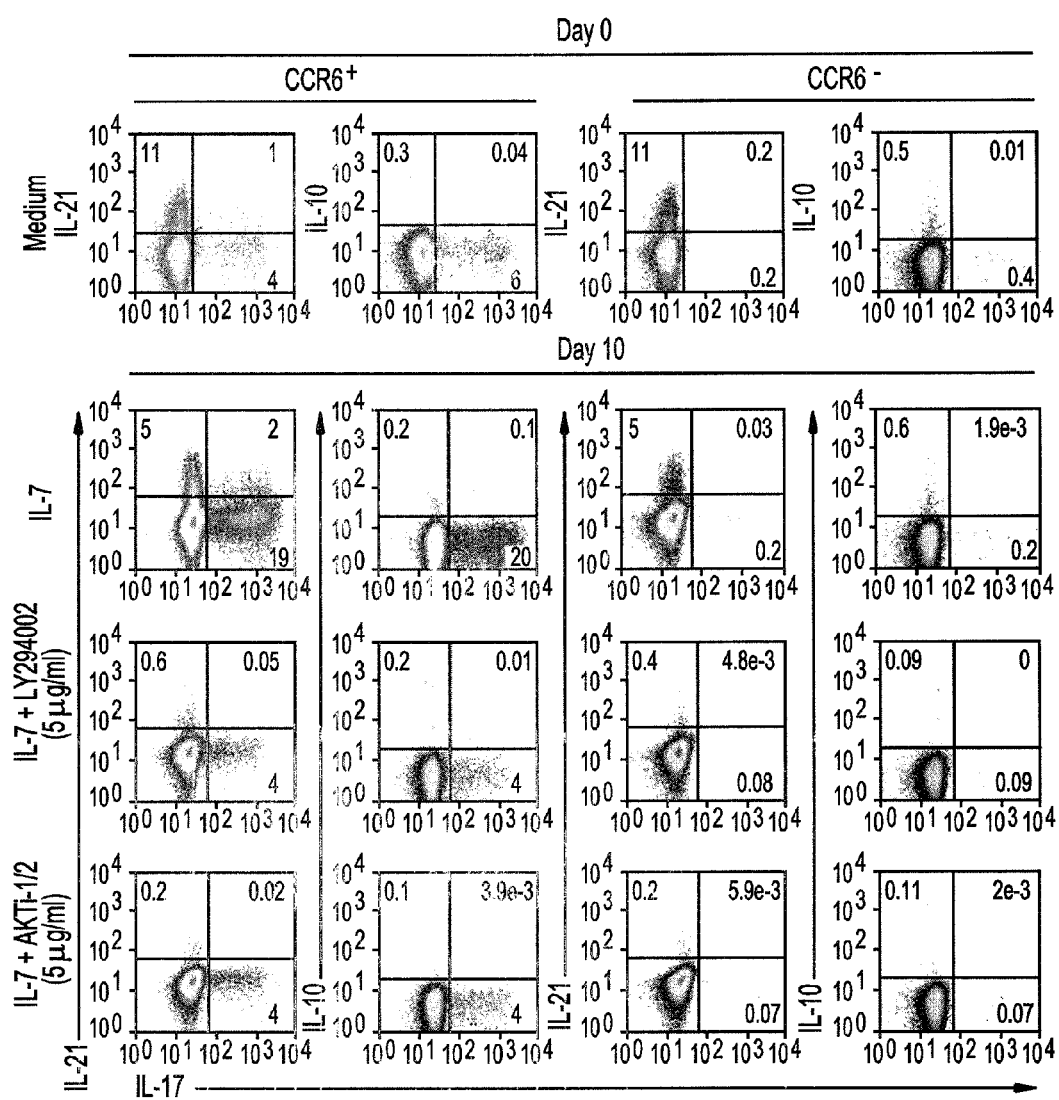
Figure 10B:
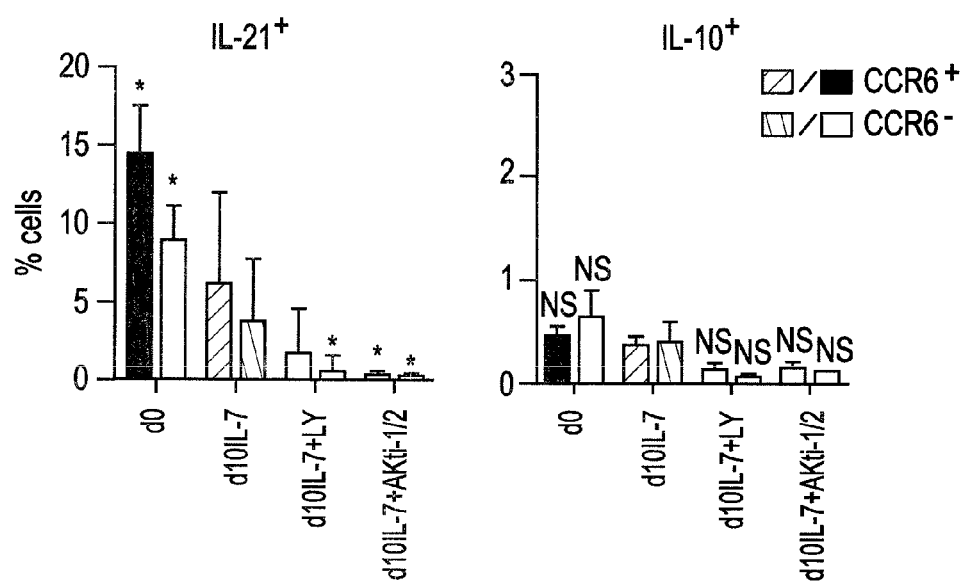
Figure 10C:
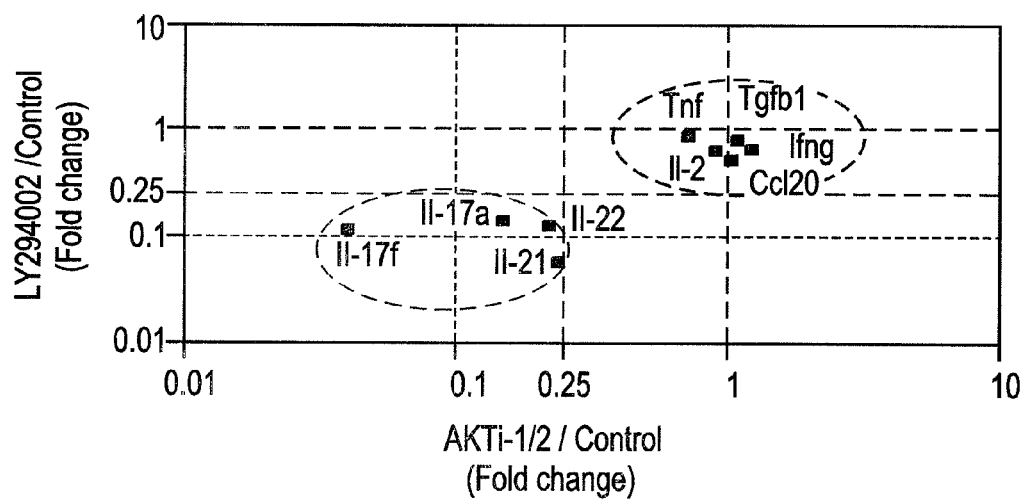

The impact of PI-3K or Akt inhibition on the expression of a broader panel of both Th17-related and unrelated cytokines was evaluated in order to determine how selectively this pathway regulates inflammatory cytokine expression. In addition to IL-17A, IL-17F, and IL-22, Th17 cells have been shown to preferentially express IL-21 (Nurieva, et al., *Nature* 2007; 448: 480-483), IL-26 (in human cells), CCL20 (Wilson, et al., *Nature Immunology* 2007; 8: 950-957), and in some instances IL-10 (Zhu, et al., *Cell Res* 2010 20: 4-12). Although intracellular IL-10 production was not detectable in either CCR6$^+$ or CCR6$^-$ T$_M$ cells upon stimulation ex vivo or after culture with IL-7, we found that, unlike IL-17 and IL-22, ex vivo production of IL-21 was equivalent in both human CCR6$^-$ and CCR6$^+$ T$_M$ cell subsets (FIG. 10a, 10b). Similarly, and in contrast to IL-17 and IL-22, expression of IL-21 was not increased in either CCR6$^+$ or CCR6$^-$ T$_M$ cells upon stimulation with IL-7, and in fact was slightly reduced (FIG. 3f, 10a-10b). IL-21 expression was, however, sensitive to treatment with PI-3K or Akt inhibitors (FIG. 10a-10b). Ccl20 was preferentially expressed ex vivo by CCR6$^+$ T$_M$ cells (FIG. 1d) and was neither significantly induced by IL-7 stimulation, nor repressed by PI-3K pathway inhibition (FIG. 3f, 10c). The expression of other non-Th17 related cytokines, such as Il2, Ifng, Tnf, and Tcl were not influenced by IL-7 stimulation or by treatment with PI-3K or Akt inhibitors (FIG. 3f, 10c). Thus, PI-3K signaling downstream of γc-cytokine receptors promotes the expression of Th17-signature cytokines (Il-17a, Il-17f, Il-22) within CCR6$^+$ memory T cells, and does so with a high degree of specificity over other unrelated cytokines FOXO1 and KLF2 Repress IL-17/IL-22 Expression.

Figure 4A:
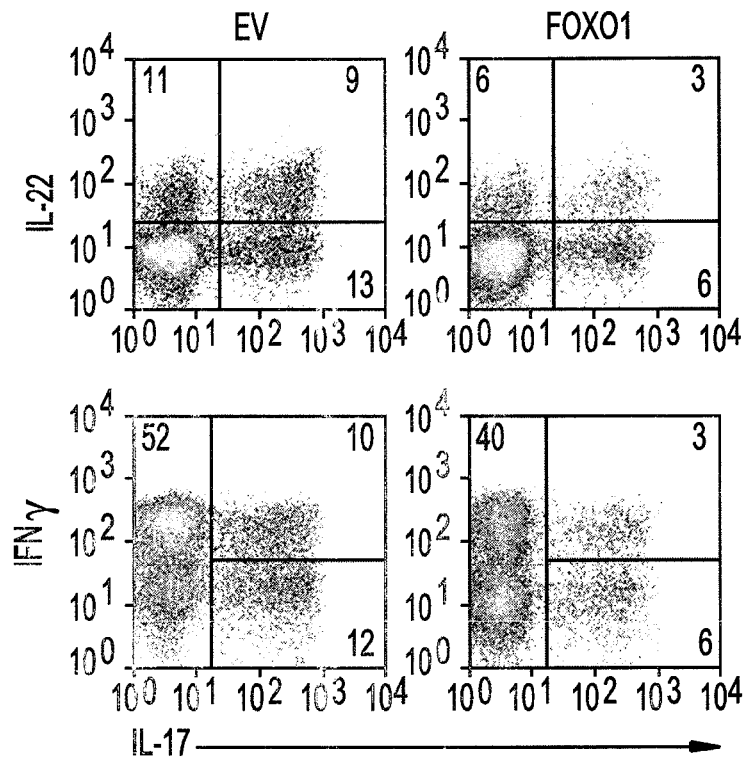
FIG. 4 demonstrates that IL-17/IL-22 production from CCR6$^+$ memory T cells is suppressed by ectopic FOXO1 expression. (a) T cells activated through their TCR were transduced with FOXO1-GFP and cultured in IL-2 for 14 days then stimulated with PMA and ionomycin, stained for intracellular cytokines and subjected to FACS analysis. (b) The frequency of single or double cytokine-producing cells from FOXO1 or EV-transduced cells is shown. Data are presented as mean frequency of cytokine producing cells±SD from four independent individuals. * p<0.05. NS: no significance.
Figure 4B:
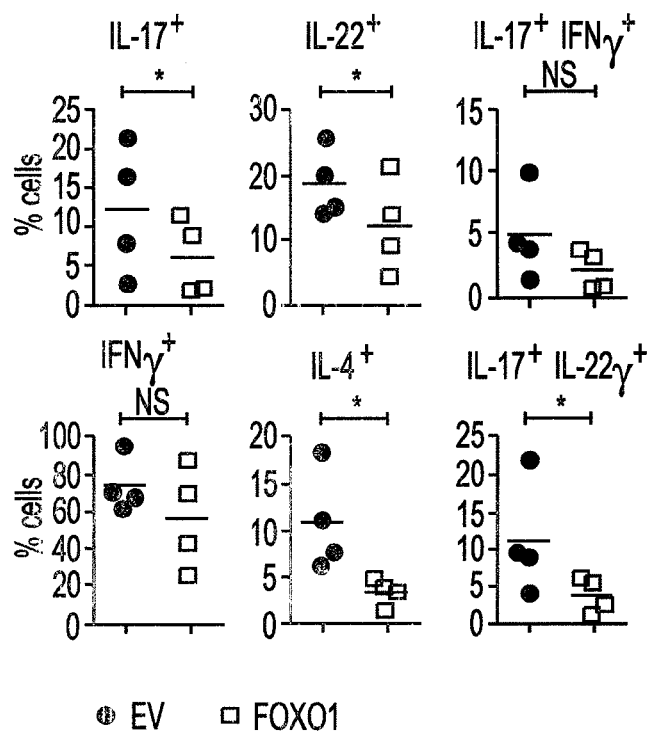

PI-3K activation downstream of γc-cytokine stimulation negatively regulates FOXO1 nuclear localization and transcriptional activity (Birkenkamp, et al., *Biochemical Society Transactions* 2003; 31: 292-297). Because cytokine-driven IL-17 and IL-22 expression by CCR6$^+$ T$_M$ cells is sensitive to PI-3K or Akt inhibition, whether ectopic expression of FOXO1 could also repress γc-mediated IL-17/IL-22 expression was evaluated. Human CCR6$^+$ T$_M$ cells were activated and transduced with control (empty vector, EV) or FOXO1-expressing lentiviruses, and then expanded in the presence of IL-2 and FOXO1 overexpression was confirmed by intracellular staining (FIG. 11a), and these cells were then restimulated to evaluate effects on cytokine production. Analogous to treatment of cells with PI-3K and Akt inhibitors, FOXO1 overexpression reduced both IL-17 and IL-22 secretion (FIG. 4a, 4b).

Figure 5A:
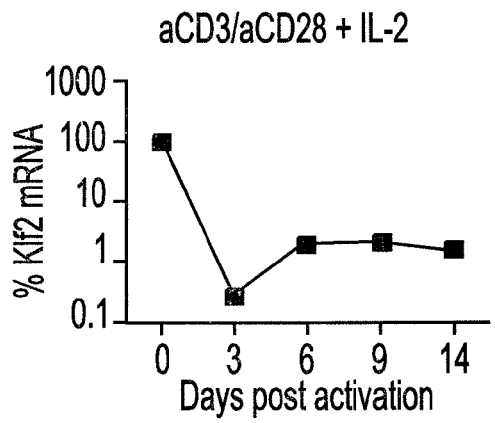
FIG. 5 shows that Klf2 expression is regulated by γc-cytokine-induced PI-3K signaling pathway. (a) Klf2 message is abundant in resting CD4$^+$ T cells and downregulated upon activation through the TCR. Total cellular RNA was extracted from cell pellets of resting, aCD3/aCD28 beads-activated CD4$^+$ T$_M$ cells. The RNA was subjected to RT-qPCR for Klf2 and b-actin mRNA quantification. (b) Blockade of PI-3K signaling by LY294002 treatment upregulates Klf2 transcripts in a dose-dependent manner in CCR6$^+$ T$_M$ cells cultured in IL-7. CCR6$^+$ T$_M$ cells were cultured in IL-7-containing medium as in FIG. 3a. Total RNA from either ex vivo freshly isolated (Day 0) or cultured in IL-7 (Day 10) with or without LY294002 at the indicated concentrations was collected and subjected to RT-qPCR to detect Klf2 levels. (c) Ectopic transduction of KLF2 in TCR-activated, IL-2-cultured T$_M$ cells maintains Klf2 message levels comparable to resting cells. Data shown is from one representative of three different donors.
Figure 5B:
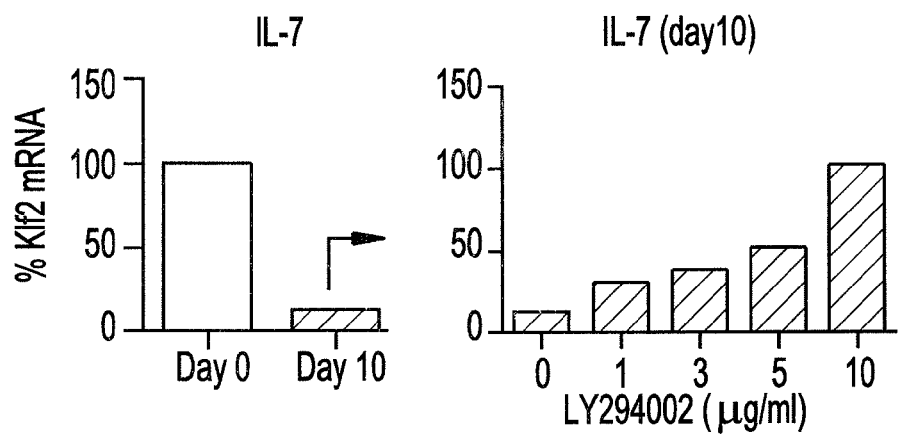
Figure 11A:
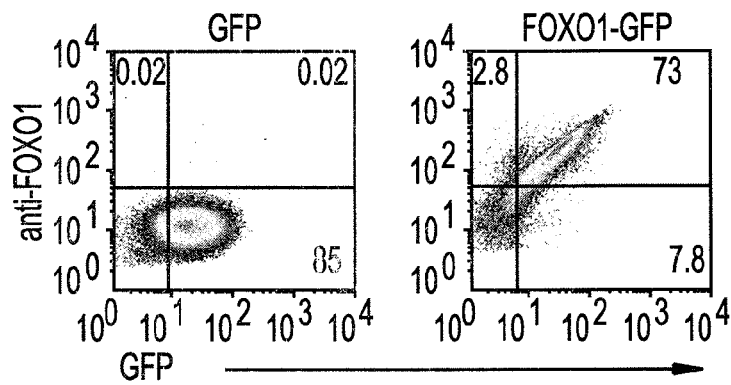
Figure 11B:
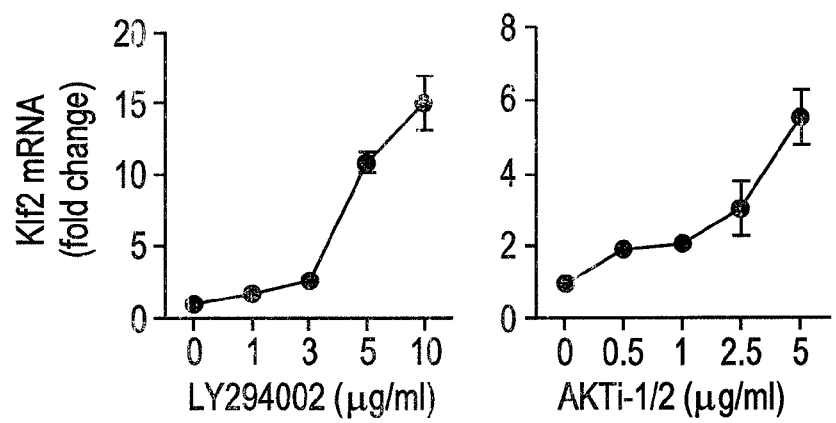

Another transcription factor, KLF2, is also reported to be negatively regulated by PI-3K signaling (Sinclair, et al., *Nature Immunology* 2008; 9: 513-521). In contrast to FOXO1, however, KLF2 is repressed by PI-3K signaling primarily at the level of gene expression (Weinreich, et al., *Immunity* 2009; 31: 122-130). To investigate whether KLF2 may regulate IL-17/IL-22 secretion by CCR6$^+$ T$_M$ cells, the kinetics of Klf2 mRNA expression in T$_M$ cells were analyzed. In line with previous studies (Grayson, et al., *J Immunol* 2001; 166: 795-799; Kuo, et al., *Genes Dev* 1997a; 11: 2996-3006; Wu, et al., *J Immunol* 2005; 175: 3060-3066), Klf2 expression was rapidly downregulated following TCR activation (more than 100-fold) (FIG. 5a). Klf2 mRNA expression rebounded somewhat after extended culture of TCR-activated T cells in IL-2, though even under these conditions Klf2 mRNA levels remained 10- to 20-fold lower than those seen in resting T cells (FIG. 5a). Klf2 expression was also decreased in resting CCR6$^+$ T$_M$ cells upon stimulation with IL-7 alone (FIG. 5b). These data indicate that γc-dependent induction of IL-17/IL-22 parallels Klf2 downregulation. Importantly, treatment of T$_M$ cells with PI-3K/Akt inhibitors reversed cytokine-mediated Klf2 downregulation (FIG. 5b and FIG. 11b).

Figure 5C:
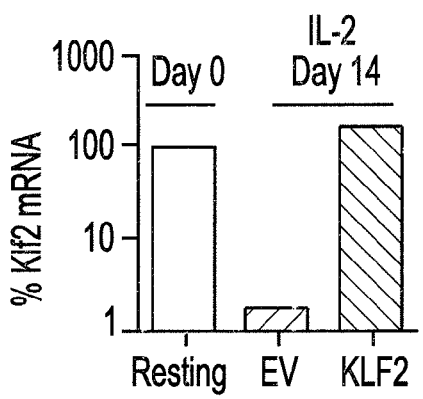
Figure 6A:
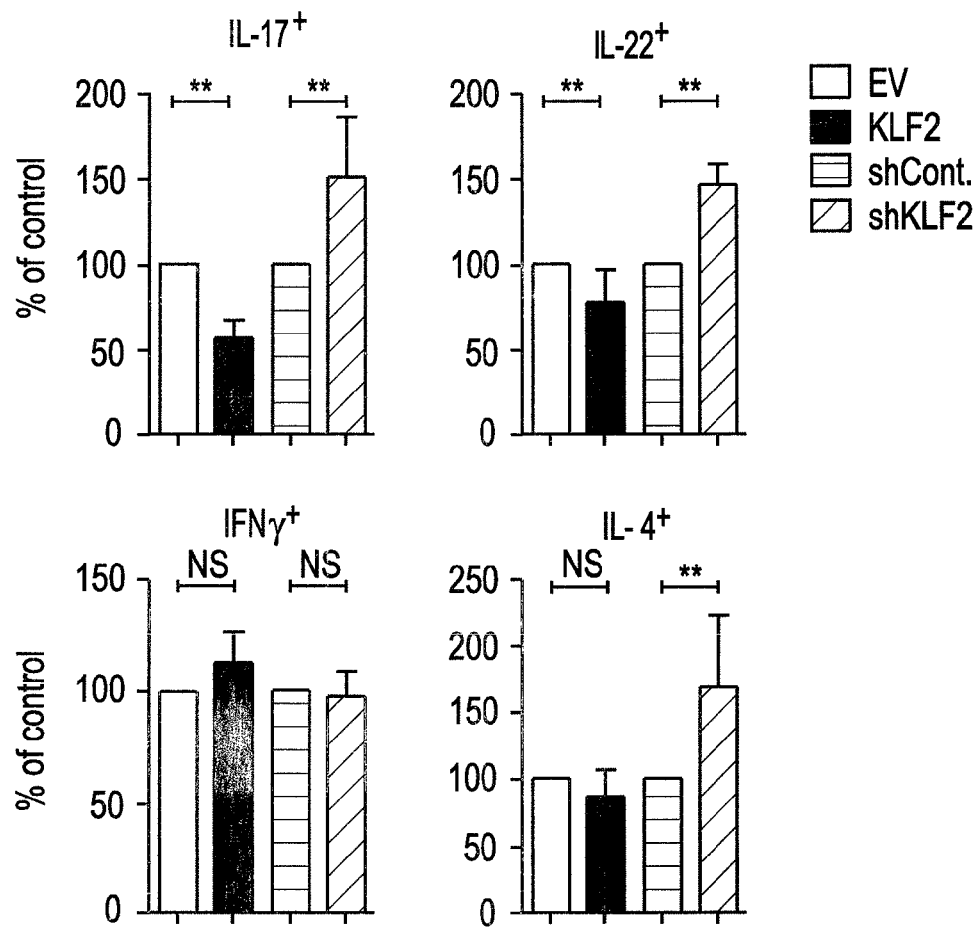
FIG. 6 demonstrates that KLF2 suppresses IL-17 and IL-22 production from CCR6$^+$ memory T cells in the presence of ectopic RORC expression. (a, b). KLF2- or shKLF2-transduced CCR6$^+$ T$_M$ cells cultured for 2 weeks in IL-2 medium were treated with PMA and ionomycin, and then subjected to intracellular IL-17, IL-22, IFNγ and IL-4 staining shCont.: control shRNA, shKLF2: KLF2 shRNA. The frequency of single- or double-cytokine-producing cells from either EV or shCont. transduced cells was normalized to 100%. (c) RORC overexpression and silencing of KLF2 are synergistic on induction of IL-17. CCR6$^-$ T$_M$ cells co-transduced with shKLF2- and RORC-expressing lentiviruses or their corresponding controls were restimulated with PMA and ionomycin for 5 hours. Cells were then stained with antibodies against IL-17, IL-22, IFNγ and IL-4 and shown as dot plots in (c) from a representative donor, or graphically from multiple donors in (d). Data are presented as mean percentage of cytokine±SD from at least three individual donors and independent experiments. * p<0.05, ** p<0.005. NS: no significance.
Figure 11C:
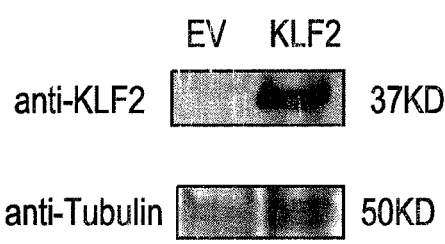
Figure 11D:
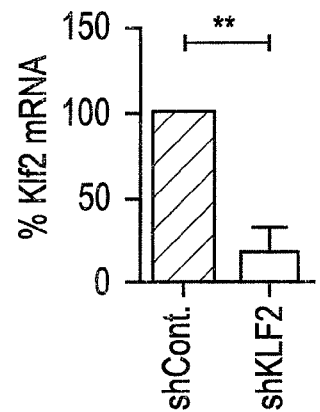

To directly address the putative function of PI-3K-mediated Klf2 downregulation on IL-17 and IL-22 expression, KLF2 expression in cytokine-stimulated T$_M$ cells using lentiviral transduction was restored (FIG. 11c). Human T$_M$ cells transduced with KLF2-expressing lentiviruses displayed Klf2 mRNA levels comparable to either resting T cells (FIG. 5c) or cytokine-stimulated T cells treated with LY294002 (FIG. 5b). Upon restimulation, human CCR6$^+$ T$_M$ cells ectopically expressing KLF2 produced less IL-17 or IL-22 compared to cells transduced with control lentiviruses (FIG. 6a, 6b), whereas neither IFNγ nor IL-4 was affected (FIG. 6a). In contrast to KLF2 overexpression, shRNA-mediated silencing of endogenous KFL2 (FIG. 11d) enhanced IL-17/

Figure 6B:
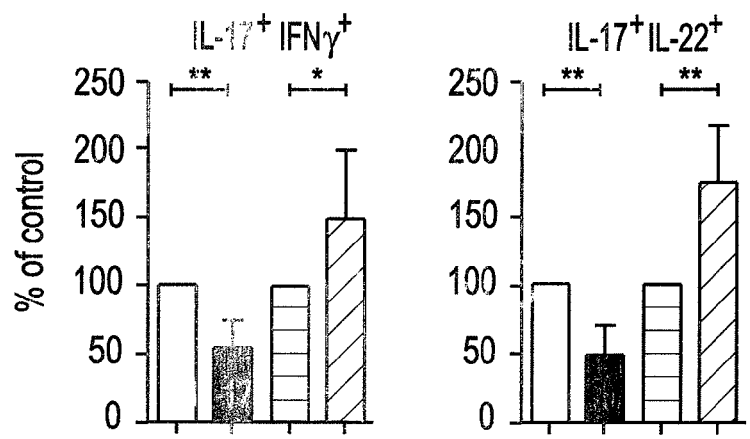

IL-22 secretion by human CCR6⁺ T$_M$ cells (FIG. 6a, 6b). Interestingly, T cells expressing KLF2 shRNA also displayed enhanced IL-4 expression particularly within the CCR6⁺ subset (FIG. 6a), suggesting that KLF2 may regulate expression of a broader set of cytokines in memory T cell subsets.

Figure 6C:
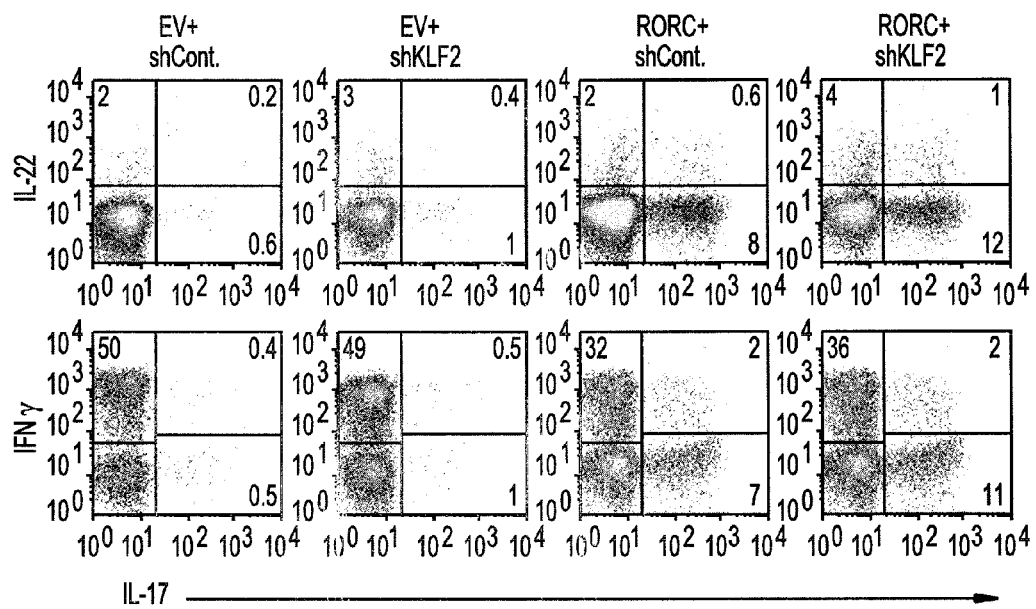
Figure 6D:
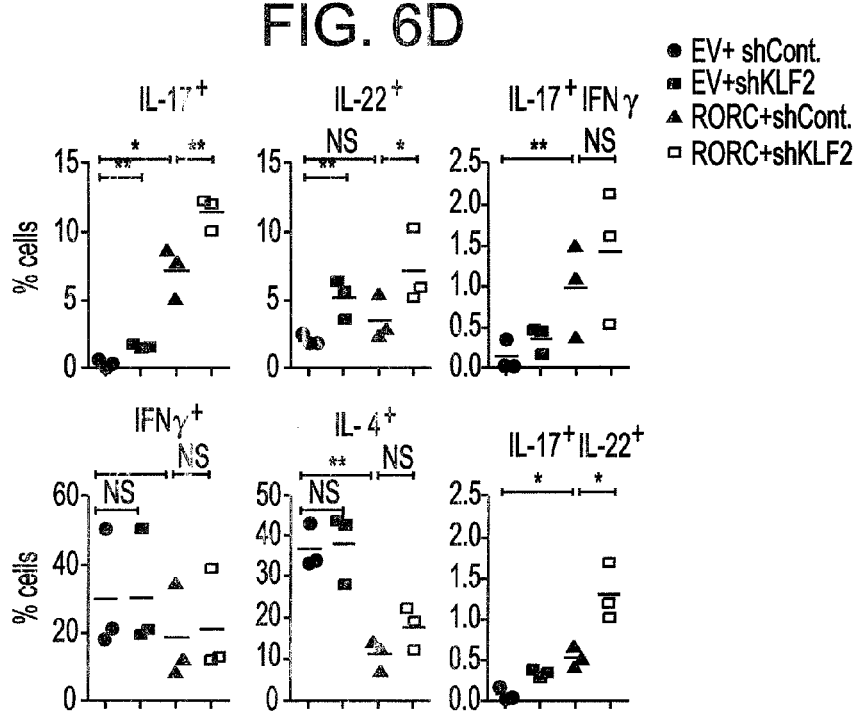

CCR6⁻ T$_M$ cells also express KLF2, and shRNA-mediated knockdown of KLF2 in these cells also enhanced residual IL-17 or IL-22 expression (FIG. 6c, 6d). Because high-level IL-17 expression by CCR6⁻ T$_M$ cells can only be achieved by forced expression of RORC (FIG. 6c, 6d) (Manel, et al., *Nature Immunology* 2008; 9: 641-649), whether KLF2 regulates RORC-mediated IL-17 expression in CCR6⁻ T$_M$ cells was investigated. Indeed, knockdown of KLF2 further enhanced RORC-induced IL-17 production in CCR6⁻ T$_M$ cells (FIG. 6c, 6d). These findings suggest that endogenous KLF2 restrains RORC-mediated induction of IL-17.

What is claimed is:

1. A method for inhibiting activation of Th17+ or Th22+ cells or inhibiting Th17+ or Th22+ cell biological activity comprising administering Krüppel-like transcription factor 2 (KLF2) and inhibiting activation or biological activity of Th17+ or Th22+ cells.

2. A method for inhibiting an immune response comprising administering Krüppel-like transcription factor 2 (KLF2) and decreasing the activation or biological activity of Th17+ or Th22+ cells.

3. A method for inhibiting activation of Th17+ or Th22+ cells or inhibiting Th17+ or Th22+ cell biological activity in vitro comprising administering a genetic construct encoding Krüppel-like transcription factor 2 (KLF2) in vitro and inhibiting activation or biological activity of Th17+ or Th22+ cells.

4. A method for inhibiting an immune response in vitro comprising administering a genetic construct encoding Krüppel-like transcription factor 2 (KLF2) in vitro and decreasing the activation or biological activity of Th17+ or Th22+ cells.

* * * * *